US007235675B2

(12) United States Patent
Ghoshal et al.

(10) Patent No.: US 7,235,675 B2
(45) Date of Patent: Jun. 26, 2007

(54) CONJUGATES OF MYCOPHENOLIC ACID

(75) Inventors: Mitali Ghoshal, Noblesville, IN (US); Gerald Sigler, Carmel, IN (US); Raymond A. Hui, Indianapolis, IN (US); Ronald Hawley, Mountain View, CA (US); Eva Hoess, Munich (DE); Erasmus J. Huber, Finning (DE); John W. Patterson, Mountain View, CA (US); Salvatore J. Salamone, Stockton, NJ (US); Allan Dorn, Carmel, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 10/900,447

(22) Filed: Jul. 27, 2004

(65) Prior Publication Data

US 2005/0009076 A1    Jan. 13, 2005

Related U.S. Application Data

(60) Division of application No. 10/341,692, filed on Jan. 14, 2003, now Pat. No. 6,811,998, which is a continuation-in-part of application No. 09/603,646, filed on Jun. 26, 2000, now Pat. No. 6,524,808.

(60) Provisional application No. 60/141,098, filed on Jun. 25, 1999.

(51) Int. Cl.
C07D 307/00    (2006.01)
C07D 407/00    (2006.01)
(52) U.S. Cl. ..................................... 549/304
(58) Field of Classification Search ................ 435/26, 435/69.2, 188; 549/304
See application file for complete search history.

(56) References Cited

U.S. PATENT DOCUMENTS

| 1,595,101 | A | 8/1926 | Tonkes et al. | |
| 4,134,792 | A | 1/1979 | Boguslaski et al. | 195/99 |
| 4,273,866 | A | 6/1981 | Voss et al. | 435/7 |
| 4,341,865 | A | 7/1982 | Voss | 435/7 |
| 4,510,251 | A | 4/1985 | Kirkemo et al. | 436/536 |
| 5,352,803 | A | 10/1994 | Mattingly | 549/220 |
| 5,493,030 | A | 2/1996 | Morgans, Jr. et al. | 548/230 |
| 5,496,925 | A | 3/1996 | Mattingly | 530/350 |
| 5,512,568 | A | 4/1996 | Morgans, Jr. et al. | 514/233.5 |
| 5,525,602 | A | 6/1996 | Patterson et al. | 514/233.5 |
| 5,538,969 | A | 7/1996 | Morgans, Jr. et al. | 514/233.5 |
| 5,554,612 | A | 9/1996 | Patterson et al. | 514/233.5 |
| 5,573,904 | A | 11/1996 | Mattingly | 435/4 |
| 5,616,298 | A | 4/1997 | Mattingly | 422/61 |
| 5,633,279 | A | 5/1997 | Morgans, Jr. et al. | 514/468 |
| 5,756,771 | A | 5/1998 | Mattingly | 549/223 |
| 5,807,876 | A | 9/1998 | Armistead et al. | 514/374 |
| 6,107,052 | A | 8/2000 | Dorn | 435/25 |
| 6,225,073 | B1 | 5/2001 | Alexander et al. | 435/7.93 |
| 6,524,808 | B1 | 2/2003 | Dorn et al. | |
| 6,811,998 | B2 * | 11/2004 | Ghoshal et al. | 435/26 |

FOREIGN PATENT DOCUMENTS

| EP | 1 054 258 | | 11/2000 |
| EP | 1207394 A2 | | 5/2002 |
| WO | WO 97/41211 | | 11/1997 |
| WO | WO 99/33996 | | 7/1999 |
| WO | WO 01/01135 | | 1/2001 |
| WO | WO 01/01135 A1 | | 1/2001 |
| WO | 0101135 | * | 4/2001 |

OTHER PUBLICATIONS

Dorn, Allan et al., Abstract of Oak Ridge Posters, Clinical Chemistry 47, No. 10 (2001) p. 1921-1922.
Nelson, P.H. et al. "Structure-Activity Relationships for Inhibition of Inosine Monophosphate Dehydrogenase by Nuclear Variants of Mycophenolic Acid," J. Med. Chem., 1996, 39, 4181-4196.
Nelson, P.H. et al., "Synthesis and Immunosuppressive Activity of Some Side-Chain Variants of Mycophenolic Acid," J. Med. Chem, 1990, 33, 833-838.
Smith, D.B. et al., "Asymmetric Synthesis and Stereochemical Assignment o RS-97613, a Potent Immunosuppressive and Antiinflammatory Agent," J. Org. Chem., 1996, 61, 2236-2241.
Zhang, Han-Zhong et al., "Rationally Designed Inhibitors of Inosine Monophosphate Dehydrogenase," J. Med. Chem., 1997, 40, 4-8.
Carr, S.F., Papp, E., Wu, C., Natsumeda, Y., "Characterization of Human Type I and Type II IMP Dehydrogenases" Journal of Biological Chemistry. vol. 268, No. 36, 1993, 27286-27290.
Sintchak, M.D., Fleming, M.A., Futer, O., Raybuck, S.A., Chambers, S.P., Caron, P.R., Murcko, M.A., Wilson, K.P. "Structure and Mechanism of Inosine Monophosphate Dehydrogenase in Complex with the Immunosuppressant Mycophenolic Acid". Cell, vol. 85, 921-930, Jun. 14, 1996.
Ross, R., Horwitz, C.A., Hager, H., Usategui, M., Burke, M.D., Ward, P.C.J. "Preliminary Evauation of a Latex Agglutination-Inhibition Tube Test for Morphine", Clin. Chem. 21/1, 139-143, 1975.

(Continued)

Primary Examiner—D. Margaret Seaman
Assistant Examiner—Niloofar Rahmani
(74) Attorney, Agent, or Firm—Merilyn L. Amick; Roche Diagnostics Operations, Inc.

(57) ABSTRACT

The present invention provides a method for the measurement of an analyte in biological samples whereby an uncompetitive inhibitor is coupled to a ligand and utilized in a homogeneous assay. The analyte can be a drug or drug derivative, hormone, polypeptide, or oligonucleotide.

The present invention also provides novel compounds, assay reagents and packaged kits useful for performing such measurements.

10 Claims, 31 Drawing Sheets

OTHER PUBLICATIONS

Clark, B.R., Deshpande, S.V., Sharma, S.D., Nag, B. "Antigen-specific Deletion of Cloned T Cells Using Peptide-Toxin Conjugate Complexed with Purified Class II Major Histocompatibility Complex Antigen". Journal of Biological Chemistry, vol. 269, No. 1, Issue of Jan. 7, 1994, pp. 94-99.

Place, M.A., Carrico, R.J., Yeager, F.M., Albarella, J.P., Boguslaski, R.C. "A Colorimetric Immunoassay Based on an Enzyme Inhibitor Method". Journal of Immunological Methods, 61, (1983), 209-216.

Bacquet, C, and Twumasi, D.Y. "Homogeneous Enzyme Immunoassay with Avidin-Ligand Conjugate as the Enzyme-Modulator." Analytical Biochemistry 136, (1984), 487-490.

Finley, P.R., Williams, R.J., Lichti, D.A. "Evaluation of a New Homogeneous Enzyme Inhibitor Immunoassay of Serum Thyroxine with Use of a Bichromatic Analyzer", Clin. Chem. 26/12, 1723-1726, (1980).

Nimmesgern, E., Fox, T., Fleming, M.A., Thomson, J.A. "Conformational Changes and Stabilization of Inosine 5'-Monophosphate Dehydrogenase Associated with Ligand Binding and Inhibition by Mycophenolic Acid", The Journal of Biological Chemistry, 1996, vol. 271, No. 32, pp. 19421-19427.

* cited by examiner

MPA

MPA-MPA

CONJUGATES OF MYCOPHENOLIC ACID

CROSS-REFERENCE TO RELATED APPLICATIONS

This application is a divisional of U.S. application Ser. No. 10/341,692 filed Jan. 14, 2003, now U.S. Pat. No. 6,811,998 which is a continuation-in-part of U.S. application Ser. No. 09/603,646 filed Jun. 26, 2000, now U.S. Pat. No. 6,524,808 which claims priority to U.S. provisional application No. 60/141,098 filed Jun. 25, 1999. Priority is also claimed to PCT application PCT/US00/17541 filed Jun. 26. 2000.

BACKGROUND OF THE INVENTION

This invention relates generally to the field of measuring an analyte in a liquid medium. More specifically, it relates to an immunoassay for the measurement of an analyte in a biological sample.

Boguslaski, R. C. et al., U.S. Pat. No. 4,134,792 (1979) describe the use of a reversibly binding enzyme modulator as a labeling substance for the detection of an analyte in a liquid medium, and in particular, the use of competitive inhibitors coupled to an analog of the analyte in immunoassays.

Dorn, A. R., U.S. Ser. No. 09/328,741 filed Jun. 9, 1999 describes a method for the enzymatic measurement of mycophenolic acid in a biological sample.

Inosine-5'-monophosphate dehydrogenase (EC 1.1.1.205) catalyzes the NAD-dependent oxidation of inosine-5'-monophosphate (IMP) to xanthosine-5'-monophosphate (XMP), Magasanik, B. et al., *J. Biol. Chem.* 226:339–350 (1957) and Jackson et al., *Nature* 256:331–333 (1975). The enzyme follows an ordered Bi—Bi reaction sequence of substrate and cofactor binding and product release. First, IMP binds to IMPDH. This is followed by the binding of the cofactor NAD. The reduced cofactor, NADH, is then released from the product, followed by the product, XMP. This mechanism differs from that of most other known NAD-dependent dehydrogenases, which have either a random order of substrate addition or require NAD to bind before the substrate.

Two isoforms of human IMPDH, designated type I and type II, have been identified and sequenced, Collart et al., *J. Biol. Chem.* 263:15769–15772 (1988) and Natsumeda et al., *J. Biol. Chem.* 265:5292–5295 (1990). Each isoform is 514 amino acids, and both isoforms share 84% sequence identity. Both IMPDH type I and type II form active tetramers in solution, with subunit molecular weights of 56 kDa, Yamada et al., *Biochemistry* 27:2737–2745 (1988).

SUMMARY OF THE INVENTION

In its narrowest application, the present invention is exemplified by a quantitative homogeneous immunoassay specific for mycophenolic acid based upon the specific uncompetitive inhibition of the enzyme inosine-5'-monophosphate dehydrogenase (IMPDH) by mycophenolic acid. IMPDH inhibition depends only upon the concentration of mycophenolic acid due to the uncompetitive nature of inhibition by mycophenolic acid. Thus, the greater the mycophenolic acid concentration, the greater the inhibition of the enzyme. Measuring the formation of reduced nicotinamide adenine dinucleotide (NADH) at 340 nm monitors the reaction. IMPDH catalyzes the following reaction:

inosine-monophosphate+NAD$^+$ →$^{IMPDH}$→ xanthosine monophosphate+NADH

Development of a homogeneous immunoassay can be accomplished through the attachment of a ligand to a position on mycophenolic acid or an MPA derivative or any uncompetitive inhibitor of IMPDH where such attachment does not interfere with the uncompetitive inhibition of IMPDH. In the absence of analyte, analyte-specific antibody binds the ligand-MPA derivative and prevents its inhibition of IMPDH. In the presence of analyte, analyte binds to its antibody, thus freeing up ligand-MPA derivative to inhibit IMPDH (Table 3, part C.).

The rate of formation of NADH (reduced nicotinamide adenine dinucleotide) can be measured by monitoring the change in absorption at a wavelength of 340 nm, i.e., the characteristic absorption region of NADH, and this change in absorption can then be correlated to analyte concentration.

Attractive positions for ligand attachment occur on the hexanoic chain of mycophenolic acid and its derivatives, especially at the 4' carbon and the 5' carbon (FIG. 1). Several compounds meet these criteria. See Nelson, P. H. et al., *Journal of Medicinal Chemistry* 33:833–838 (1990), Rohloff, J. C.,et al., *Tetrahedron Letters* 36 (43):7803–7806 (1995), Artis, D. R. et al., PCT Publication WO 95/22536 (1995) and Artis, D. R. et al., PCT Publication WO 95/22538 (1995). Several of these derivatives show greater inhibition than mycophenolic acid and thus could impart greater sensitivity to a homogeneous immunoassay. See Smith, D. B. et al., *J. Org. Chem.* 61:2236–2241 (1996).

In a preferred embodiment of the present invention, an uncompetitive inhibitor, mycophenolic acid (MPA) was coupled to a ligand and used in a homogeneous immunoassay for mycophenolic acid.

Use of an uncompetitive inhibitor-ligand conjugate is preferred over a competitive inhibitor-ligand conjugate since the former conjugate is far less susceptible to interferences from drugs and naturally occurring substances, which commonly can be competitive inhibitors of enzymes. Uncompetitive inhibitors of enzymes are rare in nature and should therefore be less susceptible to interferences from drugs and natural substances.

In its broadest application, the present invention can be used to measure any analyte. Specifically exemplified herein is the use of the invention for measurement of mycophenolic acid, digoxigenin, thyroxin and theophylline. Also taught is the use of the invention for measurement of any analyte including drugs or drug derivatives, hormones, polypeptides and oligonucleotides. Examples of other drugs or drug derivatives which would be suitable for assay using the method of the present invention include therapeutic drugs such as antibiotics, e.g., gentamicin, amikacin, tobramycin, netilmicin and vancomycin; cardiac drugs, e.g., digoxin, digitoxin, N-acetyl procainamide, procainamide, quinidine and lidocaine; anti-seizure drugs, e.g., phenytoin, phenobarbital, primidone, valproic acid, ethosuximide and carbamazepine; analgesics, e.g., acetaminophen and acetylsalicylic acid; and immunosuppressants, e.g., MPA, cyclosporin, rapamycin (sirolimus) and FK506 (tacrolimus), and drugs of abuse such as amphetamines, barbiturates, benzodiazepines, cannabinoids, cocaine metabolite (benzoylecgonine), methadone, opiates, phencyclidine, propoxyphene and LSD. Examples of hormones which would be suitable for assay using the method of the present invention include thyroxine, thyroid stimulating hormone, estrogen, progesterone, testosterone, prolactin, follicle stimulating hormone, chorionic gonadotropin and leuteinizing hormone. Examples of polypeptides which would be suitable for assay using the method of the present invention include proteins and epitopes such as hemoglobin A1c, troponin-T and troponin-I. Examples of oligonucleotides which would be suitable for assay using the method of the present invention include specific oligonucleotide sequences that can hybridize under stringent conditions with sequences sufficiently specific for the detection and quantification of gonorrhoeae, human immunodeficiency virus (HIV), chlamydia and hepatitis infections.

Another aspect of the present invention relates to a test kit for conducting an assay for the determination of as analyte via the method of the present invention comprising, in packaged combination, one or more reagent compositions comprising NAD, IMPDH, IMP and a conjugate comprising MPA and a ligand of the analyte.

DETAILED DESCRIPTION OF THE INVENTION

Figure 1:
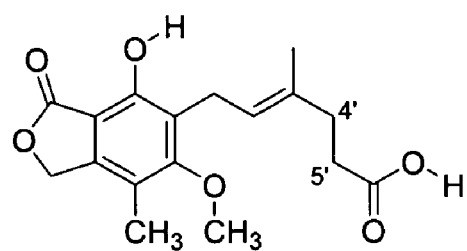
FIG. 1 illustrates the structure of mycophenolic acid and the structure of the ligand-inhibitor conjugate, MPA-MPA (bis-MPA).
Figure 1:
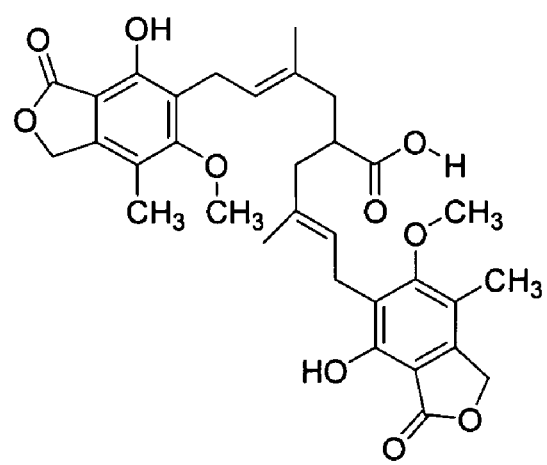

It has been found that there are some properties of mycophenolic acid inhibition of IMPDH that should facilitate the development of homogeneous enzyme immunoassays. The sensitivity (10–20 nM) of mycophenolic acid inhibition and its uncompetitive inhibition favor its use in homogeneous enzyme immunoassays. By carefully coupling a ligand to mycophenolic acid to form a ligand-inhibitor conjugate, one can develop a homogeneous enzyme immunoassay for a specific analyte. Coupling a ligand to an uncompetitive inhibitor is greatly preferred in the specific case of mycophenolic acid measurement since many competitive inhibitors of IMP and NAD exist and would reduce assay specificity. In general, use of competitive inhibitors in ligand-inhibitor conjugates will lead to interferences in assay performance since many drugs and naturally occurring substances occur as competitive inhibitors, which would greatly reduce specificity.

An uncompetitive inhibitor of IMPDH enzyme is a substance that inhibits by binding at the active site of the enzyme and does not compete with IMP or NAD for inhibition of the enzyme. Uncompetitive inhibition occurs when an inhibitor combines reversibly with the IMPDH-XMP complex at the active site of the enzyme to form IMPDH-XMP-inhibitor complex, which then is unable to release the XMP product. This type of inhibition is not reversed by increasing substrate concentration. NADH is released only once, while XMP is not released. On the other hand, noncompetitive inhibitors bind at a site other than the substrate binding site. Noncompetitive inhibition is also not reversed by increased substrate concentration.

The IMPDH enzyme preferred for use is a recombinant IMPDH-II enzyme from human T lymphocytes.

The sensitivity of the present immunoassay to the analyte concentration may be modified through the use of different forms of IMPDH that vary in sensitivity to inhibition by MPA. For example, the inhibitor constants ($K_i$) of several forms of human IMPDH for MPA are as follows:

| IMPDH form | $K_i$ ($IC_{50}$) | Reference |
| --- | --- | --- |
| IMPDH-I | 37 nM | J. Biol. Chem. 268, 27286–27290 (1993) |
| IMPDH-II | 9.5 nM | J. Biol. Chem. 268, 27286–27290 (1993) |
| IMPDH-II ser 275 → ala 275 | 4 nM | Cell 85, 921–930 (1996) |

Since the different enzyme forms have varied sensitivities to MPA inhibition, they should also have varied sensitivities to inhibition by ligand-inhibitors and thus have utility in producing immunoassays with differing levels of sensitivity or measuring ranges of analytes.

The invention provides for the adjustment of assay sensitivity. The adjustment or modification of assay sensitivity may not be easily obtainable without the use of different forms of IMPDH of varied sensitivity to MPA or MPA derivatives or any uncompetitive inhibitor of IMPDH.

Sample suspected of containing the analyte: Any sample that is reasonably suspected of containing the analyte, i.e., mycophenolic acid or other IMPDH inhibitor, can be analyzed by the method of the present invention. The sample is typically an aqueous solution such as a body fluid from a host, for example, urine, whole blood, plasma, serum, saliva, semen, stool, sputum, cerebral spinal fluid, tears, mucus or the like, but preferably is plasma or serum. The sample can be pretreated if desired and can be prepared in any convenient medium that does not interfere with the assay. An aqueous medium is preferred.

Measuring the amount of mycophenolic acid: Quantitative, semi-quantitative and qualitative methods as well as all other methods for determining mycophenolic acid are considered to be methods of measuring the amount of mycophenolic acid. For example, a method that merely detects the presence or absence of mycophenolic acid in a sample suspected of containing mycophenolic acid is considered to be included within the scope of the present invention. The terms "detecting" and "determining", as well as other common synonyms for measuring, are contemplated within the scope of the present invention.

The determination of MPA according to the present invention may be conducted by a rate-assay method wherein change in absorbance of NADH per unit time is measured or by an end-point method wherein the reaction is quenched after a certain period of time has elapsed. The method can easily be applied to automated analyzers for laboratory or clinical analysis. Examples of automated laboratory analyzers are COBAS INTEGRA and ROCHE/HITACHI series analyzers (Roche Diagnostics, Indianapolis, Ind.). Other methods for measuring NADH are also contemplated, for example, the reduction of NAD is coupled to the reduction of a tetrazolium salt, 2-p-nitrophenyl-5-phenyl tetrazolium chloride (INT), with phenazine methosulfate serving as an intermediate electron carrier, as described in Babson, A. L. et al, *Clinical Chemistry* 19(7):766–769 (1973).

Calibration material means any standard or reference material containing a known amount of the analyte to be measured. The sample suspected of containing the analyte and the calibration material are assayed under similar conditions. Analyte concentration is then calculated by comparing the results obtained for the unknown specimen with results obtained for the standard. This is commonly done by constructing a calibration curve such as in FIGS. 2, 3, 4 and 5.

Ancillary materials: Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumin, or surfactants, particularly nonionic surfactants, or the like.

IMPDH refers to the enzyme inosine-5'-monophosphate dehydrogenase, EC 1.1.1.205, which catalyzes the formation of xanthine-5'-monophosphate from inosine-5'-monophosphate. The present invention contemplates the use of IMPDH from natural or recombinant sources or site-directed mutants, and any isoform, site-directed mutant or a mixture of isoforms may be used.

It is to be understood that any reference throughout the specification and claims to mycophenolic acid is meant to cover mycophenolic acid as well as its biologically active and therapeutically active metabolites and derivatives, which behave in a biological sense, i.e. via IMPDH inhibition, as mycophenolic acid.

Another aspect of the present invention relates to kits useful for conveniently performing the assay methods of the invention for the determination of an analyte. To enhance the versatility of the subject invention, reagents useful in the methods of the invention can be provided in packaged combination, in the same or separate containers, in liquid or lyophilized form so that the ratio of the reagents provides for substantial optimization of the method and assay. The reagents may each be in separate containers or various reagents can be combined in one or more containers depending on the cross-reactivity and stability of the reagents.

The kit of the present invention comprises NAD, a ligand-inhibitor conjugate comprising an inhibitor of IMPDH and a ligand of the analyte, IMP and IMPDH. The reagents may remain in liquid form or may be lyophilized. The kit can further comprise calibration and control materials.

However, the present invention has applications beyond the measurement of mycophenolic acid. Using the approach described here, any ligand (such as, but not limited to, theophylline, digoxin, phenytoin, peptide fragments, oligonucleotides, morphine, cocaine etc.) that has been derivatized with an appropriate reactive group for attachment to mycophenolic-acid or MPA derivatives or any uncompetitive enzyme inhibitor of IMPDH suitably derivatized at the 4'-position or the 5'-position can be used to measure the corresponding analyte in an unknown sample. Derivatization at these positions creates new optically active centers. Stereoisomers are considered within the scope of the present invention.

A central feature of the present invention is the ability to synthesize MPA derivatives substituted at the 5'-position with a suitable linking group which can be extended to couple to drug derivatives. Two different types of linking groups have been disclosed in this invention, 5'-carboxy alkyl MPA drug derivatives and 5'-isoprenyl linking MPA drug derivatives.

Substitution at the 5'-position of MPA ester involves alkylation reaction using alkyl halo acetate in the presence of sodium bis(trimethylsilyl)amide and DMPU at low temperature. Use of HMPA instead of DMPU appeared to improve the alkylation reactions in general. This alkylation reaction can be extended to use alkyl halo propionate or alkyl halo butyrate to prepare 5'-carboxyethyl MPA ester or 5'-carboxypropyl MPA ester after selective ester hydrolysis at the linker. The carboxy function at the linker then permits a wide variety of synthetic routes by conversion to an active ester and then to couple to suitably derivatized drug derivatives, most commonly, a drug with a linker-containing amino group to generate an amide linkage.

The substitution at the 5'-position of MPA ester using bromo-isoprenyl linker (1) in the presence of sodium bis(trimethylsilyl)amide and HMPA provided MPA 5'-isoprenyl TBDPS derivative. Hydrolysis of TBDPS group provided 5'-isoprenyl[OH]-MPA[OMEM] (5). This key intermediate alcohol has been activated by conversion to N-hydroxysuccinimidyl carbonate by treatment with disuccinimidyl carbonate in the presence of triethyl amine. The activated carbonate was used without isolation to couple to amino modified drugs to provide MPA drug conjugates with a urethane linkage. The urethane linkage can also be produced by use of activation of the alcohol with 1,1'-carbonyldiimidazole or p-nitrophenyl chloroformate and reaction of the intermediates with the amino group modified drug derivatives. This synthesis can be extended to MPA bis-isoprenyl drug conjugates by use of bromo-bis isoprenyl TBDPS. The bromo-bis-isoprenyl TBDPS can be prepared from geraniol derivative following the literature procedure as described for chloro-bis-isoprenyl TBDPS in *J. Org. Chem.* 62, 3529 (1997).

The MPA-drug conjugates with an urethane (carbamate) linkage in the linker, as discussed above, may then be deprotected using reagents known in the art, but usually with some care being required. As an example, the protecting group on the phenolic hydroxy of the benzene nucleus of MPA itself, such as, for example, the methoxyethoxymethyl-group (MEM group) used in various of the examples may be removed with the commonly used trifluoroacetic acid (TFA) diluted into methylene chloride ($CH_2Cl_2$). However, application of standard or frequently used conditions result in cleavage of the carbamate linkage in the linker as well, sundering the drug from the MPA, as exemplified by rupture of the protected MPA-thyroxin conjugate (9) when treated with 1:1 TFA in $CH_2Cl_2$ at room temperature. Application of dilute and limited amounts of TFA in $CH_2Cl_2$ at lower temperatures under carefully controlled conditions, however, and as exemplified in the present invention, were successful in furnishing the desired deprotected MPA-drug conjugates. An additional example of the careful deprotection required is illustrated by the deprotection of the fully-protected MPA-gentamicin conjugate (N) to the desired final deprotected MPA-gentamicin conjugate (R) wherein one required the sequential removal of the methyl ester and N-trifluoroacetate groups, using mild basic conditions, followed by removal of three t-BOC groups and one MEM group, achieved under mild but controlled acidic conditions.

Because of the extra care needed in the deprotection sequences when the linker contained the urethane linkage or group, use of an amide linkage instead has benefits including much greater stability and resistance to rupture under mild conditions. Complementary to the use of the carboxyalkyl MPA derivatives discussed previously, use of an MPA-5'-isoprenylamine derivative (as an alternative to the 5'-isoprenyl alcohol discussed above) would generate the corresponding MPA-drug conjugates with a more stable amide linkage.

Figure 19:
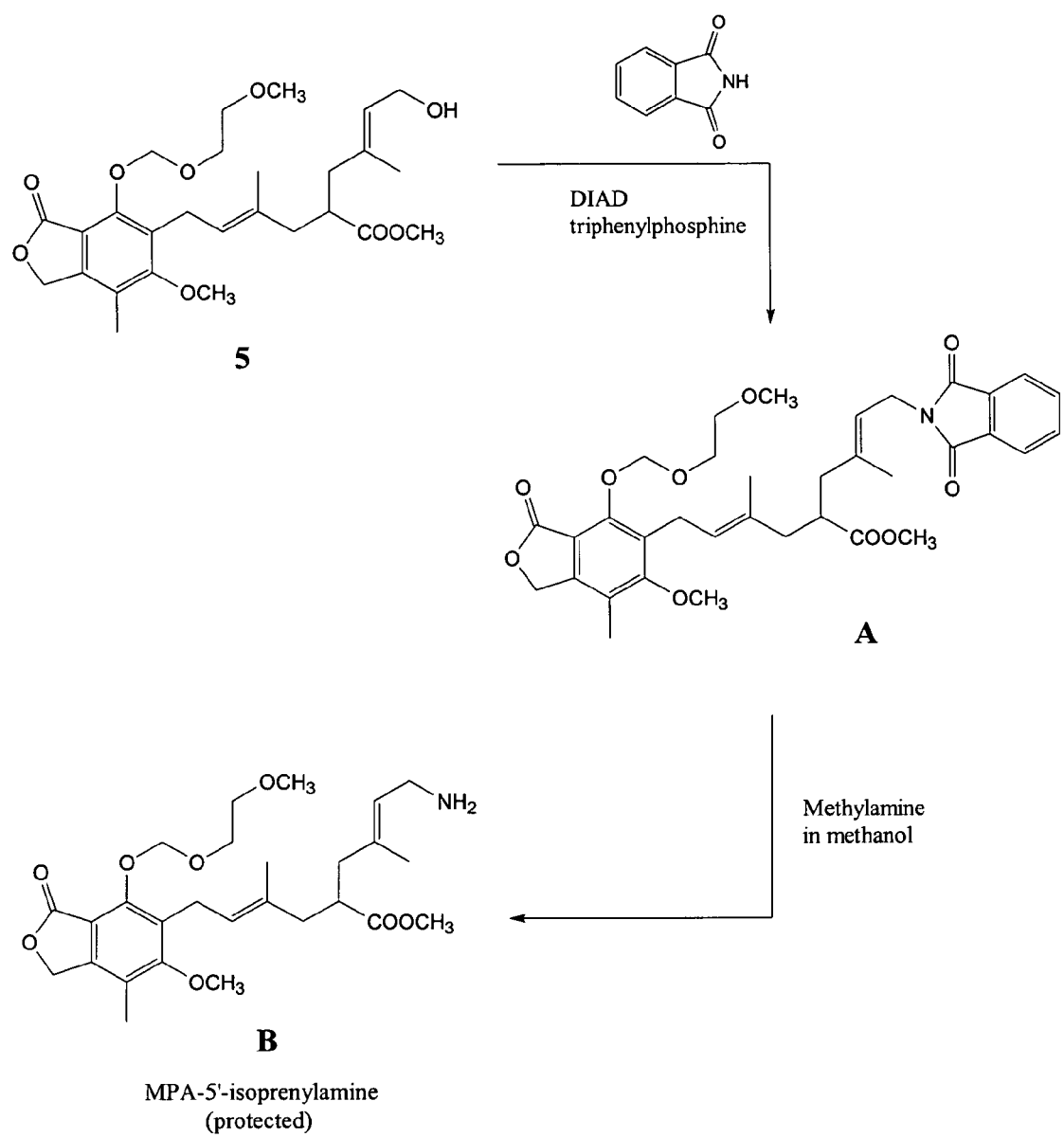
FIG. 19 illustrates the preparation of MPA[OMEM]-5'-isoprenylamine methyl ester (B) as described in Examples 44 and 45.
Figure 24A:
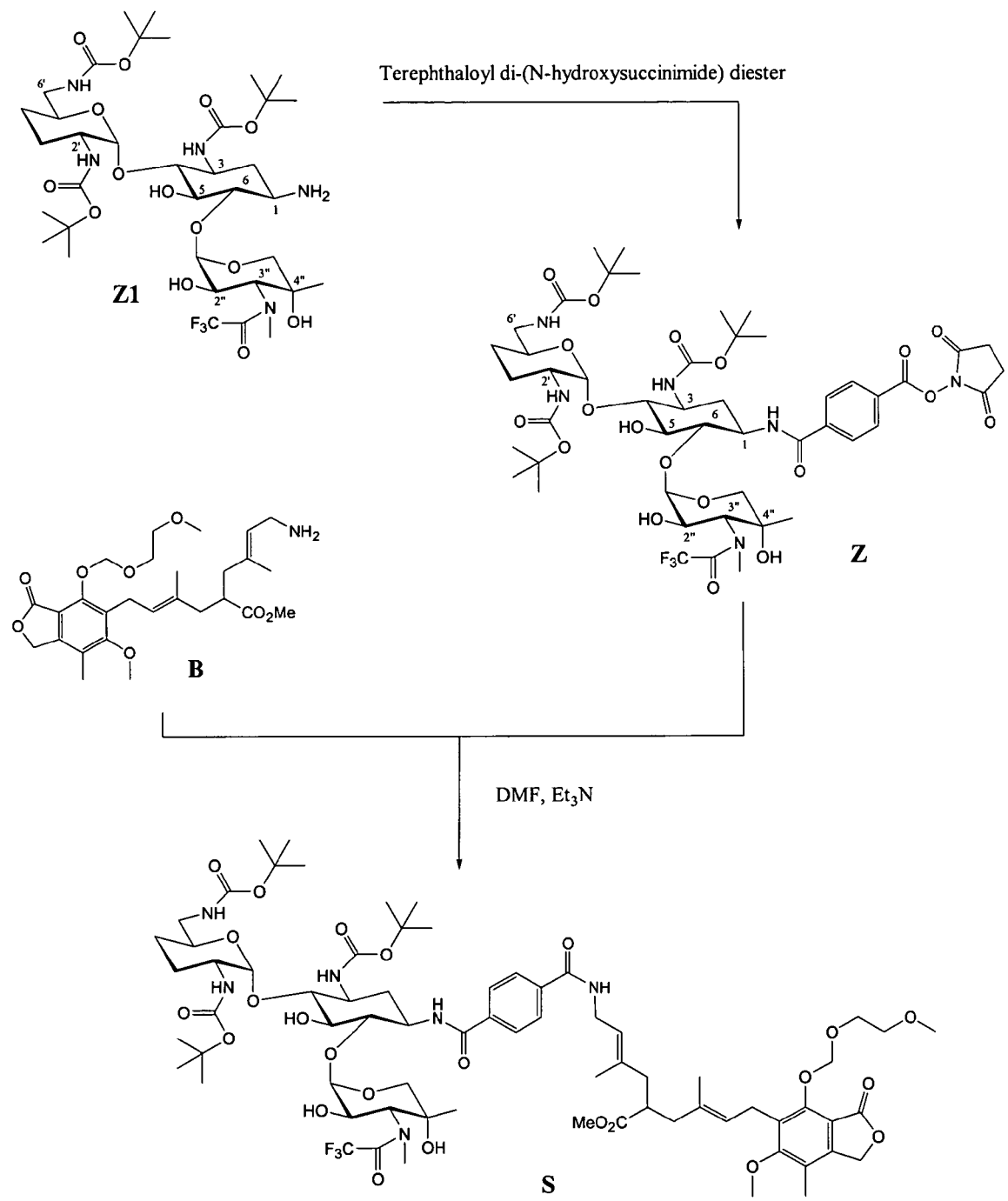
FIGS. 24a and 24b illustrate the preparation of 5'-[(gentamicin[C1a]-N$^1$-terephthaloyl)-amino-isoprenyl]-MPA conjugate (amide linkage, U) as described in Examples 52, 53 and 54.
Figure 24B:
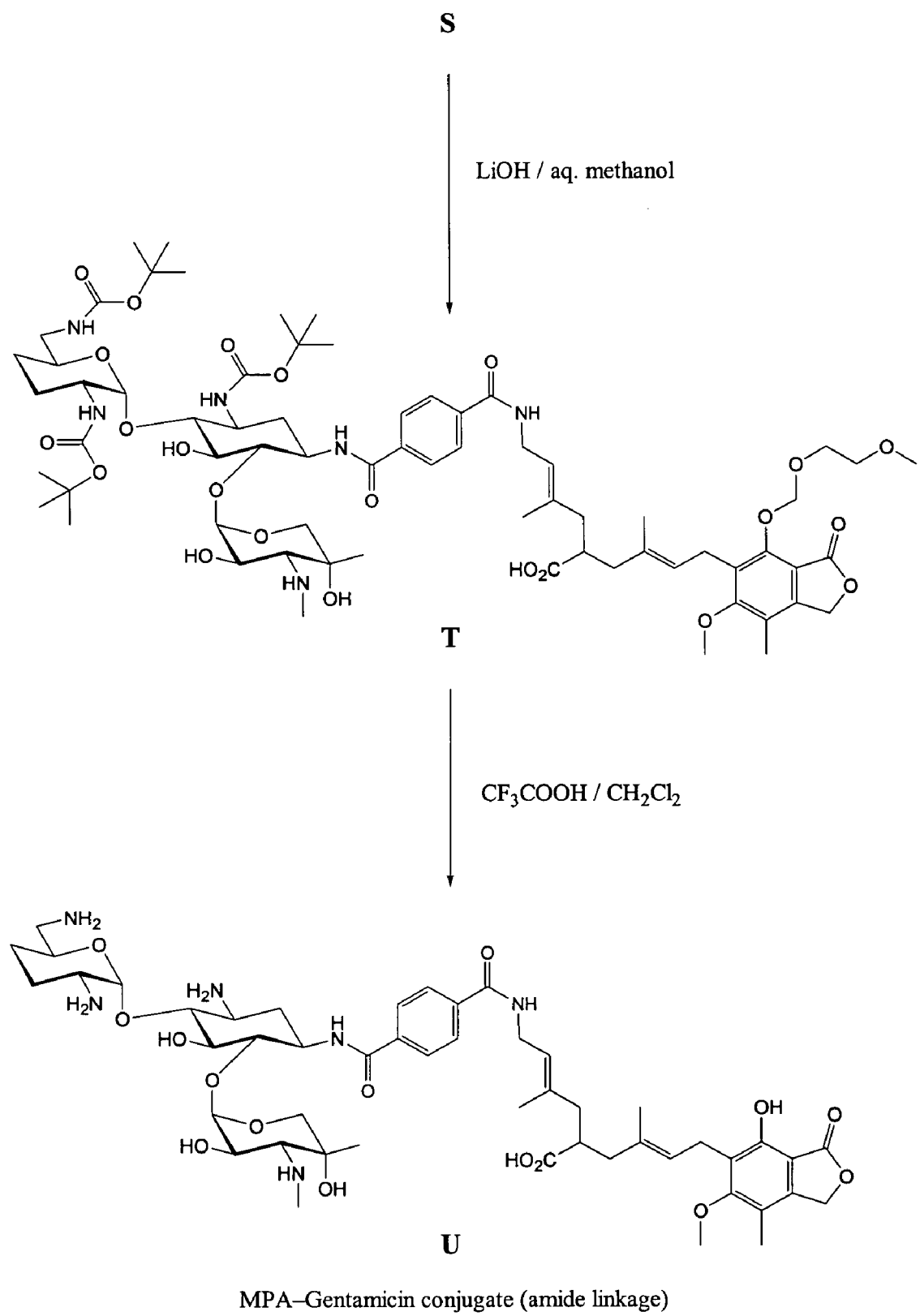
Figure 25:
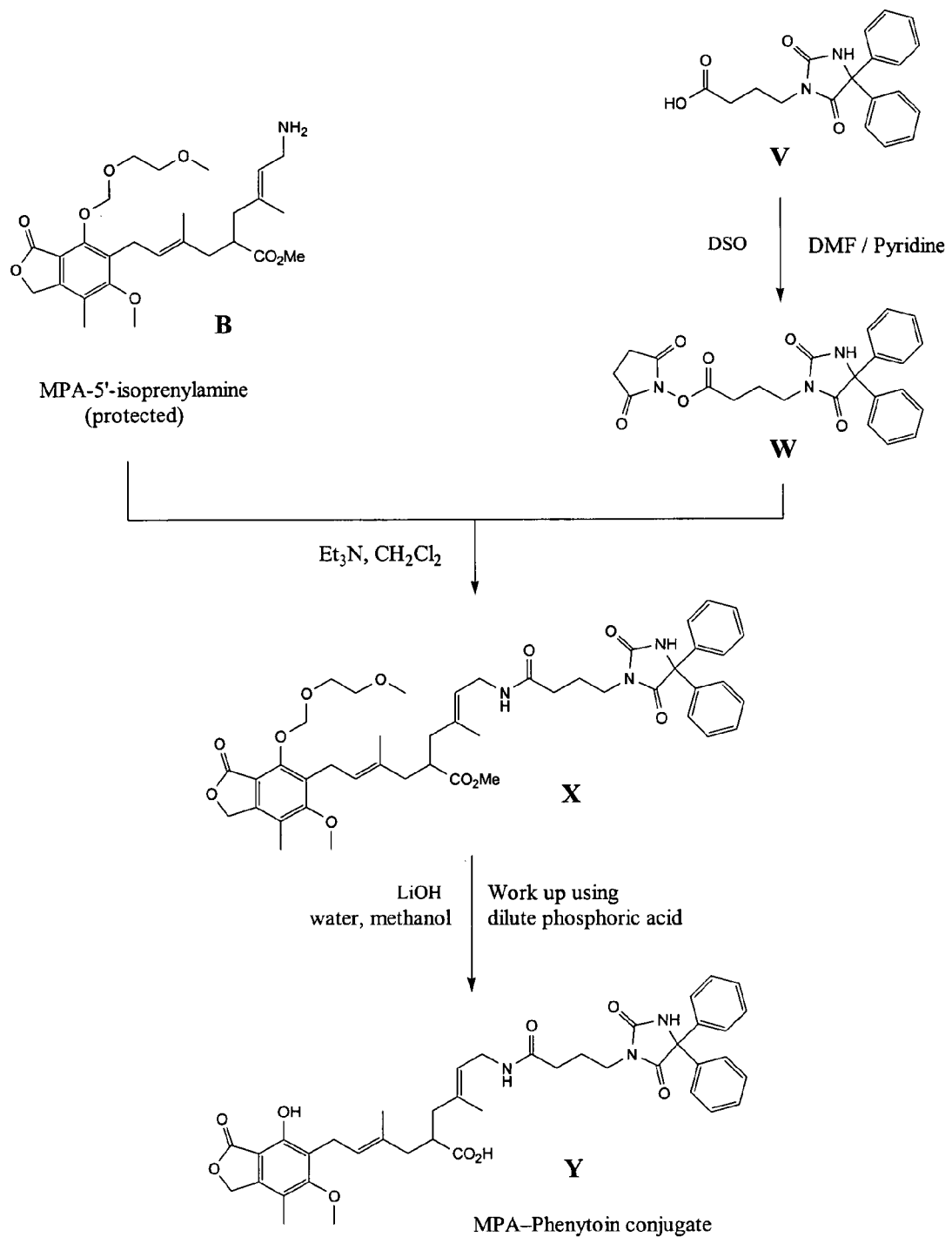
FIG. 25 illustrates the preparation of 5'-[(phenytoin-3-butyramido)-isoprenyl]-MPA conjugate (Y) as described in Examples 55, 56 and 57.
Figure 26:
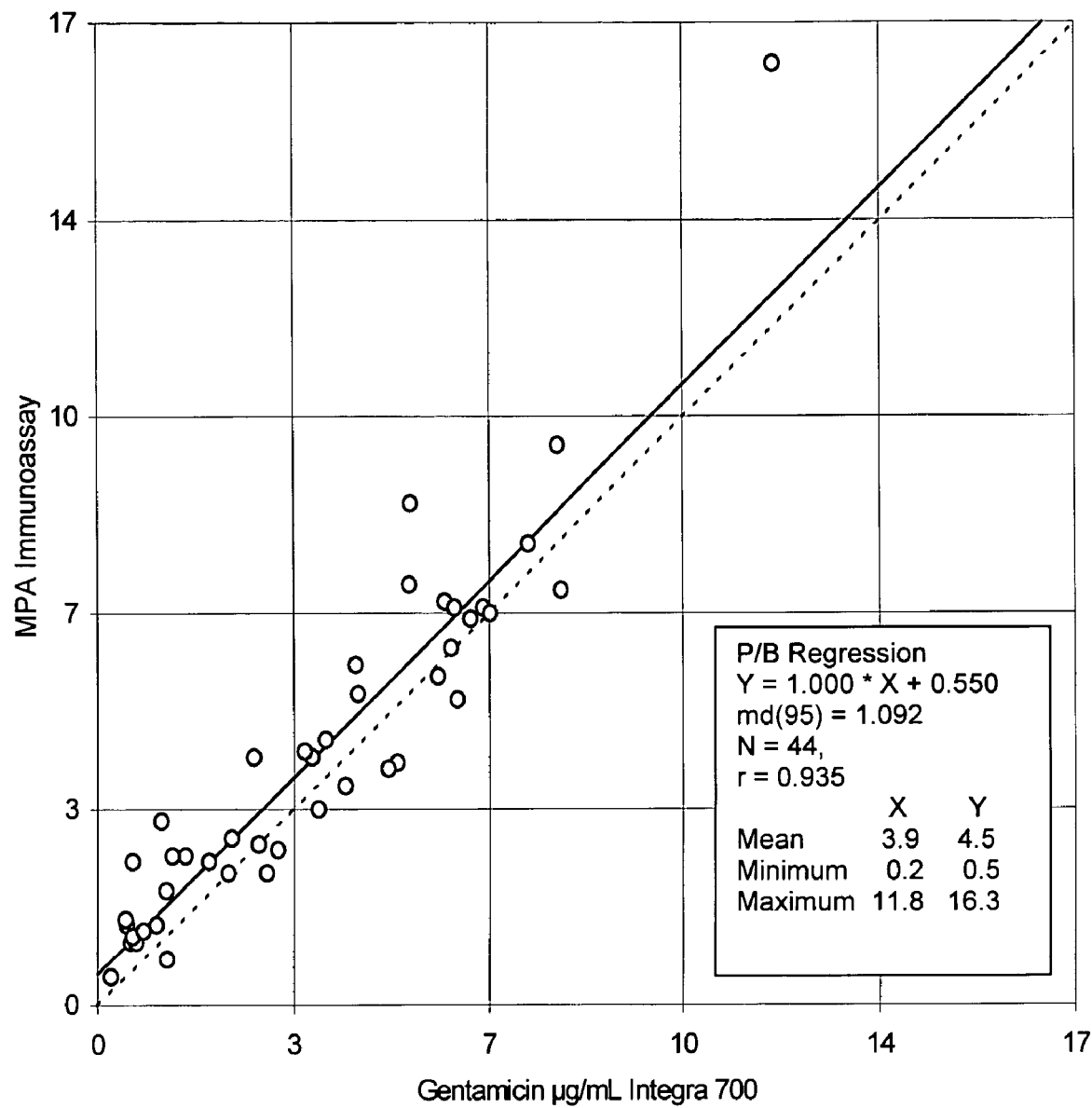
FIG. 26 illustrates the ability of the assay to quantitate phenytoin in patient samples as compared to a fluorescence polarization method as described in Example 58.
Figure 27:
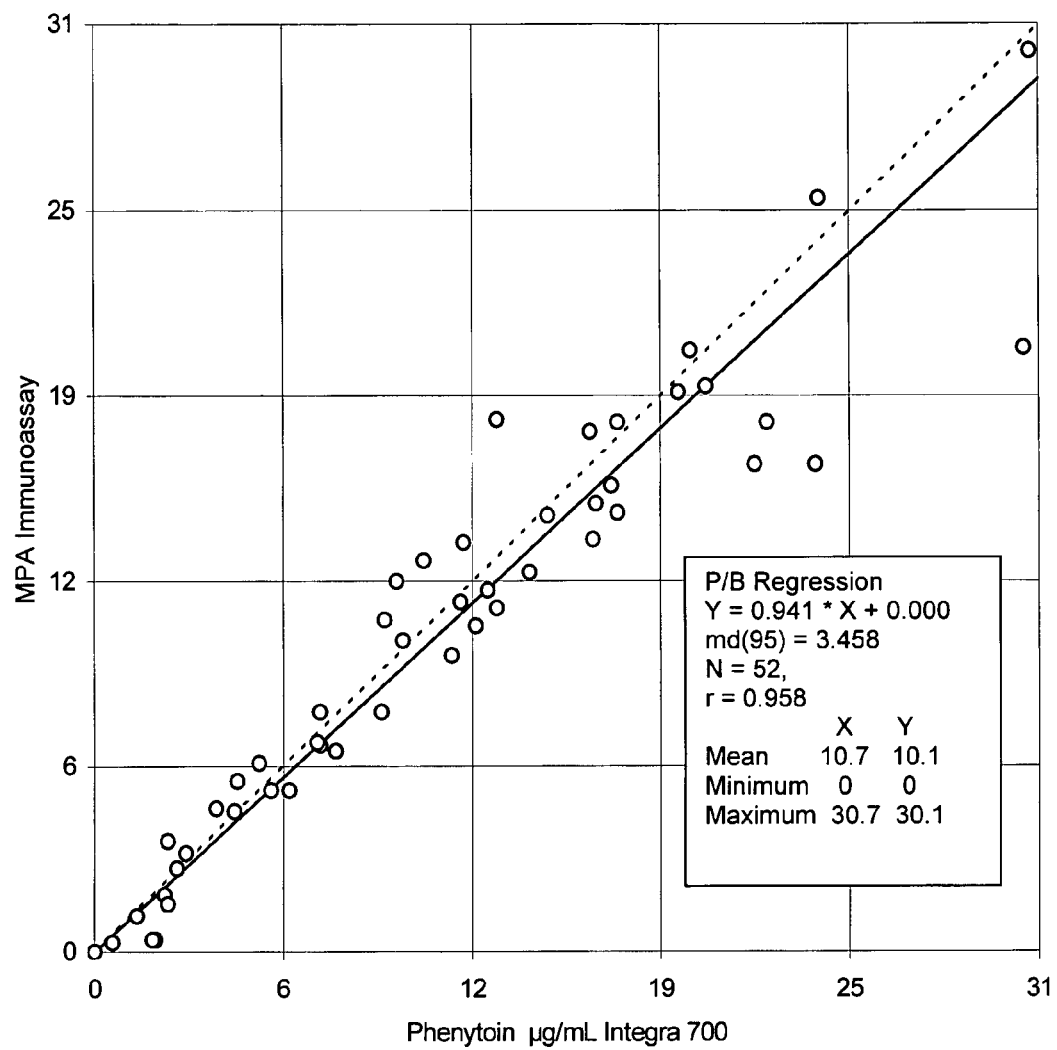
FIG. 27 illustrates the ability of the assay to quantitate gentamicin in patient samples as compared to a fluorescence polarization method as described in Example 58.
Figure 28:
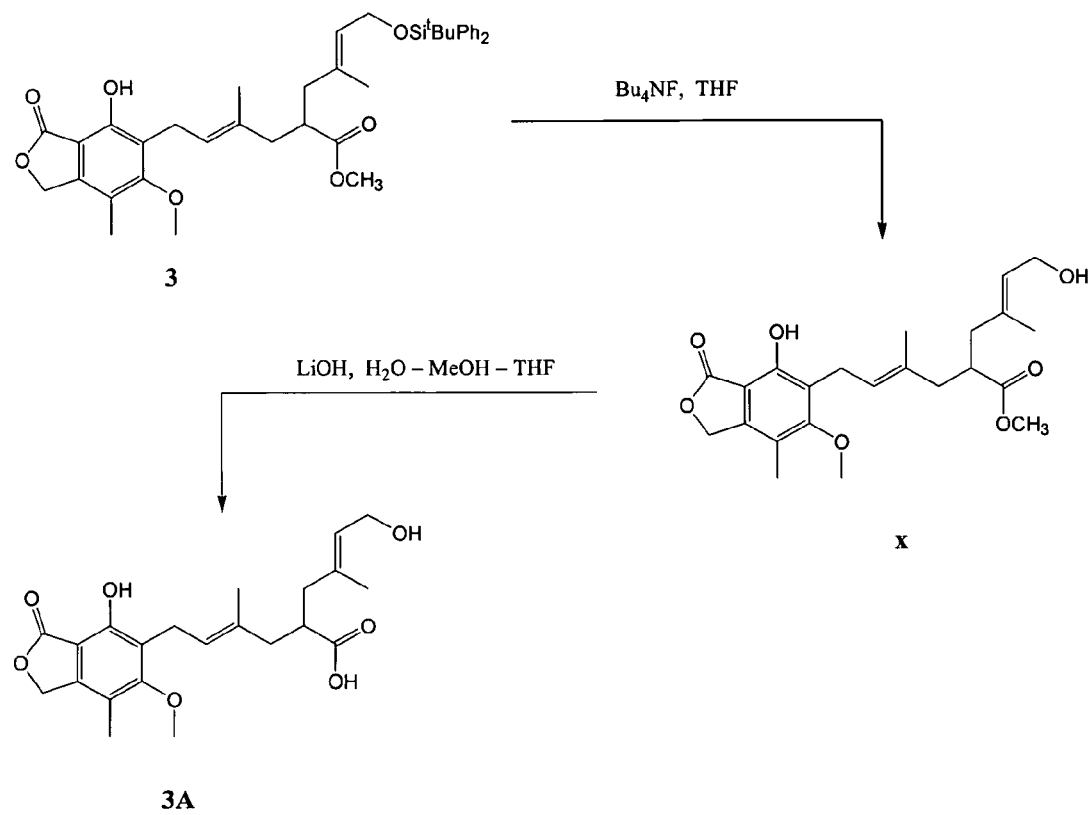
FIG. 28 illustrates the preparation of MPA-isoprenyl alcohol (racemic, 3A) as described in Example 5A.
Figure 29:
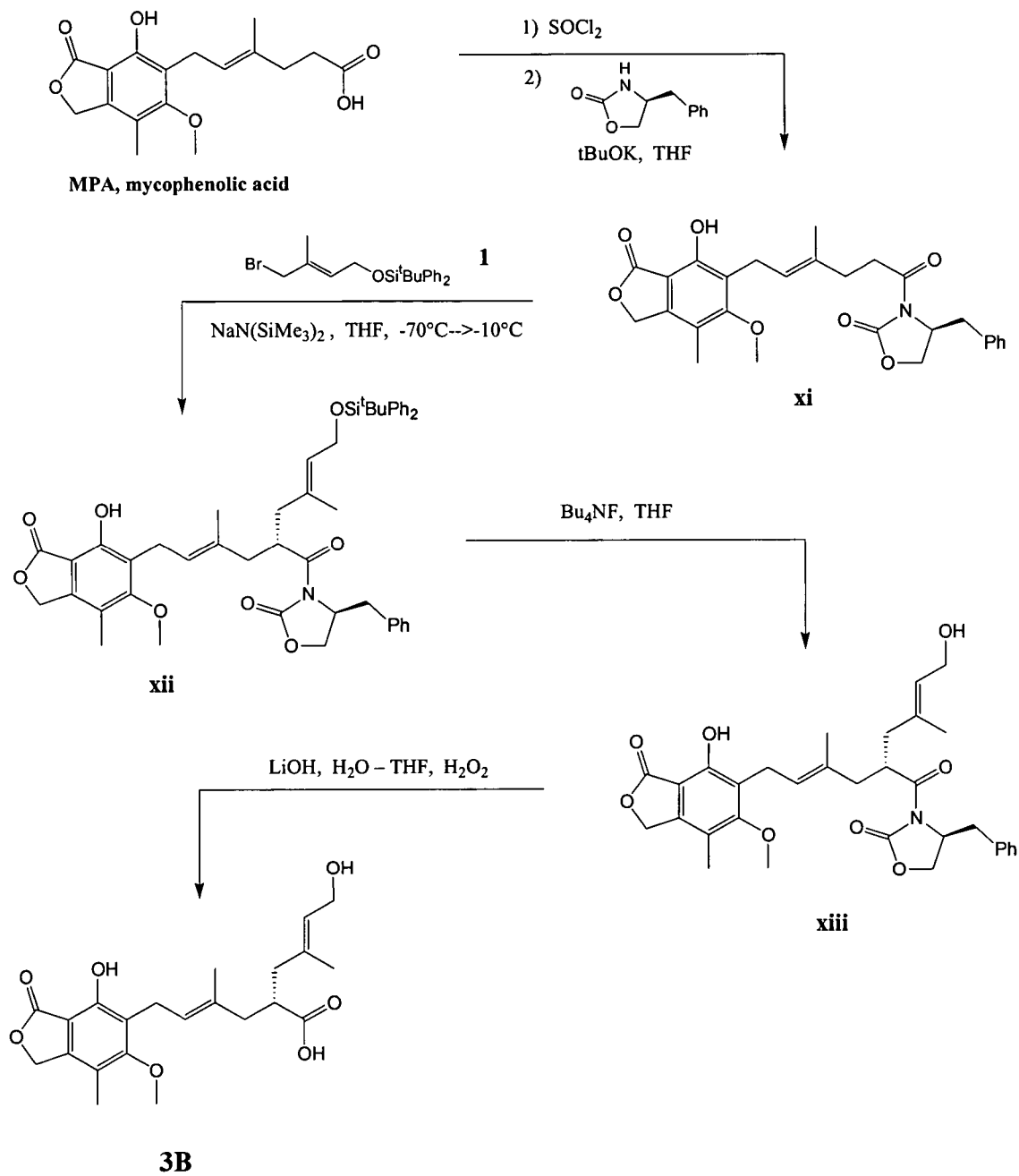
FIG. 29 illustrates the preparation of MPA-isoprenyl alcohol (chiral, R-enantiomer, 3B) as described in Example 5B.

Towards this end, the corresponding MPA-5'-isoprenylamine analog could be generated by a Mitsunobu reaction on the 5'-isoprenyl[OH]-MPA[OMEM] (5) derivative discussed above. Isomerization around the double bond was observed when we used a multi-step conversion sequence, e.g. conversion of the alcohol to the bromide, followed by conversion to the azide and hydrolysis to the amine. However, one-step reaction of the MPA-5'-isoprenyl alcohol with triphenylphosphine and phthalimide in the presence of an activating agent/mediator such as diisopropyl azodicarboxylate (DIAD) provided the desired MPA phthalimide, which upon treatment with methylamine in ethanol gave MPA-5'-isoprenylamine (B), as shown in FIG. 19. Using this amine, the MPA-phenytoin conjugate (Y) and the MPA-gentamicin conjugate (U) both containing the stable amide linkage were prepared as described in FIGS. 25 and 24*a,b* respectively.

Figure 21:
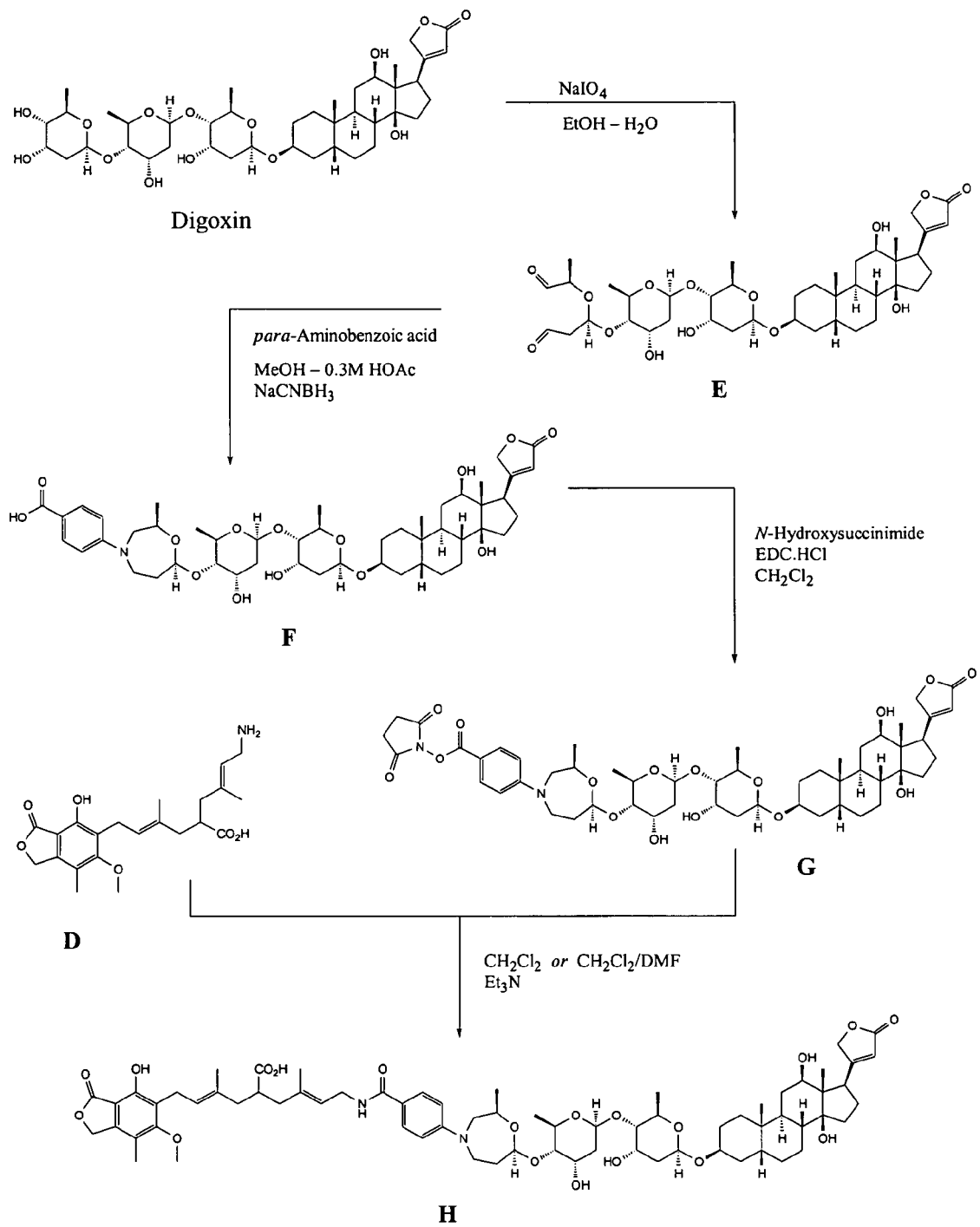
FIG. 21 illustrates the preparation of 5'-[[[[(digoxin(1,4-oxazepin))-4-yl]-phenyl-4-carbonyl]amino]isoprenyl]-MPA conjugate (H) as described in Example 47.

The MPA-digoxigenin derivatives (i.e. wherein the sugar moieties of digoxin are missing) as shown in FIGS. 11, 12, 13 and 14 contain amide linkages and were synthesized from corresponding digoxigenin-amine derivatives and an MPA 5'-carboxyalkyl analog. In contrast, the digoxin oxazepin analog (G), as shown in FIG. 21, allows for the use of the MPA-5'-isoprenylamine described above to form MPA-digoxin conjugate (H), also with an amide bond, as well as keeping the sugars of digoxin present. The corresponding digitoxin oxazepin analog (K) allows for the synthesis of the MPA-digitoxin conjugate (L) also with the sugars present.

Figure 20:
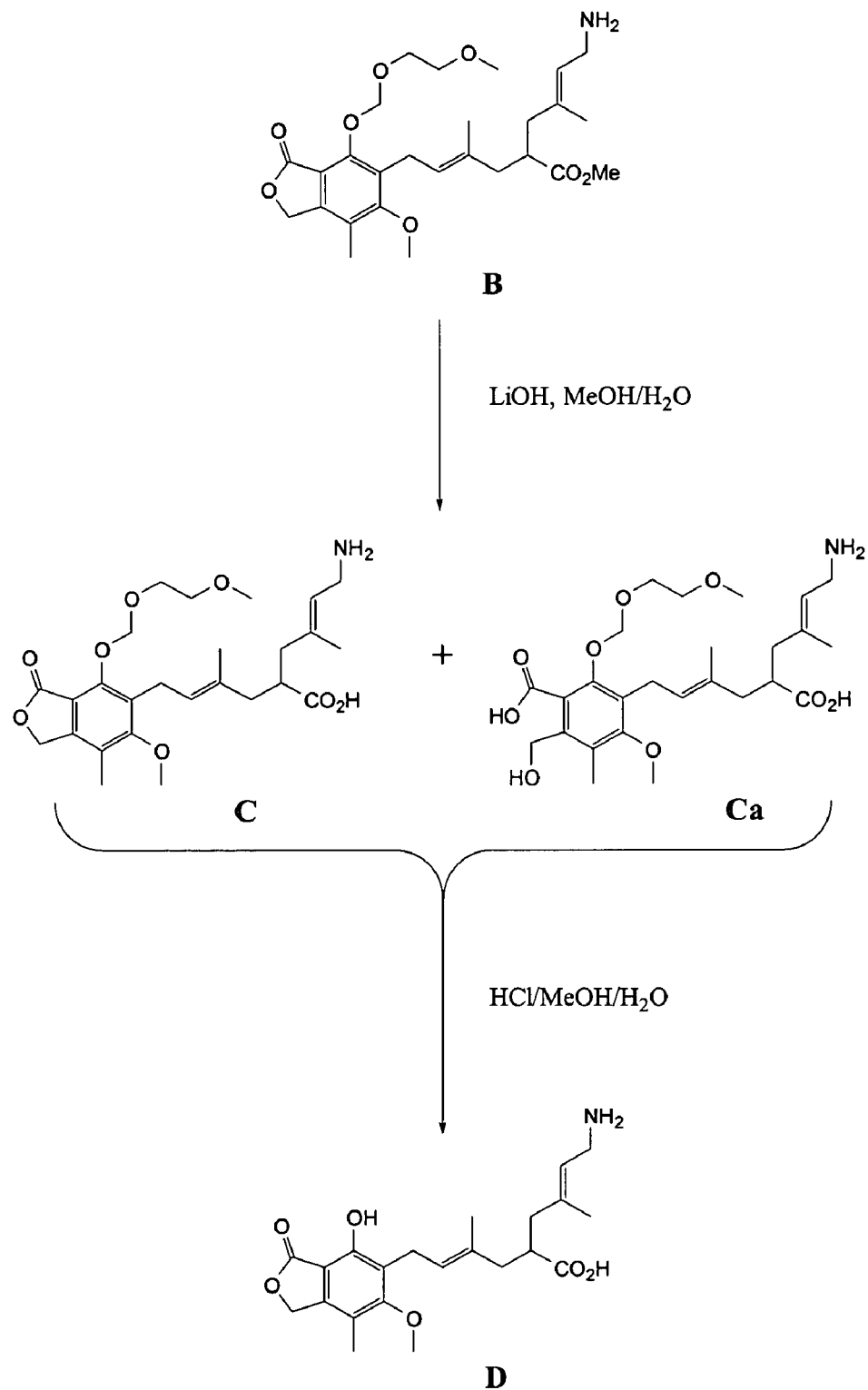
FIG. 20 illustrates the deprotection of MPA[OMEM]-5'-isoprenylamine methyl ester (B) to MPA-5'-isoprenylamine (D) via MPA[OMEM]-5'-isoprenylamine (C) as described in Example 46.
Figure 22:
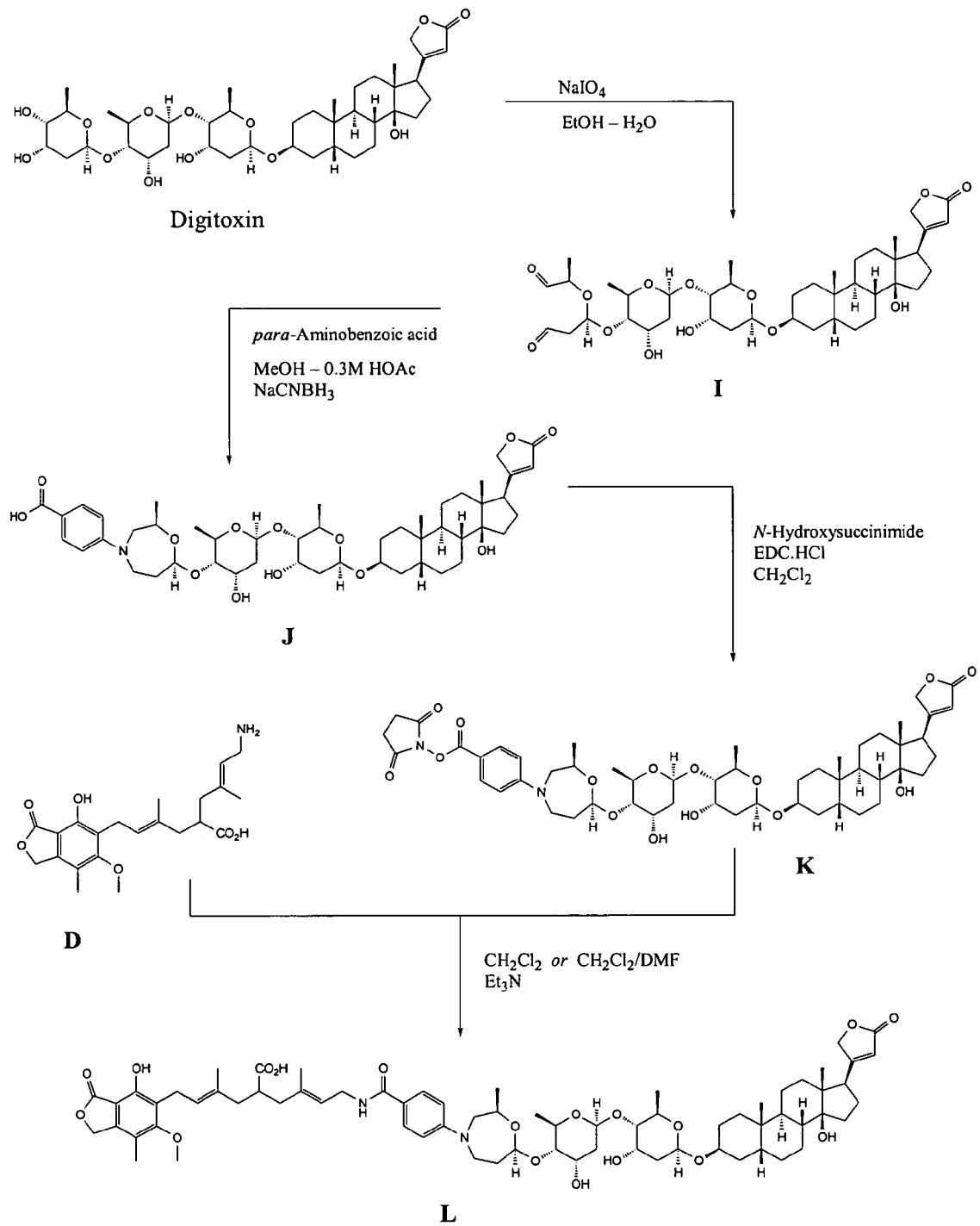
FIG. 22 illustrates the preparation of 5'-[[[[(digitoxin(1,4-oxazepin))-4-yl]-phenyl-4-carbonyl]amino]isoprenyl]-MPA conjugate (L) as described in Example 48.

However, it was found more efficacious to convert the protected MPA amine (B) to the fully deprotected MPA-5'-isoprenylamine (D), as shown in FIG. 20, before reaction with either (G) or (K), and as shown in FIGS. 21 and 22. The causes for this variation were the sensitivity of the various functional groups such as the lactones and the glycosidic bonds, and in particular the sensitivity of the digoxin or digitoxin sugars toward rupture at the glycosidic bonds especially at the juncture between the C3-position of the steroid nucleus and the first sugar moiety, under mild conditions. As examples, reaction of the protected MPA amine (B) with (G) gave the corresponding protected conjugate possessing the MEM and methyl ester groups which, on mild base treatment (hydrolysis of the ester), gave material with one or both lactone groups opened; while reaction of the partially deprotected MPA amine (C) with (G) gave the corresponding partially protected conjugate possessing the MEM group which on mild acid treatment (TFA in $CH_2Cl_2$) gave material with the digoxigenin steroid nucleus cleaved off but with the MEM group still largely present.

These oxazepin analogs (G) of digoxin, and (K) of digitoxin,, as well as the precursor acids (F) and (J) respectively, in and of themselves are useful substances with advantages over other known analogous oxazepin analogs of the two drugs. In particular, the incorporation of the aminobenzoate moiety endows the molecule with substantial UV absorbance at wavelengths longer than 300 nm, which prior art substances do not have. This allows for easy visualization and identification/quantification of conjugates using these new derivatives, such as in compounds with other UV absorbance bands, or in many protein or polypeptide conjugates where the typical characteristic UV absorbance peak is at, e.g., 280 nm, because the UV absorbance due to the digoxin or digitoxin analog is separated from and at longer wavelength from the UV absorbance due to the protein or polypeptide.

The fully deprotected MPA-5'-isoprenylamine (D) may also be used with any other amine-reactive drug analog, such as but not limited to, drug-NHS esters or other drug-activated ester derivatives, to form MPA-drug conjugates with a stable amide linkage. The amino group of the fully deprotected MPA-5'-isoprenylamine (D), being the most nucleophilic amongst the three functional groups present, would under ordinary conditions wherein it is present as the free base react readily with such drug derivatives without significant interference from the other groups. Such an approach allows for the synthesis of MPA-drug conjugates from suitable drug derivatives without any further deprotection steps or chemical manipulations which might be harmful to the integrity of the whole conjugate.

In a similar manner, the protected MPA-5'-isoprenylamine (B), or the partially deprotected amine (C), may be used with any other amine-reactive drug analog, such as but not limited to, drug-NHS esters or other drug-activated ester derivatives, to form MPA-drug conjugates with a stable amide linkage, followed by deprotection to the final Drug-MPA conjugates.

Additionally, as non-limiting examples, either the protected MPA-5'-isoprenyl amine (B), or (C), or the fully deprotected amine (D), all primary amines, may each be converted into the corresponding lower alkyl secondary amine by alkylation at the amino group through methods well-known in the art. These substances may then be used to form yet further MPA-drug conjugates by reaction between these secondary amines with drugs containing a linker with a halogen (for example, Cl or Br or I) as a leaving group, when the drug itself does not contain additional labile groups. In many cases they may also be reacted with other amine-reactive drug analogs, such as but not limited to, drug-NHS esters or drug-isothiocyanates or drug-tosylates and the like, or other drug-activated ester derivatives, to form MPA-drug conjugates. Deprotection of the OMEM and the carboxylic ester groups, or of other protecting groups that may be used or may be present, may then be effected using methods similar to those described in this invention, or by methods readily known to skilled practitioners of the art. In a similar manner, the preceding primary amines (B), (C), or (D) may also be used in an analogous fashion to generate the corresponding MPA-drug conjugates. Other combinations between such MPA amines and drug analogs would be suggested to those skilled in the art.

Finally, MPA-5'-isoprenylthiol may be prepared by conversion of the corresponding isoprenylalcohol to a tosylate or mesylate, optionally followed by substitution with halide, preferably bromide or iodide, to give an MPA-5'-isoprenylhalide. These compounds can be readily converted to the thiol through methods known to one skilled in the art, such as, for example, reaction with thiourea followed by base hydrolysis; or by reaction with thioacetate, preferably as a metal salt, followed by mild base cleavage of the acetyl group.

The inhibition of IMPDH by mycophenolic acid is described by Anderson, J. H. et al., *Journal of Biological Chemistry* 243(18):4762–4768 (1968). Inhibitors of IMPDH are also described in U.S. Pat. Nos. 5,380,879, 5,444,072, 5,493,030, 5,536,747, 5,633,279 and 5,807,876 and in PCT publications WO 94/01105 and WO 94/12184.

The cloning and expression of human IMPDH in *E. coli* has been described by Konno, Y. et al., *J. Biol. Chem* 266(1):506–509 (1991). Collart, F. R. et al., U.S. Pat. No. 5,665,583 (1997) also describe the cloning and expression in *E. coli* of human IMPDH.

Analyte refers to the substance, or group of substances, whose presence or amount thereof in a liquid medium is to be determined and is meant to include any drug or drug derivative, hormone, protein antigen or oligonucleotide.

Antibody, or preferably, receptor, means a specific binding partner of the analyte and is any substance, or group of substances, which has a specific binding affinity for the ligand to the exclusion of other substances.

Ligand means any substance, or group of substances, which behaves essentially the same as the analyte with respect to binding affinity of the antibody for the analyte and is meant to include any drug or drug derivative and isomers thereof, hormone, polypeptide, or nucleotide.

An example of the measurement of a drug would involve the coupling of morphine thiocyanate or cocaine NHS ester derivatives described by Salamone, S. J. et al., U.S. Pat. No. 5,618,926 (1997) to 4'- or 5'-substituted alkyl amino derivatives of mycophenolic acid or MPA derivatives or any uncompetitive inhibitors of IMPDH to measure morphine or cocaine in unknown samples. Plotting the concentration of drug versus the IMPDH activity can produce a quantitative assay.

The present invention can also be used in molecular diagnostics to determine the presence of a specific target DNA or RNA. In this case a nucleotide-mycophenolic acid conjugate (N-MPA) would be able to inhibit IMPDH when it is not part of an oligonucleotide chain. Once the N-MPA is incorporated into an oligonucleotide chain, the ability of the mycophenolic acid portion of the conjugate to inhibit IMPDH would be modulated.

The N-MPA conjugate can be prepared according to procedures that are well known in the art. The nucleotide can be derivatized through the sugar, base or phosphate moiety in such a way to allow it to be a substrate for enzymes that synthesize oligonucleotides. For example a derivatized nucleotide base could have a tether containing an electrophile or nucleophile. This derivative can then be reacted with an appropriately derivatized MPA molecule to form an N-MPA conjugate.

The assay would be performed by adding a percentage of the N-MPA conjugate to the nucleotide mixture that would be used to synthesize the oligonucleotide. A sample would be added along with the enzymes, and probes used to polymerize the oligonucleotide, DNA and RNA polymerases would be examples of such polymerizing enzymes. At the end of the polymerizing step, IMPDH along with the appropriate IMPDH reactants would be added. If the sample does not contain the target oligonucleotide sequence, then oligonucleotide synthesis would not proceed and the N-MPA would be free to inhibit IMPDH. If the target sequence is present in the sample, then the N-MPA would be incorporated into the oligonucleotide and less N-MPA conjugate would be available to inhibit the IMPDH. The concentration of free N-MPA would be inversely proportional to the IMPDH activity. The more the free N-MPA is depleted, the higher the IMPDH activity will be.

This assay can be used on both a qualitative and quantitative basis to determine the presence of particular target DNA or RNA molecules. The amount of target present in the sample will be proportional to the IMPDH activity.

Modulation of IMPDH activity by MPA derivatives can also be applied to the detection of protein antigens. A short polypeptide which represents the epitope or mimitope of a larger antigen can be derivatized, according to methods known in the art, to contain a group that can be attached to an appropriately derivatized MPA molecule to form a polypeptide-MPA conjugate (PP-MPA). See Amerongen, A. V. et al., *Peptide Research* 5(5):269–274 (1992).

The assay is performed by mixing a clinical sample with PP-MPA, antibody or appropriate binding partner selective for the antigen of interest, IMPDH and the appropriate reactants used in the IMPDH assay. If the sample does not contain the antigen, the PP-MPA conjugate will be bound by the antibody and will not be available to inhibit IMPDH. If the sample contains the specific target antigen for which the assay is designed, the PP-MPA conjugate will compete with the antigen for the limited antibody present. The amount of inhibition of IMPDH is proportional to the amount of free antigen present in the sample. A quantitative assay can be generated by plotting the concentration of antigen versus the amount of IMPDH activity. The amount of antigen present will be inversely proportional to the amount of IMPDH activity.

A more complete understanding of the present invention will be obtained by reference to the following non-limiting examples.

| Abbreviations used: | |
|---|---|
| ACES | N-[2-acetamido]-2-aminoethanesulfonic acid |
| DADOO | 1,8-diamino-3,6-dioxa-octane 2,2'-(ethylenedioxy)bis-ethylamine |
| DCC | 1,3-dicyclohexylcarbodiimide |
| DMF | N,N-dimethylformamide |
| DMPU | 1,3-dimethyl-3,4,5,6-tetrahydro-2(1H)-pyrimidinone |
| EDC | 1-ethyl-3(3-dimethylaminopropyl)carbodiimide |
| HMPA | hexamethylphosphoramide |
| MEM | 2-methoxyethoxymethyl |
| NaHMDS | sodium bis(trimethylsilyl)amide |
| NHS | N-hydroxysuccinimide |
| RP-HPLC | reverse phase high-performance liquid chromatography |
| TAPSO | 3-[N-tris-(hydroxymethyl) methylamino]-2-hydroxy-propanesulfonate, Na |
| TBAF | tetrabutylammonium fluoride |
| TBDPS | tert-butyldiphenylsilyl |
| tBoc | tert-butoxycarbonyl |
| TCEP | tris (2-carboxyethyl) phosphine, hydrochloride |
| THF | tetrahydrofuran |

In the examples that follow, boldface numbers refer to the corresponding structure in the drawings.

Reagents were obtained from either Aldrich Chemical Company, Milwaukee, Wis.; or from Sigma Chemical Company, St. Louis, Mo.; unless otherwise stated.

All solvents were obtained from J. T. Baker, Phillipsburg, N.J., and were of A.C.S. grade or H.P.L.C. grade or better unless otherwise stated.

Triethylamine was obtained from Fluka Chemical Corp. (Cat# 90340; puriss.; ≧99.5%)

Trifluoroacetic acid (TFA) was obtained from Fluka Chemical Corp. (Cat# 91703, for UV-spectroscopy)

Anhydrous pyridine and dimethylformamide (DMF) were obtained from Aldrich Chemical Co., prepackaged in "Sure-Seal™" bottles. All additions/withdrawals and manipulation of anhydrous solvents were performed by syringe/needle.

Tetrahydrofuran (THF) was dried by boiling over and distillation from sodium/benzophenone under argon.

Methylene chloride was dried by boiling over and distillation from calcium hydride under argon.

Column chromatography was performed using flash-grade silica gel from E.M. Science (Cat. #9385-9; Silica gel 60; 230400 mesh ASTM) and under a positive pressure of nitrogen.

Thin layer chromatography (TLC) was performed using silica gel plates obtained from E.M. Science (Cat. #5715-7; 0.025 cm thickness)

Mixed solvents are expressed as volume for volume percentages. For example, 10% MeOH—CHCl$_3$ (or 10% MeOH in CHCl$_3$) is chloroform containing 10% of methanol by volume.

Unless otherwise stated, analytical RP-HPLC analyses were performed on either an Agilent HP1100 LC/MS system; or an Agilent HP 1100 HPLC system, both configured with a diode-array detector and a quaternary pump. The LC/MS analyses were performed with a Vydac 218TP54 column (RP-C18; 300 Å, 5µ) equipped with a Phenomenex guard module (Phenomenex KJO-4282/ C18 ODS 5µ), with the chromatographic stream ported post-column into the MS detector. The MSD utilized was run in ES (+) mode (electrospray; positive mode). The HPLC analyses were performed with a Vydac 218TP54 column (RP-C18, 300 Å, 5µ) equipped with a Vydac 218GK54 guard module.

Unless otherwise stated, Preparative RP-HPLC was performed on a Varian Dynamax (Rainin) system employing two SD 1 titanium head 2000 psi pumps with a Varian Dynamax UV-C variable wavelength detector. Separations were carried out on a modular Varian Dynamax radial compression column (R00083221C; Microsorb 60–8, C18, 250×21.4 mm) equipped with a guard module (R00083221G; C18, 8µ).

Unless otherwise stated, lyophilization of HPLC fractions involved evaporation of the acetonitrile (or other organic co-solvent) under reduced pressure, followed by freezing of the aqueous residue (e.g. using a dry-ice/acetone cooling bath), followed by sublimation of the ice on a lyophilizer in the usual manner.

[1]-NMR spectra were obtained at either 200, 300, or 400 MHz on either Varian or Bruker instruments.

Mass spectra were obtained from the Physical Chemistry/Analytical facilities of Hoffmann-La Roche (Nutley, N.J.), Roche Bioscience (Palo Alto, Calif.), Roche Diagnostics GmbH (Penzberg, Germany), Roche Diagnostics Corp (Indianapolis, Ind.), or from the Nebraska Center for Mass Spectrometry, Dept. of Chemistry, U. of Nebraska (Lincoln, Nebr.).

UV spectra were obtained from Robertson Microlit Laboratories, Madison, N.J. The abbreviation used is: sh, shoulder.

Combustion microanalytical data were obtained from Robertson Microlit Laboratories, Madison, N.J.

EXAMPLE 1

Preparation of Antibody Reagent for Mycophenolic Acid Assay

One liter of an antibody reagent, or first reagent, was prepared as follows. Approximately 800 ml deionized water was dispensed into a container and 6.0 grams of ACES were added and dissolved. The pH was adjusted to 6.0 with 2N NaOH. Then 0.53 grams NAD were added and dissolved completely. Next 10 ml ascites anti-MPA monoclonal antibody was added. Then 0.95 grams sodium azide was added and dissolved, and finally 1.0 gram of SUTTOCIDE A (GAF Chemicals Corp.) was added and dissolved. The volume was adjusted to one liter with deionized water.

TABLE 1

Composition of Antibody Reagent

| Antibody reagent, pH 6.0 Component | Molec. wt. | M | g/l | Function | 150 µl final M |
|---|---|---|---|---|---|
| ACES | 182.2 | 0.0330 | 6.0 | Buffer, NAD stabilizer | 0.0163 |
| NAD | 663.4 | 0.0008 | 0.53 | Enzyme substrate | 0.0004 |

TABLE 1-continued

Composition of Antibody Reagent

| Antibody reagent, pH 6.0 Component | Molec. wt. | M | g/l | Function | 150 µl final M |
|---|---|---|---|---|---|
| Anti-MPA | — | — | 1:100 | Monoclonal antibody | — |
| Na azide | 65.0 | 0.0146 | 0.95 | Anti-microbial preservative | 0.0072 |
| SUTTOCIDE A (50%) | 127.1 | 0.004 | 1.0 | Anti-microbial preservative | 0.004 |

The antibody used was prepared according to the procedure described by Alexander et al. in PCT patent publication WO 96/02004 (1996). Any antibody with specificity for MPA, either monoclonal or polyclonal, may be used in the practice of the present invention. Monoclonal antibodies are generally preferred, however, because of their ease and consistency of production.

EXAMPLE 2

Preparation of Enzyme Reagent for Mycophenolic Acid Assay

One liter of an enzyme reagent, or second reagent, was prepared as follows. Approximately 800 ml deionized water was dispensed into a container and 56.3 grams of NaTAPSO was added and completely dissolved. Then 81.6 grams of sodium acetate-3$H_2O$ were added and dissolved. Next, 1.15 grams of TCEP were added and dissolved. Next 0.319 grams of IMP were added and dissolved, then 2.23 grams of $Na_2$EDTA were added and dissolved. Next 1.0 gram of SUTTOCIDE A was added and dissolved. The volume was adjusted to one liter with deionized water. Approximately 13.4 ml of recombinant human IMPDH-II were added (*E. coli* lysate) and dissolved completely in order to achieve a change in absorbance at 340 nm of $4400 \times 10^{-4}$ over 5 minutes at 37° C. Next 0.002 grams of ligand-inhibitor conjugate (MPA-MPA, Example 42) were added and dissolved.

The procedure used for cloning and purification of IMPDH-II is described in Carr, S. F. et al., *J. Biological Chemistry* 268(36):27286–27290 (1993), the content of which is herein incorporated by reference. Cloning of IMPDH is also described in Collart, F. R. et al., U.S. Pat. No. 5,665,583 (1997). IMPDH from natural sources is not commercially available. Any natural source of IMPDH that is inhibited by MPA, MPA-derivative or uncompetitive inhibitor of IMPDH is also suitable.

Effective amount of reagent components are variable depending on specific needs and may be adjusted by simple laboratory experimentation to meet particular assay requirements.

The ligand-inhibitor concentration was chosen based on the degree of IMPDH inhibition by the ligand-inhibitor with and without specific antibody to the ligand. The maximum difference in percent change in inhibition with and without antibody was chosen for use in immunoassay. It was found that in general, a concentration of inhibitor slightly less than its $IC_{50}$ value and a molar concentration of antibody slightly less than half the molar concentration of ligand-inhibitor produced the maximum difference in percent change in IMPDH inhibition. With two binding sites per antibody, the total number of ligand binding sites was slightly less than the total molar concentration of ligand-inhibitor. The enzyme activity had a slight effect on the IC50 values of the ligand-inhibitor. The lower the enzyme activity, the lower the $IC_{50}$ value of the ligand-inhibitor. This is consistent with Nowak, I. et. al, *Therapeutic Drug Monitoring* 19, 358–360 (1997). Therefore, the IMPDH activity was adjusted to produce the lowest $IC_{50}$ value for the ligand-inhibitor.

TABLE 2

Composition of Enzyme Reagent

| Enzyme reagent, pH 8.0 Component | Molec. wt. | M | g/l | Function | 150 µl final M |
|---|---|---|---|---|---|
| Na TAPSO | 281.3 | 0.2 | 56.3 | Buffer | 0.1 |
| Na acetate-3$H_2O$ | 136.1 | 0.6 | 81.6 | Enzyme stabilizer-reduces enzyme aggregation | 0.3 |
| TCEP | 286.65 | 0.004 | 1.15 | Enzyme stabilizer-reduces cysteine sulfhydryl groups | 0.002 |
| $Na_2$ IMP | 392.2 | 0.0008 | 0.319 | Enzyme substrate | 0.0004 |
| $Na_2$EDTA | 372.2 | 0.006 | 2.23 | Enzyme stabilizer-chelates heavy metals, maintains reduced cysteine sulfhydryls | 0.003 |
| SUTTOCIDE A (50%) | 127.1 | 0.004 | 1.0 | Anti-microbial preservative | 0.004 |
| IMPDH-II | — | — | — | Enzyme | — |
| MPA-MPA | 581 | $3.4 \times 10^{-6}$ | 0.002 | Ligand-inhibitor | $1.7 \times 10^{-6}$ |

EXAMPLE 3

Measurement of Mycophenolic Acid

Human plasma samples spiked with mycophenolic acid were assayed for MPA using the method of the present invention. An HITACHI 717 analyzer (Roche Diagnostics Corp., Indianapolis) was programmed to dispense 3 µl of sample and 150 µl of antibody reagent into a 37° C. cuvette, which were then mixed and incubated for 5 minutes after which time 150 µl of enzyme reagent was added and mixed.

The difference in absorbance at 340 nm was calculated from the initial addition of enzyme reagent to 5 minutes following enzyme reagent addition.

TABLE 3

IMPDH activity as a function of ligand-inhibitor conjugate, antibody and analyte concentration

| 3 μl Sample (MPA μg/ml) | 150 μl Antibody Reagent (+/− anti-MPA) | 150 μl Enzyme Reagent (+/− MPA-MPA) | $\Delta A \times 10^{-4}$ @ 340 nm |
|---|---|---|---|
| A 0 | − | − | 4338 |
| 5 | − | − | 1939 |
| 10 | − | − | 541 |
| B 0 | − | + | 1666 |
| 5 | − | + | 557 |
| 10 | − | + | 214 |
| C 0 | +(1:100) | + | 3109 |
| 5 | +(1:100) | + | 2671 |
| 10 | +(1:100) | + | 2135 |
| D 0 | +(1:1000) | + | 1957 |
| 5 | +(1:1000) | + | 804 |
| 10 | +(1:1000) | + | 304 |
| E 0 | +(1:100) | − | 4330 |
| 5 | +(1:100) | − | 4075 |
| 10 | +(1:100) | − | 3667 |

Table 3 shows IMPDH activity as a function of ligand-inhibitor conjugate (MPA-MPA), MPA antibody and mycophenolic acid analyte (MPA) concentration. The data indicates that the ligand-inhibitor conjugate possesses useful inhibitory characteristics necessary for a homogeneous immunoassay; that is, the ligand-inhibitor conjugate is bound by both IMPDH and its specific antibody, and this binding is a mutually exclusive event. With sample set A, the reagents contained no antibody or ligand-inhibitor and produced maximum IMPDH activity. With sample set B, the enzyme reagent contained ligand inhibitor and was used to show the effect of ligand inhibitor on IMPDH activity. Sample set C was set up to show the modulation of IMPDH activity by MPA when both antibody and ligand-inhibitor are present. In Sample set D, not enough antibody was present in the antibody reagent to bind MPA or MPA-MPa conjugate and shows the effect of insufficient antibody concentration. In Sample set E, sufficient antibody is present to bind most of the MPA and shows the effect of antibody binding on MPA alone. Compare these results with those results obtained without antibody observed with sample set A.

EXAMPLE 4

Preparation of bromo-isoprenyl linker, MPA-methyl ester and 3-β-amino-digoxigenin Bromo-isoprenyl linker (1) was prepared according to the procedure published by Stephanie E. Sen and Gregory J. Ewing in *J. Org. Chem.* 62,3529–3536(1997).

MPA methyl ester (2) was prepared according to the procedure published by William A. Lee, Leo Gu, Andrew R. Miksztal, Nancy Chu, Kwan Leung and Peter H. Nelson in *Pharmaceutical Research* 7,161–166 (1990).

3-β-Amino-digoxigenin was prepared according to the procedure published in *Bioorganic & Medicinal Chemistry Letters* 9,771–774 (1999).

EXAMPLE 5

Preparation of 5'-isoprenyl[OTBDPS]-MPA methyl ester (3)

A solution of 4.02 ml (401 mmol) of sodium bis (trimethylsilyl) amide, 1M solution in tetrahydrofuran (THF), was cooled in a dry ice/acetone bath under argon atmosphere. To this reaction mixture was added dropwise a solution of 600 mg (1.79 mmol) of MPA methyl ester (2) in 7 ml of anhydrous THF. The resulting solution was allowed to stir at −78° C. for 30 minutes and a solution of 84 mg (0.46 mmol) of hexamethylphosphoramide (HMPA) in 2 ml of THF was added. The reaction mixture was allowed to stir for 15 minutes at −78° C. and a solution of 840 mg (2.08 mmol) of bromo-isoprenyl linker (1) in 2 ml of THF was added dropwise. The dry ice bath was removed and the reaction was allowed to slowly warm up to room temperature over a period of 20 minutes. The reaction mixture was quenched with 5 ml of saturated ammonium chloride. To the reaction mixture 100 ml of water was added and extracted with 200 ml of ethyl acetate. The organic layer was separated and the aqueous part was re-extracted with ethyl acetate (3×100 ml). The combined organic part was washed with 100 ml of brine, dried ($Na_2SO_4$) and concentrated. The crude product was purified by silica gel column chromatography using 20% ethyl acetate in hexane to give 501 mg (43%, 0.76 mmol) of 5'-isoprenyl[OTBDPS]-MPA methyl ester (3). $^1$H-NMR compatible. LR-FAB MS: m/z 656

EXAMPLE 5A

Preparation of MPA-isoprenyl Alcohol (Racemic, 3A)

To a solution of 180 mg (0.27 mmol) of 3 in 18 mL of freshly distilled THF was added 760 μL of 1M solution of tetrabutylammonium fluoride at 0° C. and the resulting solution was allowed to stir at 0° C. for 1 h and at room temperature for 18 hours. To the reaction mixture 12 mL of 0.5 M HCl solution was added and then concentrated to remove THF as much as possible. To the residue 50 mL of water was added and this was extracted with 3×125 mL of ethyl acetate. The combined ethyl acetate layer was washed with 2×100 mL of water, dried (anh. $Na_2SO_4$) and concentrated. The residue was purified by silica gel flash column chromatography using 80% ethyl acetate in hexane to give 85 mg (0.20 mmol, 74%) of x.

To 34 mg (0.081 mmol) of x was added 470 μL freshly distilled THF and 470 μL of methanol followed by 72 mg of lithium hydroxide dihydrate in 1 mL of water. The reaction mixture was allowed to stir at room temperature 18 hours and concentrated under reduced pressure. This was diluted with 20 mL of water and pH was adjusted to 6 using phosphoric acid. The aqueous layer was extracted with 3×20 mL of chloroform. The organic layers were combined, dried ($Na_2SO_4$) and concentrated under reduced pressure. The residue was purified by silica gel column chromatography using 40% methanol in ethyl acetate to give 10 mg (0.024 mmol, 31%) of 3A as white solid. $^1$H-NMR is compatible. LR-FAB MS: M+Na 427.

EXAMPLE 5B

Preparation of MPA-isoprenyl Alcohol (Chiral, R-enantiomer) 3B

The MPA-oxazolidinone imide (xi) was made from mycophenolic acid (MPA) by the method of Rohloff et al. (J. C. Rohloff, J. O. Gardner and R. W. Towne, *Tetrahedron Lett.*, 1995, 36(43), 7803–7806).

An oven-dried kjedahl-type flask was charged with a solution of sodium hexamethyldisilazide (Aldrich; 0.876 mL of a 1 M solution in THF) and the flask and contents cooled to −78° C. (dry-ice/acetone bath) under argon with stirring for 10 min. While maintaining cooling, a solution of the MPA-oxazolidinone (xi, 200 mg, 0.417 mmol) in dry THF (1.5 mL total) was added dropwise by syringe and, after 10 min, dry hexamethylphosphoramide (HMPA, 0.10 mL; distilled from calcium hydride) was added. After 20 min a solution of the bromo-isoprenyl linker (1, 202 mg, 0.50 mmol) in dry THF (1 mL) was added. After stirring at −78° C. for a few minutes the reaction was allowed to warm up to 10° C. over 3.5 hours. TLC analysis indicated consumption of starting material and one major product together with small amounts of others. The reaction was quenched with sat. aq. ammonium chloride and acidified with a little 0.1 N HCl, extracted twice with ethyl acetate (EtOAc), the organic layers washed with 0.1 N HCl, water, half-sat. aq. NaCl, sat. aq. NaCl, dried ($Na_2SO_4$), filtered and evaporated to give 378 mg of a solid. The material was purified by column chromatography on silica gel (50 g) prepacked in 30% EtOAc-hexane, eluting with the same solvent followed by 50% EtOAc-hexanes. Fractions containing the major product were combined and evaporated to give the product (xii, 103 mg, 31%), assigned as the R-isomer by analogy to the literature (Rohloff et al., vide supra). $^1$H-NMR indicated the desired product, with traces of a non-MPA related (by UV) impurity. RP-HPLC [C18: Vydac218TP54; chiral column: Chiralcel® OD™-RH (Chiral Technologies Inc., Exton, Pa., and Daicel Chemical Industries, Japan)] indicated one apparent product isomer.

In another similar experiment, but using dimethyltetrahydropyrimidinone (DMPU) in place of HMPA, the reaction mixture after work-up as before was purified by column chromatography on silica gel (eluting with 15%, then 30% EtOAc-hexanes), followed by preparative TLC (20×20 cm×0.025 cm silica thickness; eluting with EtOAc-hexanes-MeOH (20–80–2)), then followed by RP-HPLC [Chiralcel OD-RH, multiple runs, isocratic 80:20 acetonitrile/water (0.1% $CF_3COOH$), 0.5 mL flow rate] to give purified product (xii) as a solid after lyophilization. $^1$H-NMR: compatible and identical to the previous spectrum. LR(+)FAB MS: M+Na 824, M−H 800, M−$C_4H_9$ 744. HR(+)ES MS: Calc M+Na 824.3589, Observed 824.3600.

To a stirring solution of (xii, 63 mg) in dry THF (3 mL) under argon and cooled in an ice-water bath was added a solution of tetrabutylammonium fluoride (TBAF) in THF (Aldrich; 300 µL of a 1M solution; ~4 mol. eq.). After 2 hours the reaction was allowed to warm up to room temperature, following by TLC analysis, which showed consumption of starting material was almost complete and unchanged after 4.5 hours. The reaction was concentrated under reduced pressure, the residue partitioned between EtOAc and 0.1 N HCl, the organic washed with 0.1 N HCl, water, sat. aq. NaCl, dried ($Na_2SO_4$), filtered and evaporated to dryness. The residue was purified by preparative TLC (20×20 cm×0.025 cm silica thickness), eluting with $CHCl_3$-hexanes-MeOH (50–50–5), to give, from the main product band, the product (xiii, 24 mg, 55%) as a solid/glass. $^1$H-NMR: compatible.

In another experiment, treatment of ~10 mg of (xii) with TBAF in THF in a similar manner to that described above and work-up in a similar manner gave material which was purified twice by preparative TLC ($1^{st}$ plating: eluting with 50% EtOAc-hexanes; $2^{nd}$ plating:eluting with 60% EtOAc-hexanes) to give, from the main band, purified (xiii, 3 mg). $^1$H-NMR: compatible, identical to the previous spectrum. Chiral RP-HPLC (Chiralcel OD-RH): apparent one isomer peak. LR(+)FAB MS (matrix: 3-NBA+Na): M+Na 586, M−H+2Na 608. HR(+)FAB MS: Calc M+Na 586.2417, Observed 586.2410.

To a solution of (xiii, 15 mg, 0.0266 mmol) in dry THF (2 mL) cooled in an ice-water bath was added a solution of lithium hydroxide (4.5 mg, ~4 mol. eq.) in water (0.24 mL) containing hydrogen peroxide (Sigma; 16.3 µL of a 30% weight/weight solution in water, equivalent to ~5.4 mg actual substance, ~6 mol. eq.). The reaction was stirred under argon while maintaining cooling for 2 hours, then allowed to warm up to room temperature overnight. RP-HPLC analysis indicated the reaction was complete. The THF was removed under reduced pressure and the residue partitioned between EtOAc and 0.1 N HCl with a small amount (spatula-tip) of sodium sulfite added in. The mixture was shaken well, the phases separated, the organic washed with 0.1 N HCl, water, sat. aq. NaCl, dried ($Na_2SO_4$), filtered and evaporated to dryness. The residue was purified by preparative TLC (20×20 cm×0.025 cm silica thickness), eluting with 10% MeOH—$CHCl_3$, to give from the main product band the desired product (3B, 8 mg, 74%) as a collapsing off-white foam. $^1$H-NMR: compatible. LC/MS: M+Na 427.1, M−OH 387.1.

EXAMPLE 6

Preparation of 5'-isoprenyl[OTBDPS]-MPA[OMEM] methyl ester (4)

A solution of 240 mg (0.36 mmol) of (3) in 5 ml of dry dichloromethane was cooled in an ice-bath. To the reaction mixture was added 76 µl (0.433 mmol) of N,N-diisopropylethylamine followed by 42 µl (0.36 mmol) of 2-methoxyethoxymethyl chloride. The mixture was allowed to stir in an ice-bath for 1 hour and room temperature for 18 hours. The mixture was diluted with 15 ml of dichloromethane. The organic layer was washed with 3×20 ml of water, dried ($Na_2SO_4$) and concentrated. The crude product was purified by silica gel column chromatography using 60% hexane in ethyl acetate to give 175 mg (0.23 mmol, 64%) of (4).

EXAMPLE 7

Preparation of 5'-isoprenyl[OH]-MPA[OMEM] methyl ester (5)

A solution of 1.09 g (1.46 mmol) of (4) in 40 ml of THF was cooled at 0° C. To this cooled solution was added 4.37 ml (4.35 mmol) of tetrabutylammonium fluoride (1M solution in THF) under argon atmosphere. The reaction mixture was allowed to stir at 0° C. for 1.5 hours and 1 hour at room temperature. The reaction mixture was quenched with 5 ml of water and was concentrated. The reaction mixture was diluted with 75 ml of dichloromethane and washed with 3×75 ml of water, dried ($Na_2SO_4$) and concentrated. The crude product was purified by silica gel column chromatography using 80% ethyl acetate in hexane to give 408 mg (0.806 mmol, 55%) of (5). $^1$H-NMR compatible. LR-FAB MS: m/z 506

EXAMPLE 8

Preparation of L-thyroxine[N-tBoc] (6)

To a magnetically stirred mixture of 4.5 g (5.8 mmol) of L-thyroxine, 18 ml DMF, 5.85 ml of 1N NaOH, 495 mg of $NaHCO_3$ and 18 ml of water. To this suspension was added 1.28 g (5.8 mmol) of di-t-butyl dicarbonate in 18 ml of dimethylformamide. The resulting reaction mixture was allowed to stir for 4 hours and then concentrated under reduced pressure at room temperature. To the residue 45 ml of methanol was added and the undissolved material was filtered off. To the filtrate 1N HCl (20 ml) was added until the precipitation was complete. The solid was filtered and air-dried to give 4.2 g (4.78 mmol, 82%) of L-thyroxine (N-tBoc, 6).

EXAMPLE 9

Preparation of L-thyroxine(N-tBoc)-amidoethyleneamine (7)

To 500 mg (0.57 mmol) of L-thyroxine(N-tBoc, 6) was added 15 ml of anhydrous DMF followed by 149 mg (1.29 mmol) of N-hydroxysuccinimide and 283 mg 1.47 mmol) of 1-ethyl-3-(3-dimethylamino-propyl)carbodiimide. The mixture was allowed to stir at room temperature 3 hours. This activated ester was used in situ in the following step.

To 5.5 ml of anhydrous pyridine was added 1.5 ml (22 mmol) of ethylenediamine. The mixture was allowed to stir at room temperature for 5 minutes and the previously made solution of thyroxine activated ester prepared in situ was added dropwise to this solution. The mixture was allowed to stir at room temperature for a period of 48 hours. The reaction mixture was concentrated and 100 ml of saturated $Na_2CO_3$ solution was added. The solid was filtered off and washed with 100 ml of water. This crude solid was purified by column chromatography using 50% chloroform in methanol to give 250 mg (0.27 mmol, 48%) of (7).

EXAMPLE 10

Preparation of 5'-[(isoprenyloxycarbonylaminoethyleneamido)-thyroxine(N-tBoc)]-MPA[OMEM] methyl ester conjugate (8)

To 25 mg (0.049 mmol) of (5) was added 1 ml of THF followed by 12.6 mg (0.046 mmol) of N,N'-disuccinimidyl carbonate and 20 µl of triethylamine. The mixture was allowed to stir at room temperature for 18 hours to give the corresponding N-hydroxysuccinimidyl carbonate.

L-thyroxine-[N-tBoc]-amidoethyleneamine (7, 22 mg, 0.023 mmol) was dissolved in 1 ml of anhydrous DMF and 100 µl of triethylamine was added. To this solution was added the previously prepared MPA-N-hydroxysuccinimidyl carbonate solution (generated in situ) dropwise. The reaction was allowed to stir at room temperature for 30 minutes and concentrated in the rotary evaporator. The residue was purified by preparative RP-HPLC (Rainin C-18 (ODS) 21.4 mm×250 mm) using water/acetonitrile gradient system containing 0.1% trifluoroacetic acid. Product containing fractions were combined, acetonitrile was evaporated and the remaining mixture was lyophilized to give 24 mg (0.016 mmol, 34%) of (8). $^1$H-NMR compatible. HR-ES (+) MS: Calc M+Na 1474.0173, Observed 1474.0176

EXAMPLE 11

Preparation of 5'-[(isoprenyloxycarbonylaminoethyleneamido)-thyroxine(N-tBoc)]-MPA[OMEM] conjugate (9)

To 22 mg (0.015 mmol) of 5'-[(isoprenyloxycarbonylaminoethyleneamido)-thyroxine(N-tBoc)]-MPA[OMEM] methyl ester (8) was added 2 ml of methanol and a solution of 40 mg (1.6 mmol) of lithium hydroxide in 1 ml of water. The mixture was allowed to stir at room temperature for 2 days and concentrated in the rotary evaporator. To the reaction mixture 2 ml of water and the pH was adjusted to 6 using dilute phosphoric acid. The reaction was concentrated to dryness and 100 ml of methanol was added. The mixture was filtered and the filtrate was concentrated. The residue was purified by preparative RP-HPLC (Rainin C-18 (ODS) 21.4 mm×250 mm) using water/acetonitrile gradient system containing 0.1% trifluoroacetic acid. Product containing fractions were combined, acetonitrile was evaporated and the remaining mixture was lyophilized to give 11 mg (0.007 mmol, 52%) of (9).

EXAMPLE 12

Preparation of 5'-[(isoprenyloxycarbonylaminoethyleneamido)-thyroxine]-MPA conjugate (11)

To 5 mg (0.003 mmol) of 5'-[(isoprenyloxycarbonylaminoethyleneamido)-thyroxine(N-tBoc)]-MPA[OMEM] methyl ester conjugate (9) was added 1.5 ml of dichloromethane and the solution was cooled at 0° C. To this solution was added an ice-cold solution of 200 µl of 50% trifluoroacetic acid in dichloromethane in two portions at an interval of 5 minutes. The mixture was allowed to stir in ice-bath for additional 15 minutes. This was concentrated under reduced pressure. The product formation was monitored by analytical RP-HPLC (C-18, Vydac 4.6 mm×250 mm) using a gradient system of water/acetonitrile containing 0.1% trifluoroacetic acid.. The reaction was resubjected to trifluoroacetic acid treatment. The crude reaction mixture was redissolved in 1.5 ml of dichloromethane and the solution was cooled to 0° C. To this solution was added an ice-cold solution of 200 µl of 50% trifluoroacetic acid in dichloromethane in two portions at an interval of 5 minutes. The mixture was allowed to stir at 0° C. for 25 minutes. The reaction mixture was concentrated in the rotary evaporator and then in the high vacuum pump. The product formation was monitored by analytical RP-HPLC (C-18, Vydac 4.6 mm×250 mm) using a gradient system of water/acetonitrile containing 0.1% trifluoroacetic acid. The results indicated that the reaction is a conjugate mixture containing mostly the MEM-deprotected 5'-[(isoprenyloxycarbonylaminoethyleneamido)-thyroxine(N-tBoc)]-MPA (10) with some desired product (11).

The above product was again resubjected to the trifluoroacetic acid treatment. The above reaction mixture was treated with 2 ml of dichloromethane and cooled in an ice-bath. To the mixture was added an ice-cold solution of 600 µl of 50% trifluoroacetic acid in dichloromethane in three portions at an interval of 5 minutes. The mixture was allowed to stir in the ice-bath for additional 25 minutes. The mixture was concentrated under reduced pressure. The crude product was purified by semi-preparative RP-HPLC (C-18, Vydac, 10 mm×250 mm) using a gradient system of water/acetonitrile containing 0.1% trifluoroacetic acid (3 ml/min). Product containing fractions were combined, acetonitrile was evaporated, and the remaining mixture was lyophilized to give 1.8 mg (0.0013 mmol, 45%) of (11). $^1$H-NMR compatible, LC/MS: M+Na 1271.8

EXAMPLE 13

Preparation of MPA t-butyl Ester (12)

Mycophenolic acid (860 mg, 2.68 mmol) was dissolved in a solution of 1,4-dioxane containing 700 µl of conc. $H_2SO_4$. The solution was transferred into a pressure bottle and this was cooled in ice. Isobutylene (20 ml) was poured into the mycophenolic acid solution. The pressure bottle was capped and stirred magnetically very slowly for 2 days at roomtemperature. The mixture was allowed to cool under dry ice/ acetone and the pressure was slowly released. The mixture was allowed to warm up to room temperature and diluted with 150 ml of ethyl acetate. The aqueous part was separated and extracted with 3×100 ml of ethyl acetate. The combined organic layer was washed with 100 ml of water, 100 ml of saturated $NaHCO_3$ followed by 100 ml of water and dried ($Na_2SO_4$) and concentrated. The crude product was purified by silica gel column chromatography using 80% hexane in ethyl acetate to give 590 mg (1.63 mmol, 60%) of MPA t-butyl ester (12).

EXAMPLE 14

Preparation of 5'-ethoxycarbonylmethyl-MPA t-butyl ester (13)

A solution of 3.2 ml (3.19 mmol) of sodium bis (trimethylsilyl)amide (1.0M solution in THF) was cooled in dry ice/acetone bath to −78° C. under argon atmosphere. To this cooled solution was added 0.32 ml (2.64 mmol) of DMPU and allowed to stir at −78° C. for 15 minutes. A solution of 398 mg (1.10 mmol) of MPA t-butyl ester (12) in 5 ml of freshly distilled THF was added dropwise to the reaction mixture. The reaction mixture was allowed to stir at −78° C. for 30 minutes and 0.18 ml (1.61 mmol) of ethyl bromo acetate was added. The resulting mixture was stirred stirred at −40° C. for 3 hours and 0° C. for 1 hour. The reaction was quenched with 10 ml of saturated ammonium chloride and the mixture was allowed to warm up to room temperature. An additional 80 ml of saturated ammonium chloride was added and the water part was extracted with ethyl acetate (3×80 ml). The organic layers were combined, dried ($Na_2SO_4$) and concentrated. The crude product was purified by silica gel chromatography, first eluting using 80% hexane in ethyl acetate and then 50% ethyl acetate in hexane to give 330 mg of product containing impurities. This was repurified by preparative RP-HPLC (Rainin C-18 (ODS) 21.4 mm×250 mm) using water/acetonitrile gradient system containing 0.1% trifluoroacetic acid. Product containing fractions were combined, acetonitrile was evaporated and the remaining mixture was lyophilized to give 163 mg (0.35 mmol, 32%) of (13). 1H-NMR compatible, HR-FAB MS: Calc for M+Na 485.2151, Observed 485.2140

EXAMPLE 15

Preparation of 5'-carboxymethyl-MPA t-butyl ester (14)

A solution of 141 mg (0.30 mmol) of (13) was prepared in 41.1 ml of DMSO. This was diluted with 81 ml of 0.1 M potassium phosphate buffer pH 7.0 and 306 µl of esterase (from pig liver, Roche Diagnostics, suspension 10 mg/ml) was added. The reaction mixture was allowed to stir at room temperature for 3 days and filtered. The filtrate was purified using preparative RP-HPLC (WATERS DELTAPAK C-18 50×250 mm, water/acetonitrile-system containing 0.1% trifluoroacetic acid). Product containing fractions were combined, acetonitrile was evaporated and the mixture was lyophilized to give 76 mg (0.17 mmol, 57%) of 5'-carboxymethyl-MPA t-butyl ester (14).

EXAMPLE 16

Preparation of 5'-(digoxigenin-3-yl-β-amidomethyl)-MPA t-butyl ester conjugate (15)

5'-Carboxymethyl-MPA t-butyl ester (20 mg, 46 µmol) was dissolved in 193 µl DMF. To this reaction mixture 7.95 mg (69 µmol) of N-hydroxysuccinimide and 11.4 mg (55.2 µmol) of DCC were added. The reaction mixture was allowed to stir at room temperature for 3 hours. An additional 2.65 mg (23 µmol) of N-hydroxysuccinimide and 2.85 mg (13.8 µmol) of DCC dissolved in 55 µl of DMF were added and the reaction mixture was allowed to stir at room temperature for 1 hour. A solution of 23.2 mg (46 µmol) of 3-β-amino-digoxigenin in 63.8 µl (460 µmol) of triethylamine and 120 µl of DMF was added. The reaction mixture was allowed to stir at room temperature for 1 hour and evaporated to give 68 mg of crude product (15). This was used in the next step without further purification.

EXAMPLE 17

Preparation of 5'-(digoxigenin-3-yl-β-amidomethyl)-MPA conjugate (16)

The crude product of 5'-(digoxigenin-3-yl-β-amidomethyl)-MPA t-butyl ester (15) was dissolved in 3 ml of dichloromethane. To the reaction mixture 3 ml of trifluoroacetic acid was added and the solution was allowed to stir at room temperature for exact 30 minutes. The solution was then evaporated and the residue was purified immediately as follows:

The residue was dissolved in 1.5 ml of methanol and immediately purified using semi-preparative RP-HPLC (Vydac C-18 300 Å10 µm 22×250 mm, water/acetonitrile-system containing 0.1% trifluoroacetic acid) to give 7.3 mg of isomer A (16A) and 7.4 mg of isomer B (16B).

TABLE 4

| Isomer characteristics | | |
|---|---|---|
| | Isomer A | Isomer B |
| RP-HPLC (Vydac C-18 5 µm 300 Å 4.6 × 250 mm; Gradient: 0 to 100% acetonitrile + 0.1% TFA in 50 minutes) | 93% (UV 226 nm) Rt = 25.09 min | 87% (UV 226 nm) Rt = 25.34 min |
| MS | ok | ok |
| 1H-NMR | compatible | compatible |

EXAMPLE 18

Preparation of Antibody Reagent for Thyroxine Assay

One liter of an antibody reagent, or first reagent, was prepared as follows. Approximately 800 ml deionized water was dispensed into a container and 6.0 grams of N-[2-acetamido]-2-aminoethanesulfonic acid ACES were added and dissolved. The pH was adjusted to 6.0 with 2N NaOH.

Then 0.663 grams NAD were added and dissolved completely. Then 0.95 grams sodium azide was added and dissolved, and finally 1.0 gram of SUTTOCIDE A was added and dissolved. The volume was adjusted to one liter with deionized water. Finally, 10 milligrams of anti-L-thyroxine monoclonal antibody was added.

TABLE 5

Composition of Antibody Reagent

| Antibody reagent, pH 6.0 Component | Molec. wt. | M | g/l | Function | 150 µl final M |
|---|---|---|---|---|---|
| ACES | 182.2 | 0.0330 | 6.0 | Buffer, NAD stabilizer | 0.0163 |
| NAD | 663.4 | 0.001 | 0.6634 | Enzyme substrate | 0.0005 |
| Anti-L-thyroxine | 150,000 | — | 0.010 | Monoclonal antibody | — |
| Na azide | 65.0 | 0.0146 | 0.95 | Anti-microbial preservative | 0.0072 |
| SUTTOCIDE A (50%) | 127.1 | 0.004 | 1.0 | Anti-microbial preservative | 0.004 |

The antibody used was prepared according to procedures readily available and known to those skilled in the art to which the present invention belongs. Any antibody with specificity for thyroxine, either monoclonal or polyclonal, may be used in the practice of the present invention. Monoclonal antibodies are generally preferred, however, because of their ease and consistency of production.

EXAMPLE 19

Preparation of Enzyme Reagent for Thyroxine Assay

One liter of an enzyme reagent, or second reagent, was prepared as follows. Approximately 800 ml deionized water was dispensed into a container and 168.8 grams of NaTAPSO was added and completely dissolved. Next, 1.15 grams of TCEP was dissolved. Next 31.4 grams of IMP was dissolved, then 2.23 grams of $Na_2EDTA$ were dissolved. Next 1.0 gram of SUTTOCIDE A was dissolved. The volume was adjusted to one liter with deionized water. Enough recombinant human IMPDH-II was added (as a 35% ammonium sulfate precipitate of an *E. coli* lysate supernatant) and dissolved completely in order to achieve a change in absorbance at 340 nm of $780 \times 10^{-4}$ over 5 minutes at 37° C. Next 0.0005 grams of ligand-inhibitor 5'-[(isoprenyloxycarbonylamino-ethyleneamido)-thyroxine]-MPA conjugate (11) was added and dissolved.

EXAMPLE 20

Measurement of Thyroxine

Saline samples spiked with L-thyroxine were assayed for thyroxine using the method of the present invention. The samples were prepared by suspending L-thyroxine (Sigma Chemical) in saline, dissolving by the dropwise addition of 1 N NaOH, and then diluting with saline to achieve final concentrations of 100, 250, 500 and 1000 ng/ml.

Figure 2:
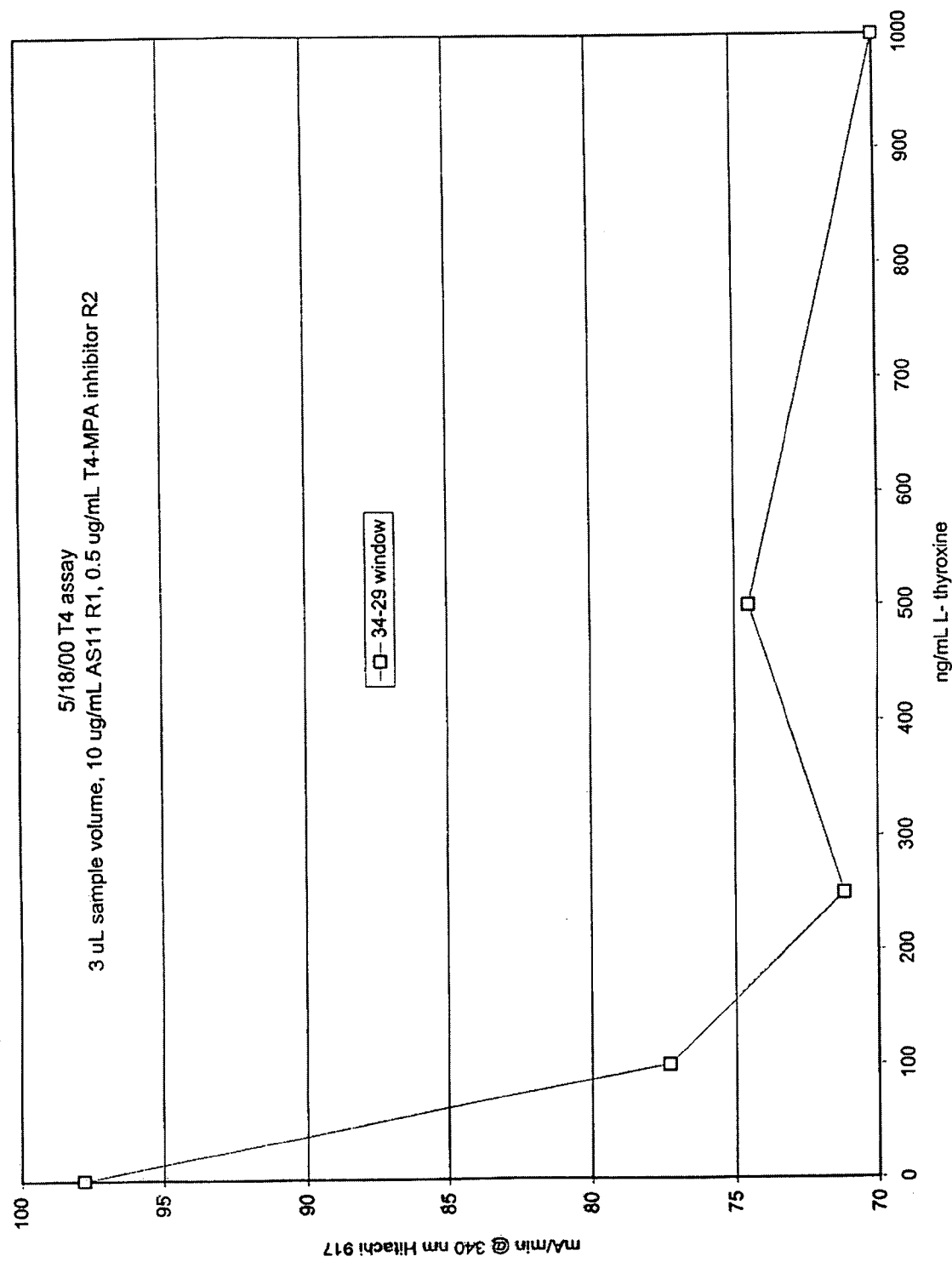
FIG. 2 is a graph prepared by plotting the results obtained in Example 20 in which samples containing thyroxin were assayed according to the present invention. Concentration of thyroxin is plotted on the X-axis and delta (or end-point) absorbance at 340 nm is plotted on the Y-axis.

An HITACHI 917 analyzer (Roche Diagnostics Corp., Indianapolis) was programmed to dispense 3 µl of sample and 150 µl of antibody reagent into a 37° C. cuvette, which were then mixed and incubated for 5 minutes after which time 150 µl of enzyme reagent was added and mixed. The rate at 340 nm (mA/min) was calculated during the period 3 minutes 13 seconds to 4 minutes 42 seconds (read window 29–34) following enzyme reagent addition. Results obtained are shown in FIG. 2.

EXAMPLE 21

Preparation of Antibody Reagent for Digoxigenin Assay

One liter of an antibody reagent, or first reagent, was prepared as follows. Approximately 800 ml deionized water was dispensed into a container and 6.0 grams of ACES were added and dissolved. The pH was adjusted to 6.0 with 2N NaOH. Then 0.53 grams NAD were added and dissolved completely. Then 0.95 grams sodium azide was added and dissolved, and finally 1.0 gram of SUTTOCIDE A was

TABLE 6

Composition of Enzyme Reagent

| Enzyme reagent, pH 8.0 Component | Molec. wt. | M | g/l | Function | 150 µl final M |
|---|---|---|---|---|---|
| Na TAPSO | 281.3 | 0.6 | 168.8 | Buffer, enzyme stabilizer-reduces enzyme aggregation | 0.3 |
| TCEP | 286.65 | 0.004 | 1.15 | Enzyme stabilizer-reduces cysteine sulfhydryl groups | 0.002 |
| $Na_2$ IMP | 392.2 | 0.08 | 31.4 | Enzyme substrate, enzyme stabilizer | 0.04 |
| $Na_2EDTA$ | 372.2 | 0.006 | 2.23 | Enzyme stabilizer-chelates heavy metals, maintains reduced cysteine sulfhydryls | 0.003 |
| SUTTOCIDE A (50%) | 127.1 | 0.004 | 1.0 | Anti-microbial preservative | 0.004 |
| IMPDH-II | — | — | — | Enzyme | — |
| 5'-[(isoprenyl-oxycarbonyl-aminoethylene-amido)-thyroxine]-MPA | 1363.44 | $3.7 \times 10^{-7}$ | 0.0005 | Ligand-inhibitor | $1.8 \times 10^{-7}$ | added and dissolved. The volume was adjusted to one liter with deionized water. Finally, 25 milligrams of anti-digoxigenin monoclonal antibody was added.

TABLE 7

Composition of Antibody Reagent

| Antibody reagent, pH 6.0 Component | Molec. wt. | M | g/l | Function | 150 µl final M |
|---|---|---|---|---|---|
| ACES | 182.2 | 0.0330 | 6.0 | Buffer, NAD stabilizer | 0.0163 |
| NAD | 663.4 | 0.0008 | 0.53 | Enzyme substrate | 0.0004 |
| Anti-digoxigenin | 150,000 | | 0.025 | Monoclonal antibody | |
| Na azide | 65.0 | 0.0146 | 0.95 | Anti-microbial preservative | 0.0072 |
| SUTTOCIDE A (50%) | 127.1 | 0.004 | 1.0 | Anti-microbial preservative | 0.004 |

The antibody used is commercially available (Roche Cat. No. 1333062). However, any antibody with specificity for digoxigenin, either monoclonal or polyclonal, may be used in the practice of the present invention. Monoclonal antibodies are generally preferred, however, because of their ease and consistency of production.

EXAMPLE 22

Preparation of Enzyme Reagent for Digoxigenin Assay

One liter of an enzyme reagent, or second reagent, was prepared as follows. Approximately 800 ml deionized water was dispensed into a container and 56.3 grams of NaTAPSO was added and completely dissolved. Then 81.6 grams of Na, acetate-3H$_2$O were added and dissolved. Next, 1.15 grams of TCEP was dissolved. Next 0.319 grams of IMP was dissolved, then 2.23 grams of Na$_2$EDTA were dissolved. Next 1.0 gram of SUTTOCIDE A was dissolved. The volume was adjusted to one liter with deionized water. Enough recombinant human IMPDH-II was added (as a 35% ammonium sulfate precipitate of an *E. coli* lysate supernatant) and dissolved completely in order to achieve a change in absorbance at 340 nm of 1280×10$^{-4}$ over 5 minutes at 37° C. Next 0.001 grams of ligand-inhibitor (4'-[(digoxigenin-3-yl)-oxymethylcarbonyl-DADOO-carbonylmethyl]-MPA or 5'-[(digoxigenin-3-yl)-oxymethylcarbonyl-DADOO-carbonylmethyl]-MPA) was added and dissolved.

EXAMPLE 23

Measurement of Digoxigenin

Figure 3:
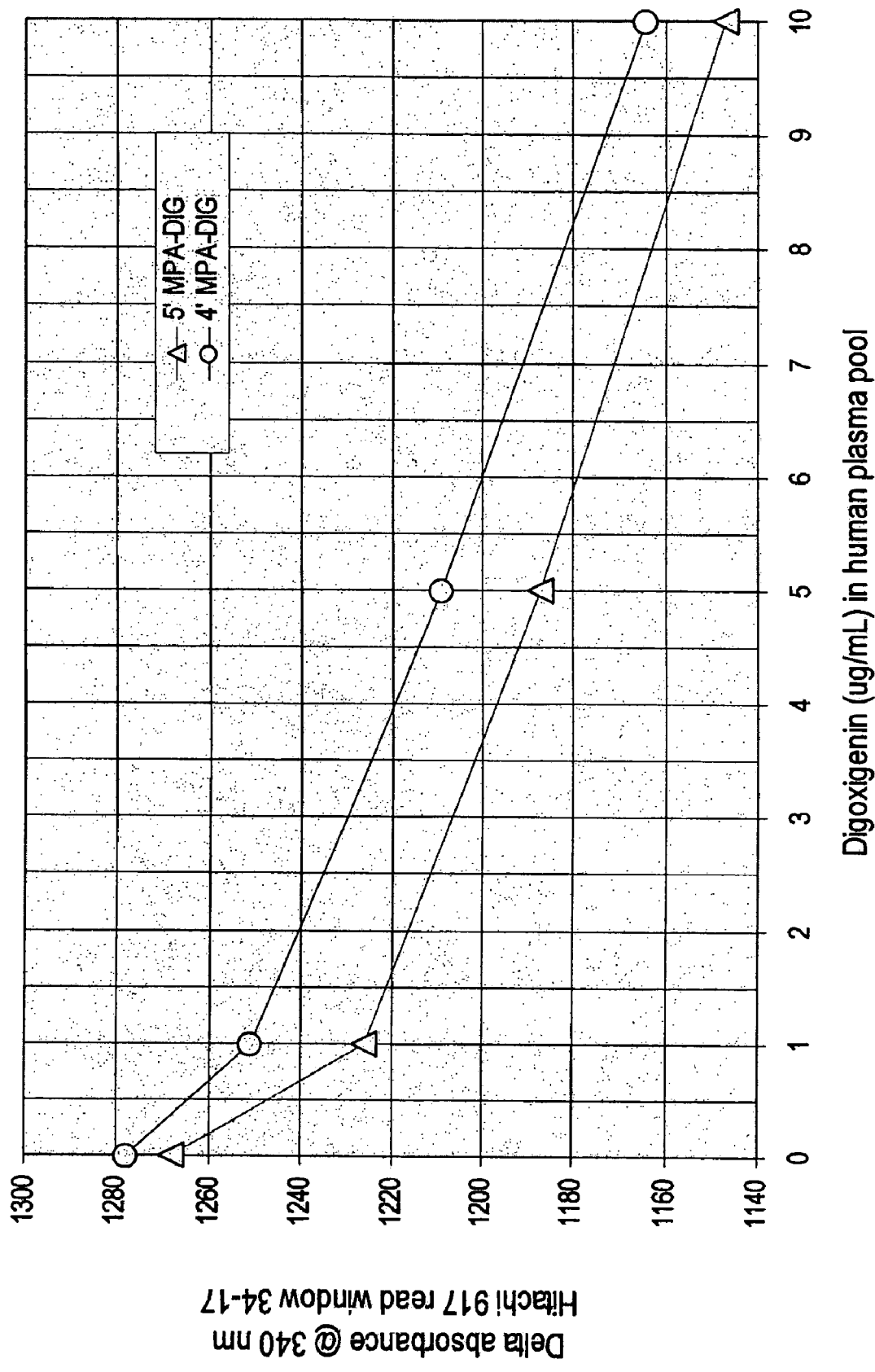
FIG. 3 is a graph prepared by plotting the results obtained in Example 23 in which samples containing digoxigenin were assayed according to the present invention. Concentration of digoxigenin is plotted on the X-axis and delta (or end-point) absorbance at 340 nm is plotted on the Y-axis.

Saline samples spiked with digoxigenin were assayed for digoxigenin using the method of the present invention. The digoxigenin (Sigma chemical) was first dissolved in 100% DMSO and then added to normal human plasma to achieve concentrations of 0.5, 1.0, 5.0 and 10.0 µg/ml. An HITACHI 717 analyzer (Roche Diagnostics Corp., Indianapolis) was programmed to dispense 20 µl of sample and 150 µl of antibody reagent into a 37° C. cuvette, which were then mixed and incubated for 5 minutes after which time 150 µl of enzyme reagent was added and mixed. The difference in absorbance at 340 nm was calculated from the initial addition of enzyme reagent to 5 minutes following enzyme reagent addition. Results obtained are shown in FIG. 3.

This example shows that conjugates prepared at either the 4' or 5' position are useable in the present invention.

EXAMPLE 24

Preparation of Antibody Reagent for Digoxigenin Assay

One liter of an antibody reagent, or first reagent, was prepared as follows. Approximately 800 ml deionized water was dispensed into a container and 6.0 grams of ACES were added and dissolved. The pH was adjusted to 6.0 with 2N NaOH. Then 0.663 grams NAD were added and dissolved completely. Then 0.95 grams sodium azide was added and dissolved, and finally 1.0 gram of SUTTOCIDE A was

TABLE 8

Composition of Enzyme Reagent

| Enzyme reagent, pH 8.0 Component | Molec. wt. | M | g/l | Function | 150 µl final M |
|---|---|---|---|---|---|
| Na TAPSO | 281.3 | 0.2 | 56.3 | Buffer | 0.1 |
| Na acetate-3H$_2$O | 136.1 | 0.6 | 81.6 | Enzyme stabilizer-reduces enzyme aggregation | 0.3 |
| TCEP | 286.65 | 0.004 | 1.15 | Enzyme stabilizer-reduces cysteine sulfhydryl groups | 0.002 |
| Na$_2$ IMP | 392.2 | 0.0008 | 0.319 | Enzyme substrate | 0.0004 |
| Na$_2$EDTA | 372.2 | 0.006 | 2.23 | Enzyme stabilizer-chelates heavy metals, maintains reduced cysteine sulfhydryls | 0.003 |
| SUTTOCIDE A (50%) | 127.1 | 0.004 | 1.0 | Anti-microbial preservative | 0.004 |
| IMPDH-II | — | — | — | Enzyme | — |
| 4'-[(digoxi-genin-3-yl)-oxy-methylcarbonyl-DADOO-carbonylmethyl]-MPA | 939.12 | 1.07 × 10$^{-6}$ | 0.001 | Ligand-inhibitor | 5.3 × 10$^{-7}$ |
| 5'-[(digoxi-genin-3-yl)-oxy-methylcarbonyl-DADOO-carbonylmethyl]-MPA | 939.12 | 1.07 × 10$^{-6}$ | 0.001 | Ligand-inhibitor | 5.3 × 10$^{-7}$ | added and dissolved. The volume was adjusted to one liter with deionized water. Finally, 10 or 15 milligrams of anti-digitoxin monoclonal antibody were added.

TABLE 9

Composition of Antibody Reagent

| Antibody reagent, pH 6.0 Component | Molec. wt. | M | g/l | Function | 150 µl final |
|---|---|---|---|---|---|
| ACES | 182.2 | 0.0330 | 6.0 | Buffer, NAD stabilizer | 0.0163 |
| NAD | 663.4 | 0.001 | 0.6634 | Enzyme substrate | 0.0005 |
| Anti-digitoxin | 150,000 | — | 0.010 or 0.015 | Monoclonal antibody | — |
| Na azide | 65.0 | 0.0146 | 0.95 | Anti-microbial preservative | 0.0072 |
| SUTTOCIDE A (50%) | 127.1 | 0.004 | 1.0 | Anti-microbial preservative | 0.004 |

Less monoclonal antibody was used with digoxigenin isomer B because better assay sensitivity with this inhibitor was observed with lower monoclonal antibody. This may be due to improved competition between IMPDH binding and monoclonal antibody binding with this inhibitor. This could result from an increase in affinity of the inhibitor for IMPDH and monoclonal antibody.

EXAMPLE 25

Preparation of Enzyme Reagent for Digoxigenin Assay

One liter of an enzyme reagent, or second reagent, was prepared as follows. Approximately 800 ml deionized water was dispensed into a container and 168.8 grams of NaTAPSO was added and completely dissolved. Next, 1.15 grams of TCEP was dissolved. Next 31.4 grams of IMP was dissolved, then 2.23 grams of Na$_2$EDTA were dissolved. Next 1.0 gram of SUTTOCIDE A was dissolved. The volume was adjusted to one liter with deionized water. Enough recombinant human IMPDH-II was added (as a 35% ammonium sulfate precipitate of an *E. coli* lysate supernatant) and dissolved completely in order to achieve a change in absorbance at 340 nm of 3300×10$^{-4}$ over 5 minutes at 37° C. Next 0.0002 grams of ligand-inhibitor (5'-[(digoxigenin-3-yl)-β-amidomethyl]-MPA, isomer A or 5'-[(digoxigenin-3-yl)-β-amidomethyl]-MPA, isomer B) was added and dissolved. Or alternatively 0.0005 grams of ligand-inhibitor (5'-[(digoxigenin-3-yl)-oxymethylcarbonyl-DADOO-carbonylmethyl]-MPA, racemic) was added and dissolved.

TABLE 10

Composition of Enzyme Reagent

| Enzyme reagent, pH 8.0 Component | Molec. wt. | M | g/l | Function | 150 µl final M |
|---|---|---|---|---|---|
| NaTAPSO | 281.3 | 0.6 | 168.8 | Buffer, enzyme stabilizer-reduces enzyme aggregation | 0.3 |
| TCEP | 286.65 | 0.004 | 1.15 | Enzyme stabilizer-reduces cysteine sulfhydryl groups | 0.002 |
| Na$_2$IMP | 392.2 | 0.08 | 31.4 | Enzyme substrate, enzyme stabilizer | 0.04 |
| Na$_2$EDTA | 372.2 | 0.006 | 2.23 | Enzyme stabilizer-chelates heavy metals, maintains reduced cysteine sulfhydryls | 0.003 |
| SUTTOCIDE A (50%) | 127.1 | 0.004 | 1.0 | Anti-microbial preservative | 0.004 |
| IMPDH-II | — | — | — | Enzyme | — |
| 5'-[(digoxigenin-3-yl)-β-amido-methyl]-MPA (isomer A) | 749.91 | 2.7 × 10$^{-7}$ | 0.0002 | Ligand-inhibitor | 1.3 × 10$^{-7}$ |
| 5'-[(digoxigenin-3-yl)-β-amido-methyl]-MPA (isomer B) | 749.91 | 2.7 × 10$^{-7}$ | 0.0002 | Ligand-inhibitor | 1.3 × 10$^{-7}$ |
| 5'-[(digoxigenin-3-yl)-oxymethyl-carbonyl-DADOO-carbonylmethyl]-MPA (racemic) | 939.12 | 5.3 × 10$^{-7}$ | 0.0005 | Ligand-inhibitor | 2.7 × 10$^{-7}$ |

EXAMPLE 26

Measurement of Digoxigenin

Figure 4:
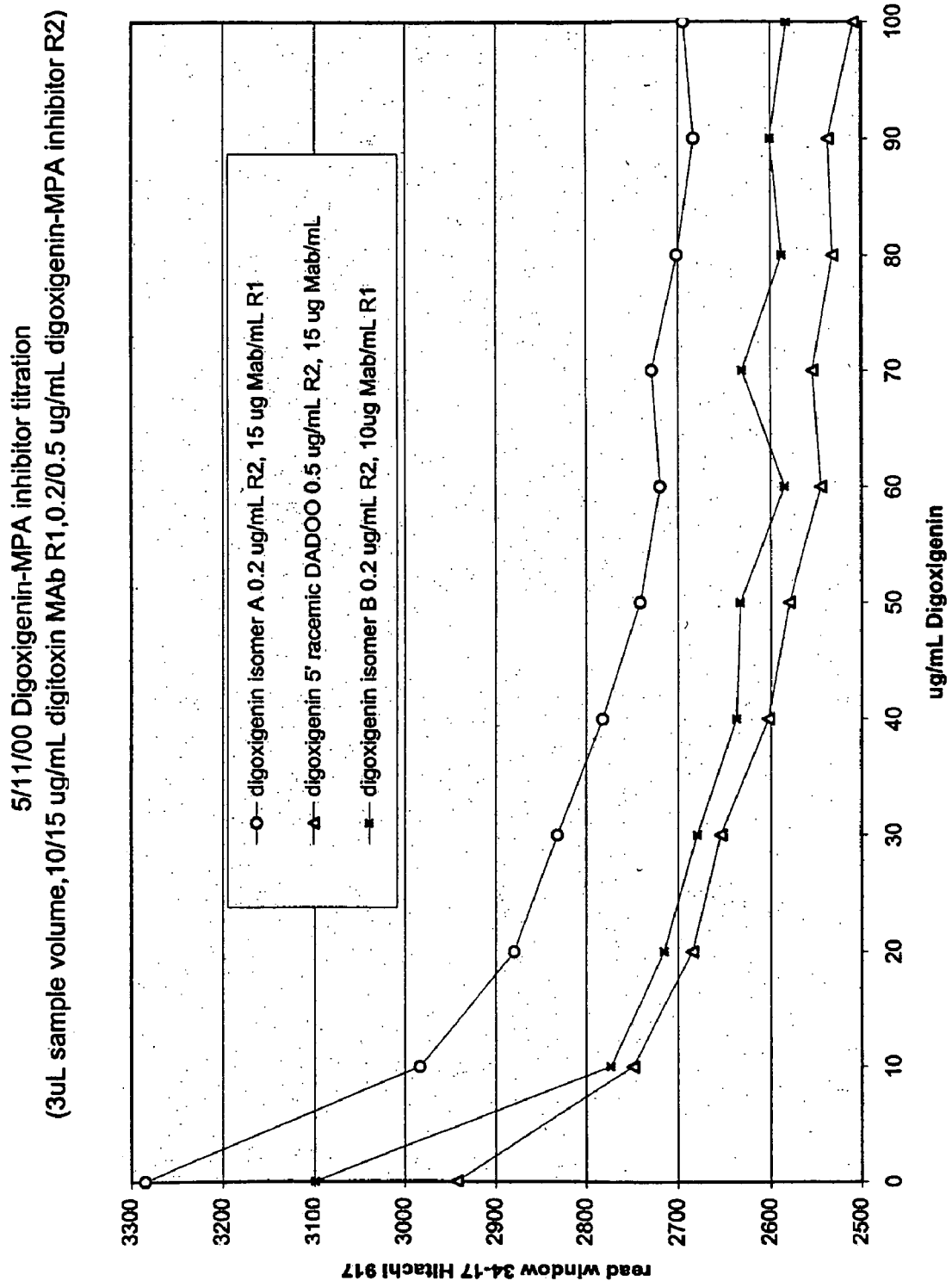
FIG. 4 is a graph prepared by plotting the results obtained in Example 26 in which samples containing digoxigenin were assayed according to the present invention. Concentration of digoxigenin is plotted on the X-axis and rate of absorbance at 340 nm is plotted on the Y-axis.

Saline samples spiked with digoxigenin were assayed for digoxigenin using the method of the present invention. The digoxigenin (Sigma chemical) was first dissolved in 100% DMSO and then added to saline to achieve concentrations of 0, 10, 20, 30, 40, 50, 60, 70, 80, 90 and 100 μg/ml. An HITACHI 917 analyzer (Roche Diagnostics Corp., Indianapolis) was programmed to dispense 3 μl of sample and 150 μl of antibody reagent into a 37° C. cuvette, which were then mixed and incubated for 5 minutes after which time 150 μl of enzyme reagent was added and mixed. The difference in absorbance at 340 mn was calculated from the initial addition of enzyme reagent to 4 minutes 42 seconds following enzyme reagent addition. Results obtained are shown in FIG. 4. This example illustrates the use of different lengths of linkers in the ligand-inhibitor conjugate.

EXAMPLE 27

Preparation of First Reagent for Theophylline Assay

One liter of a first reagent was prepared as follows. Approximately 800 ml deionized water was dispensed into a container and 6.0 grams of ACES were added and dissolved. The pH was adjusted to 6.0 with 2 N NaOH. Then 0.66 grams NAD were added and dissolved completely. Then 0.95 grams sodium azide was added and dissolved, and finally 1.0 gram of SUTTOCIDE A was added and dissolved. The volume was adjusted to one liter with deionized water.

TABLE 11

Composition of First Reagent

| First reagent, pH 6.0 Component | Molec. wt. | M | g/l | Function | 150 μl final M |
|---|---|---|---|---|---|
| ACES | 182.2 | 0.0330 | 6.0 | Buffer, NAD stabilizer | 0.0163 |
| NAD | 663.4 | 0.0010 | 0.66 | Enzyme substrate | 0.0005 |
| Na azide | 65.0 | 0.0146 | 0.95 | Anti-microbial preservative | 0.0072 |
| SUTTOCIDE A (50%) | 127.1 | 0.004 | 1.0 | Anti-microbial preservative | 0.004 |

EXAMPLE 28

Preparation of Second Reagent for Theophylline Assay

One liter of a second reagent was prepared as follows. Approximately 800 ml deionized water was dispensed into a container and 168.8 grams of NaTAPSO were added and completely dissolved. Next, 1.15 grams of TCEP were dissolved. Next 31.4 grams of IMP were dissolved, and then 2.23 grams of $Na_2EDTA$ were dissolved. Next 1.0 gram of SUTTOCIDE A was dissolved. The volume was adjusted to one liter with deionized water. Enough recombinant human IMPDH-II was added (as a 35% ammonium sulfate precipitate of an *E. coli* lysate supernatant) and dissolved completely in order to achieve a change in absorbance at 340 nm of $3100 \times 10^{-4}$ over 5 minutes at 37° C. Next 0.00027 grams of ligand-inhibitor 5'-[(theophylline-8-butyramidoethylaminocarbonyloxy)isoprenyl]-MPA (20) were added and dissolved. Finally, 10 or 25 milligrams of anti-theophylline monoclonal antibody were added.

TABLE 12

Composition of Second Reagent

| Second reagent, pH 8.0 Component | Molec. wt. | M | g/l | Function | 150 μl final M |
|---|---|---|---|---|---|
| Na TAPSO | 281.3 | 0.6 | 168.8 | Buffer, enzyme stabilizer-reduces enzyme aggregation | 0.3 |
| TCEP | 286.65 | 0.004 | 1.15 | Enzyme stabilizer-reduces cysteine sulfhydryl groups | 0.002 |
| $Na_2$ IMP | 392.2 | 0.08 | 31.4 | Enzyme substrate, enzyme stabilizer | 31.4 |
| $Na_2EDTA$ | 372.2 | 0.006 | 2.23 | Enzyme stabilizer-chelates heavy metals, maintains reduced cysteine sulfhydryls | 0.003 |
| SUTTOCIDE A (50%) | 127.1 | 0.004 | 1.0 | Anti microbial preservative | 0.004 |
| IMPDH-II | — | — | — | Enzyme | — |
| Anti-Theophylline | 150,000 | — | 0.010–0.025 | Monoclonal antibody | — |

TABLE 12-continued

Composition of Second Reagent

| Second reagent, pH 8.0 Component | Molec. wt. | M | g/l | Function | 150 µl final M |
|---|---|---|---|---|---|
| 5'-[(theophyl-line-8-butyramidoethyl-aminocarbonyloxy) isoprenyl]-MPA | 738.78 | $3.6 \times 10^{-7}$ | $2.7 \times 10^{-4}$ | Ligand-inhibitor | $1.8 \times 10^{-7}$ |

The antibody used was prepared according to procedures readily available and known to those skilled in the art to which the present invention belongs. Any antibody with specificity for theophylline, either monoclonal or polyclonal, may be used in the practice of the present invention. Monoclonal antibodies are generally preferred, however, because of their ease and consistency of production.

EXAMPLE 29

Measurement of Theophylline

Figure 5:
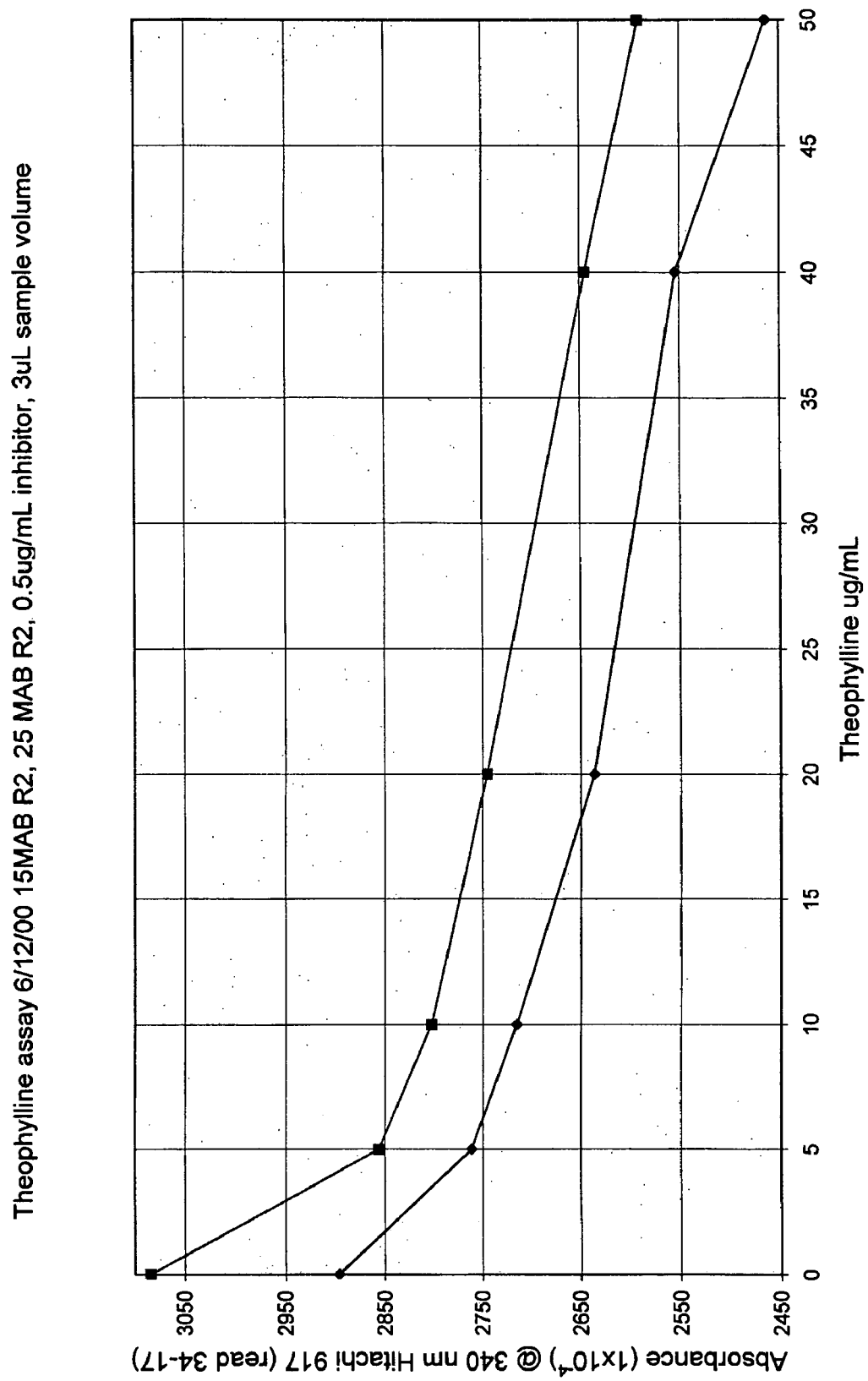
FIG. 5 is a graph prepared by plotting the results obtained in Example 29 in which samples containing theophylline were assayed according to the present invention. Concentration of theophylline is plotted on the X-axis and rate of absorbance at 340 nm is plotted on the Y-axis.
Figure 6:
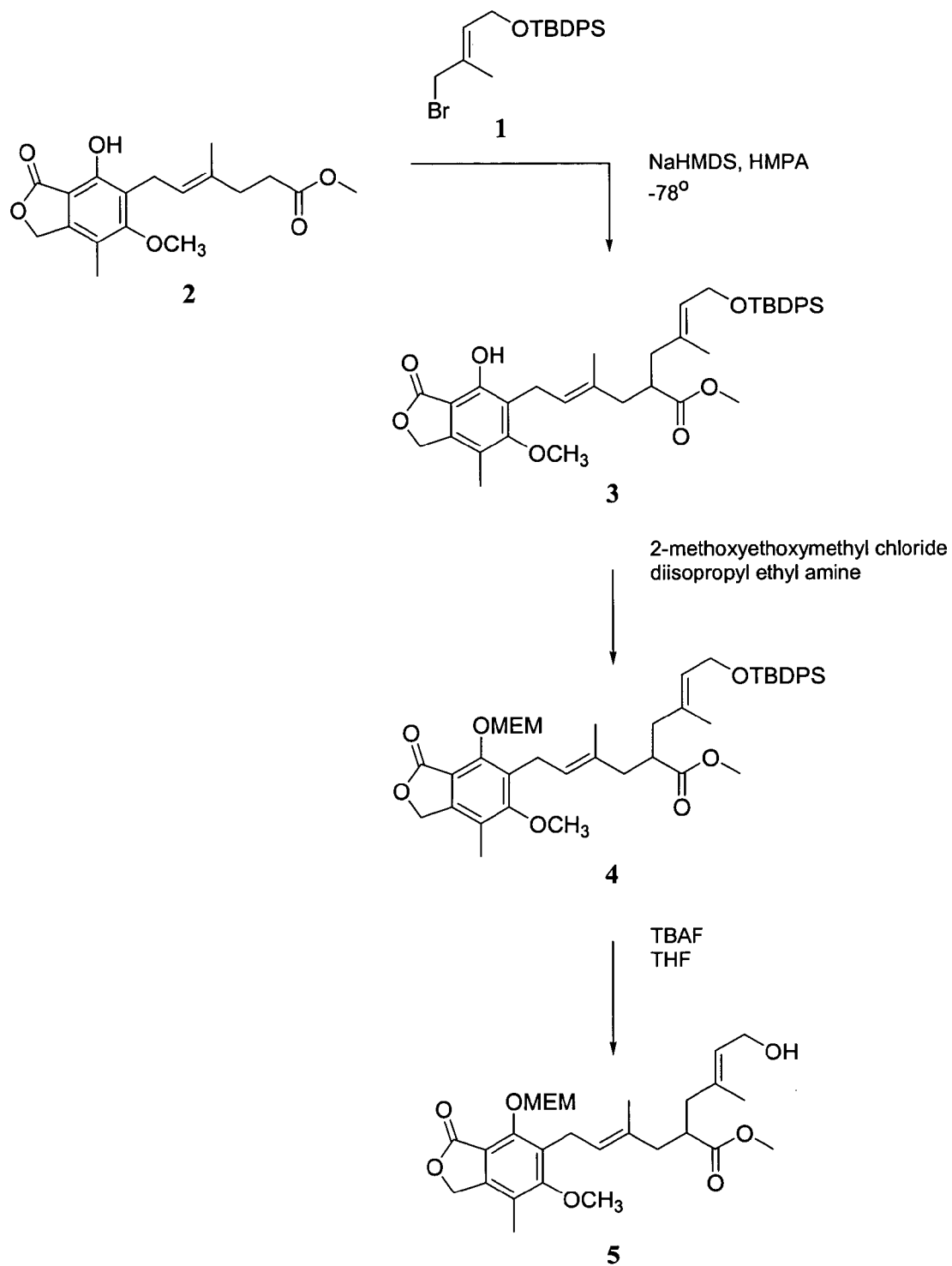
FIG. 6 illustrates the preparation of 5'-isoprenyl[OH]-MPA[OMEM] methyl ester as described in Examples 4, 5, 6 and 7.
Figure 7:
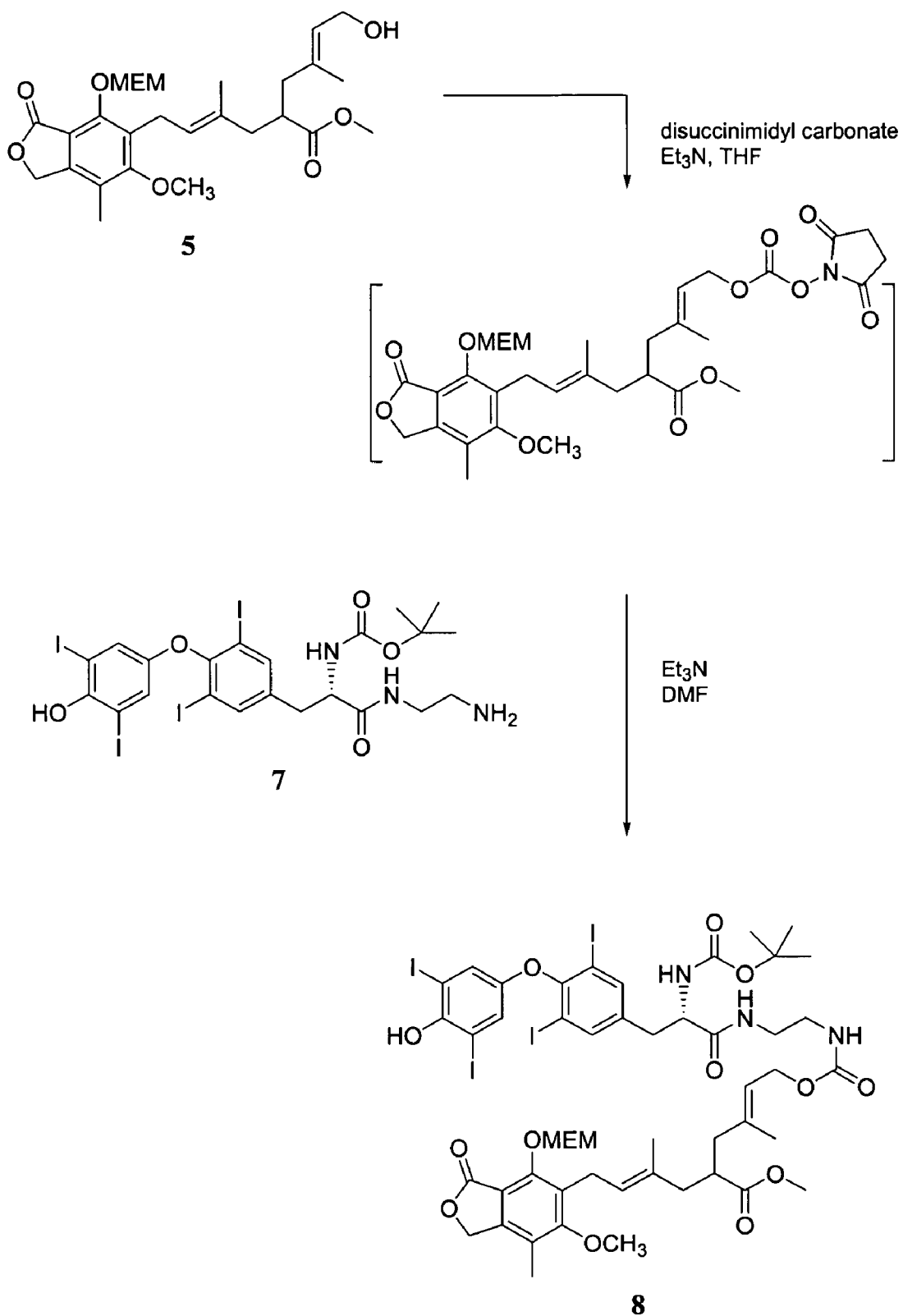
FIG. 7 illustrates the preparation of 5'-[isoprenyloxycarbonylaminoethylene-amido)-thyroxine(N-tBoc)]-MPA [OMEM] methyl ester conjugate as described in Examples 8, 9 and 10.
Figure 8:
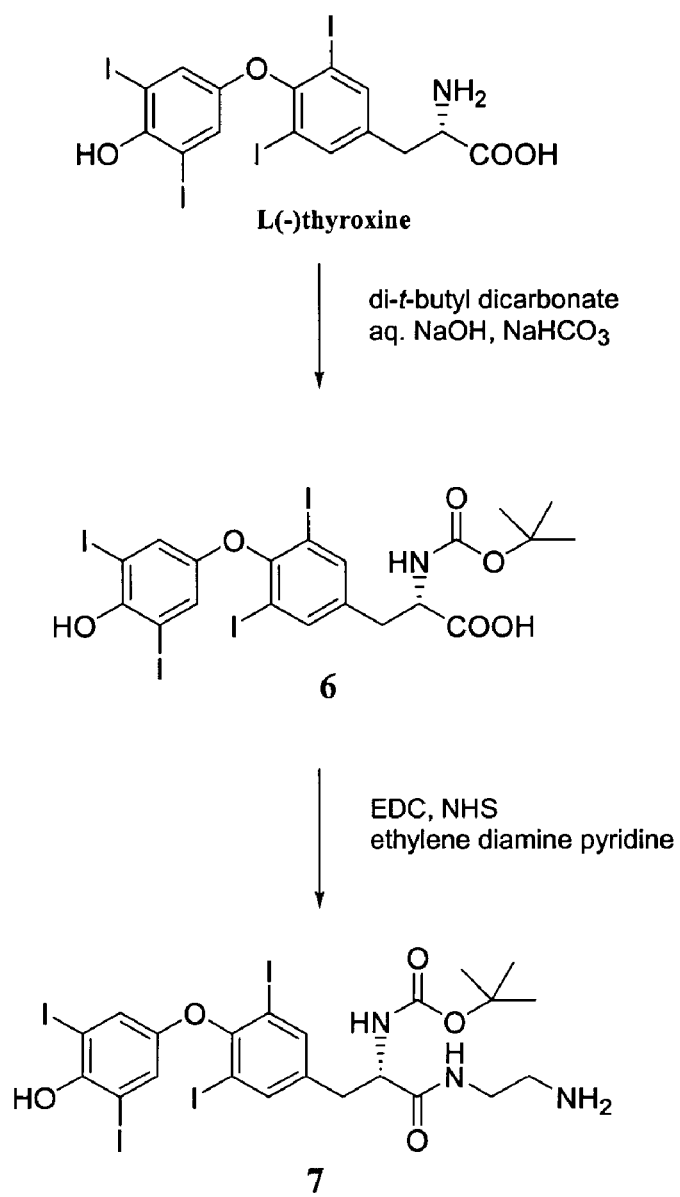
FIG. 8 illustrates the preparation of L-thyroxine(N-tBoc)-amidoethyleneamine as described in Example 9.
Figure 9:
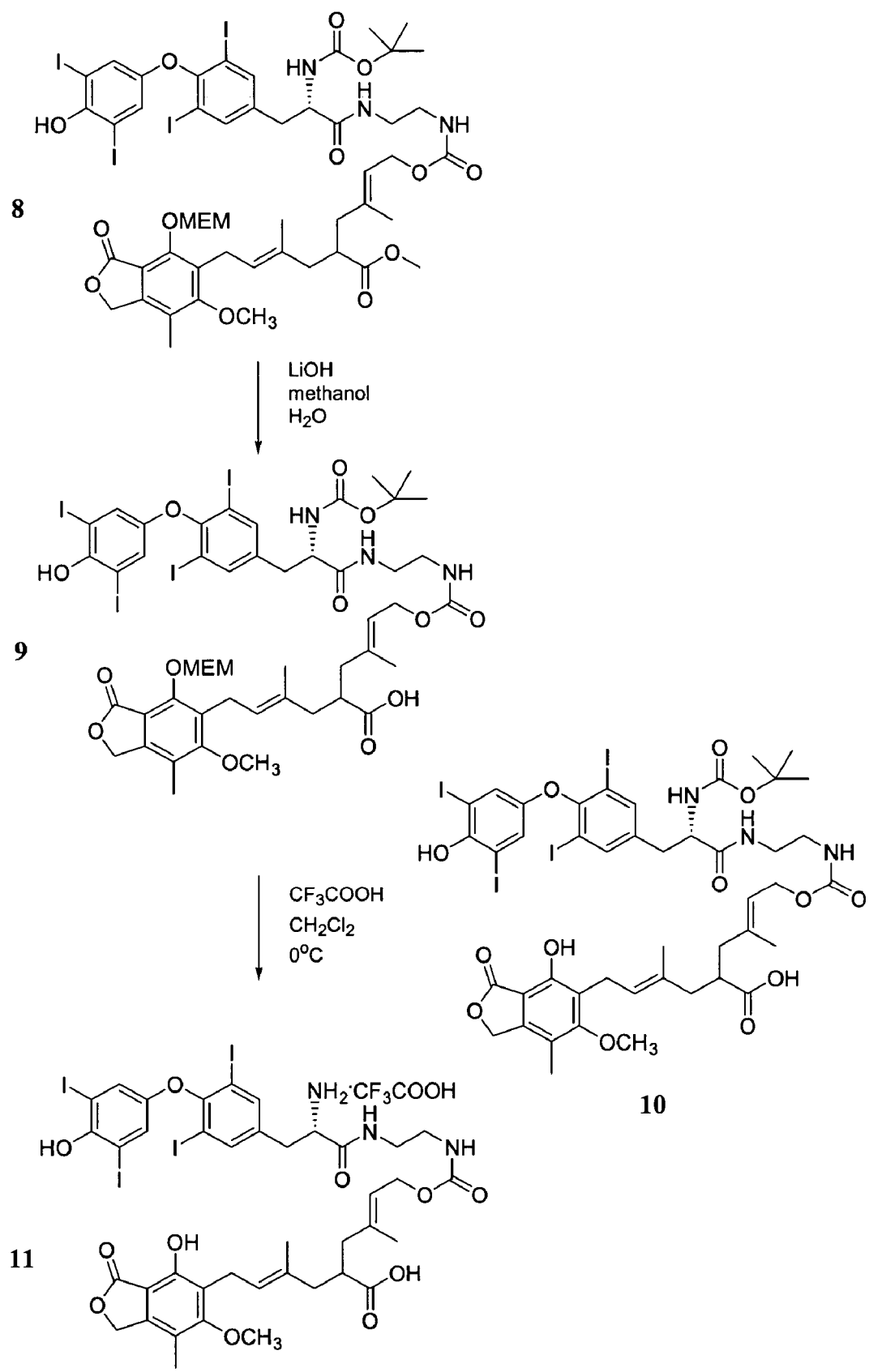
FIG. 9 illustrates the preparation of 5'-[(isoprenyloxycarbonylamino-ethyleneamido)-thyroxine]-MPA conjugate as described in Examples 11 and 12.
Figure 10:
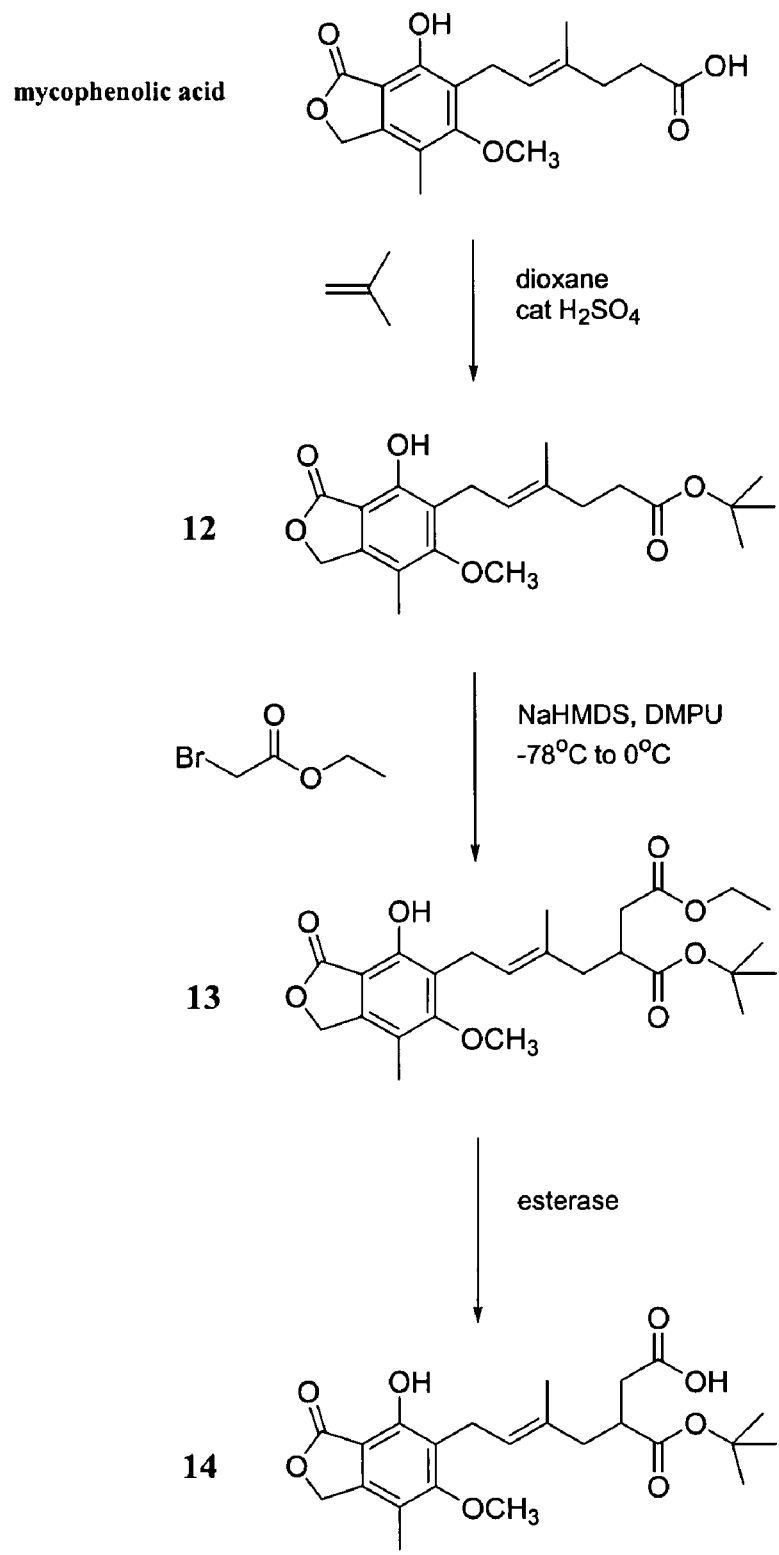
FIG. 10 illustrates the preparation of 5'-carboxymethyl-MPA t-butyl ester as described in Examples 13, 14 and 15.
Figure 11:
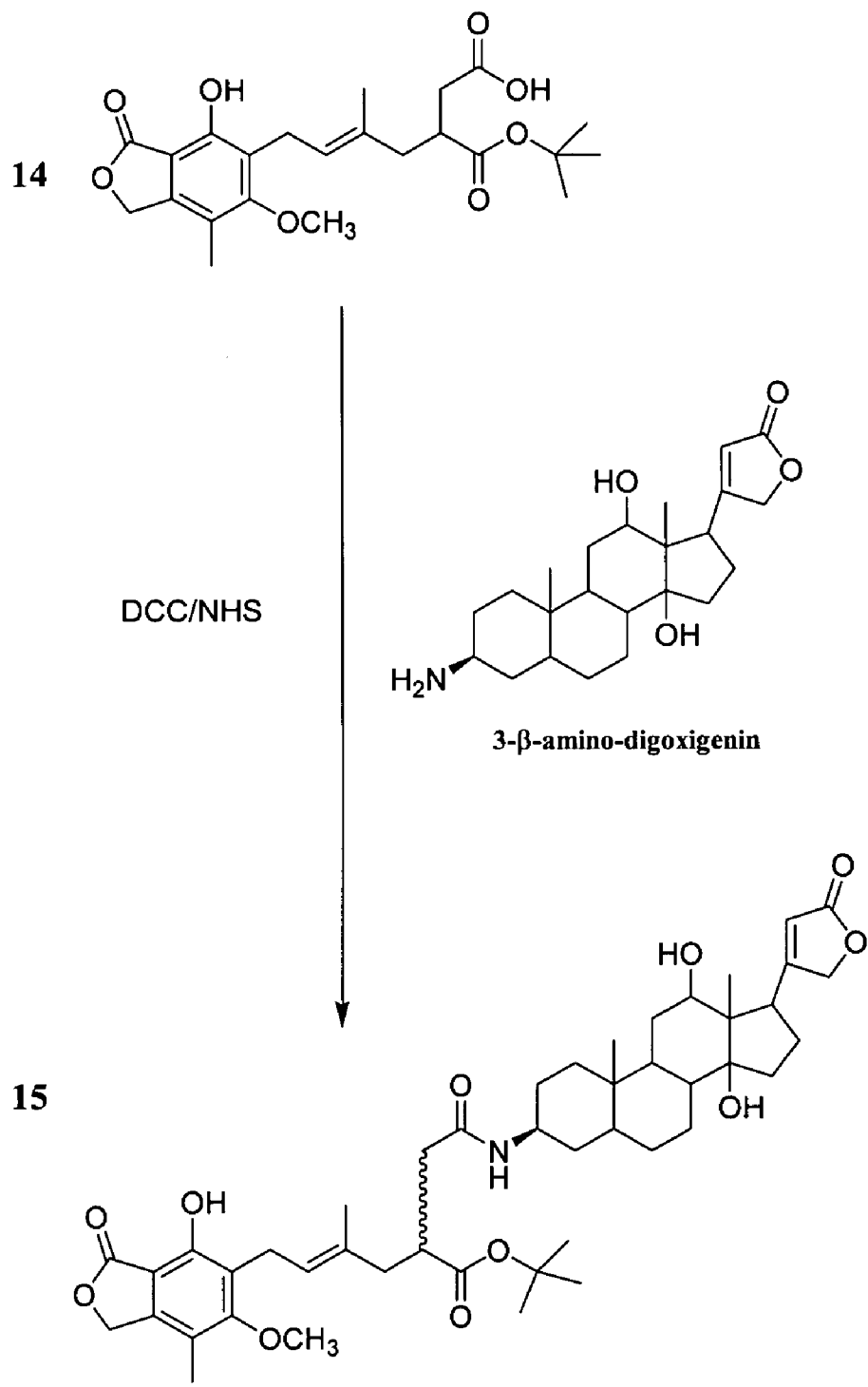
FIG. 11 illustrates the preparation of 5'-(digoxigenin-3-yl-p-amidomethyl)-MPA t-butyl ester conjugate as described in Example 16.
Figure 12:
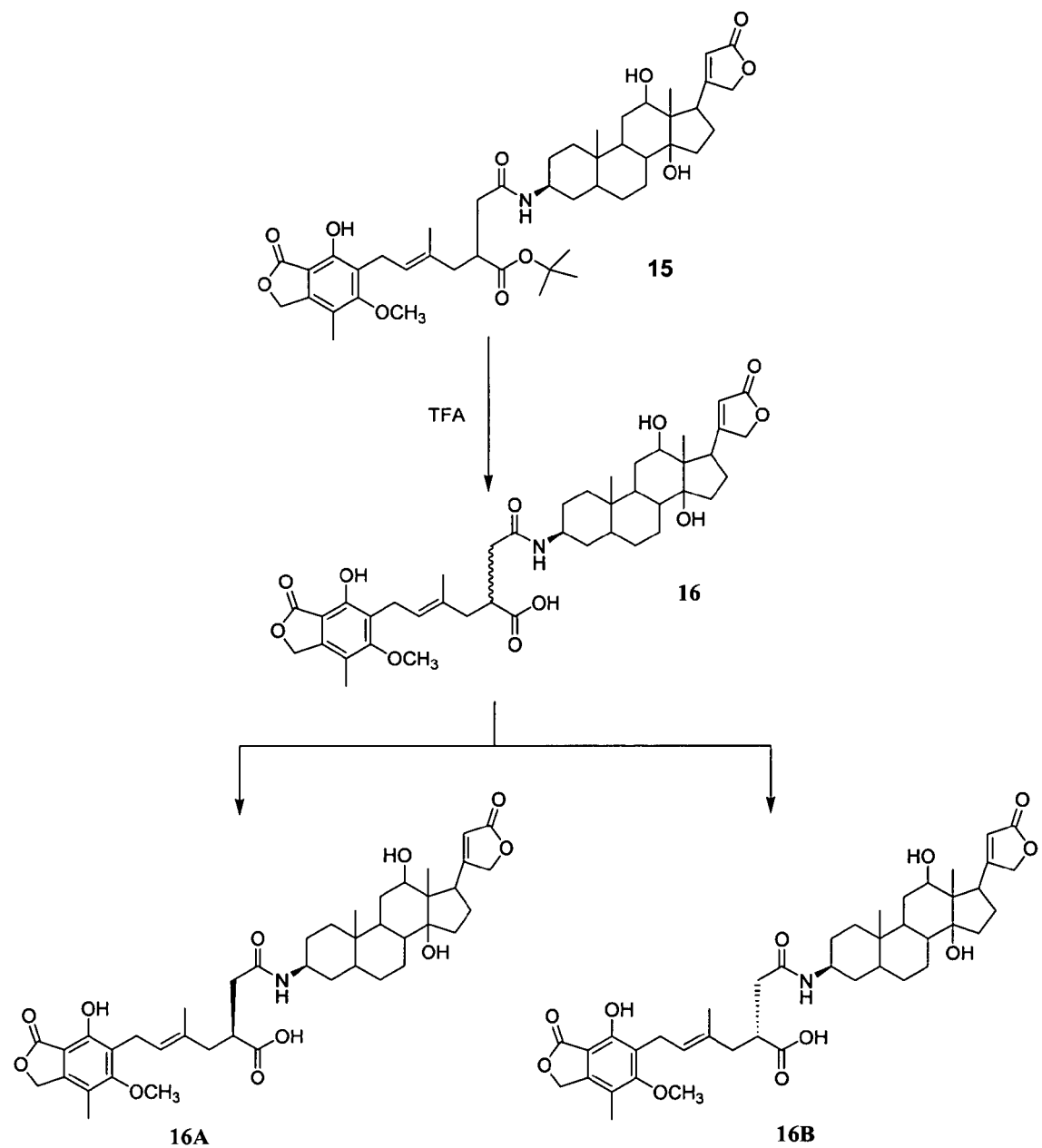
FIG. 12 illustrates the preparation of 5'-(digoxigenin-3-yl-p-amidomethyl)-MPA conjugate, isomer A and isomer B, as described in Example 17.
Figure 13:
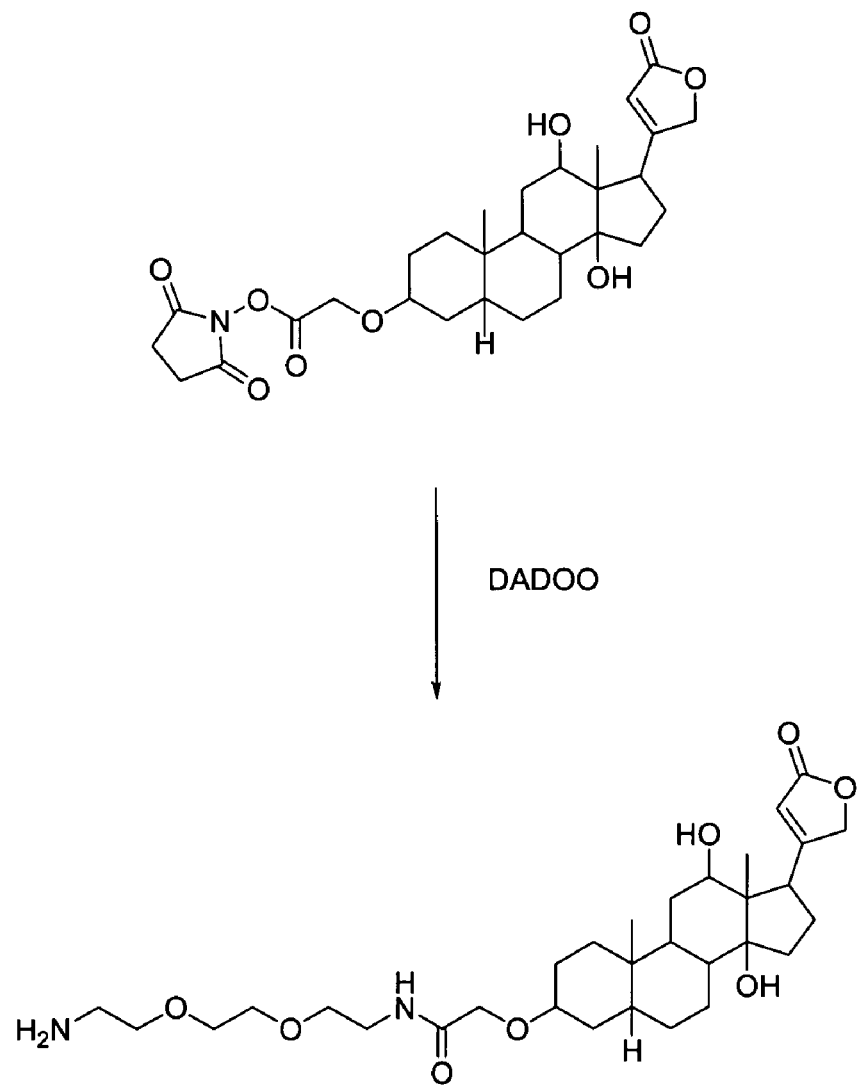
FIGS. 13 and 14 illustrate the preparation of 4'-(digoxigenin-3-yl)-oxymethylcarbonyl-DADOO-carbonylmethyl]-MPA, as described in Examples 31 and 32.
Figure 14:
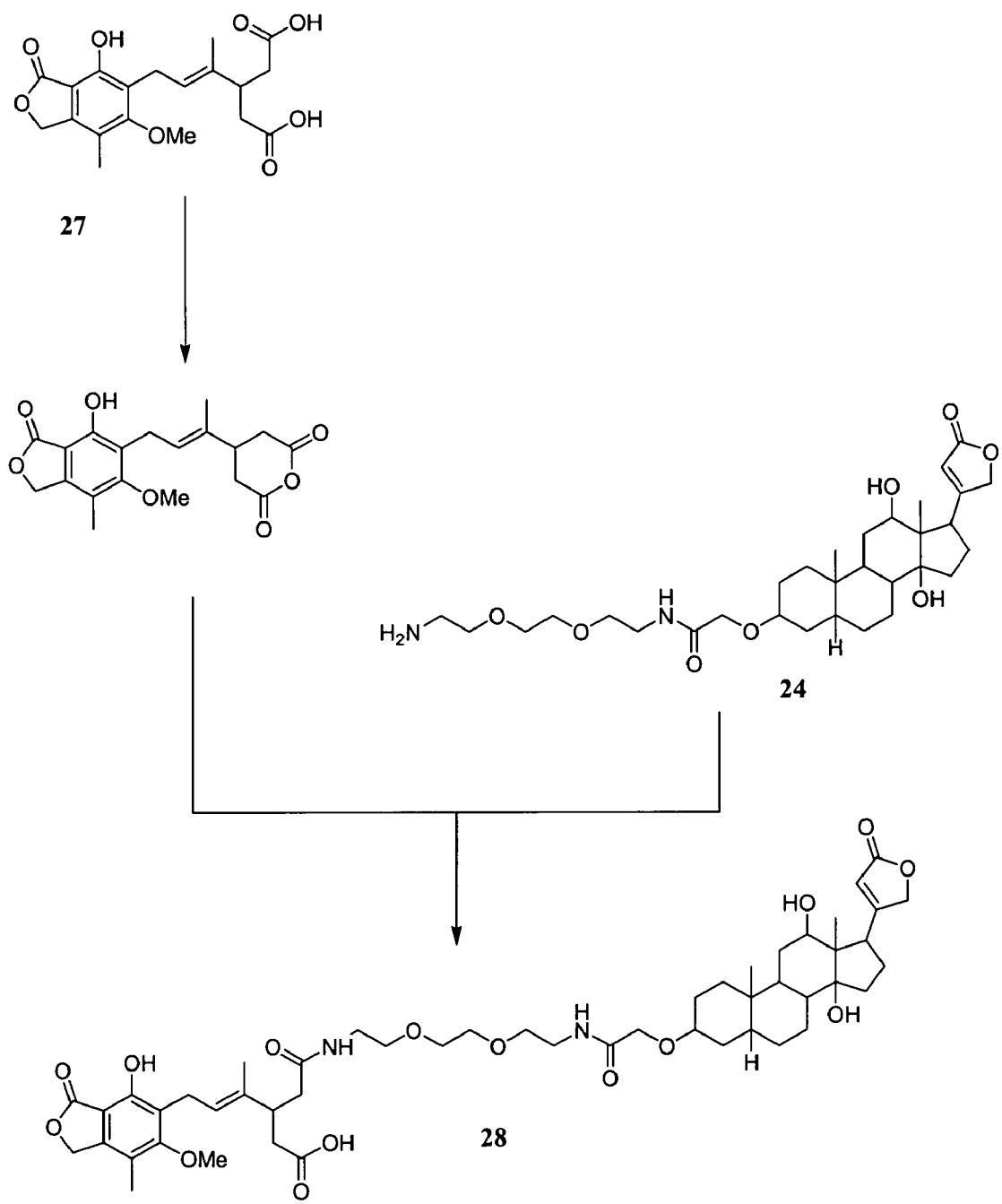
Figure 15:
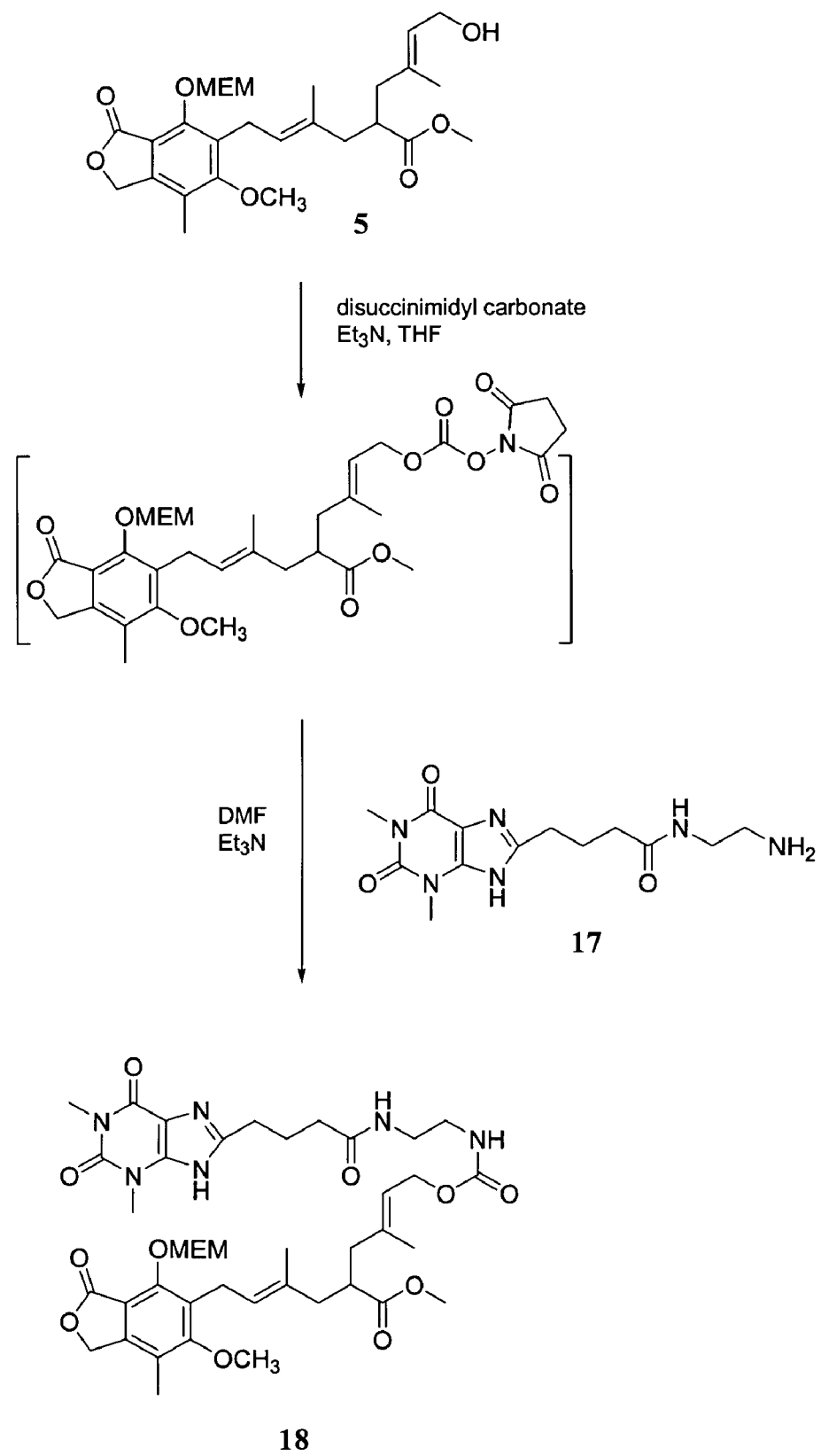
FIG. 15 illustrates the preparation of 5'-[(theophylline-8-butyramidoethylamino-carbonyloxy)-isoprenyl]-MPA [OMEM] methyl ester conjugate as described in Example 33.
Figure 16:
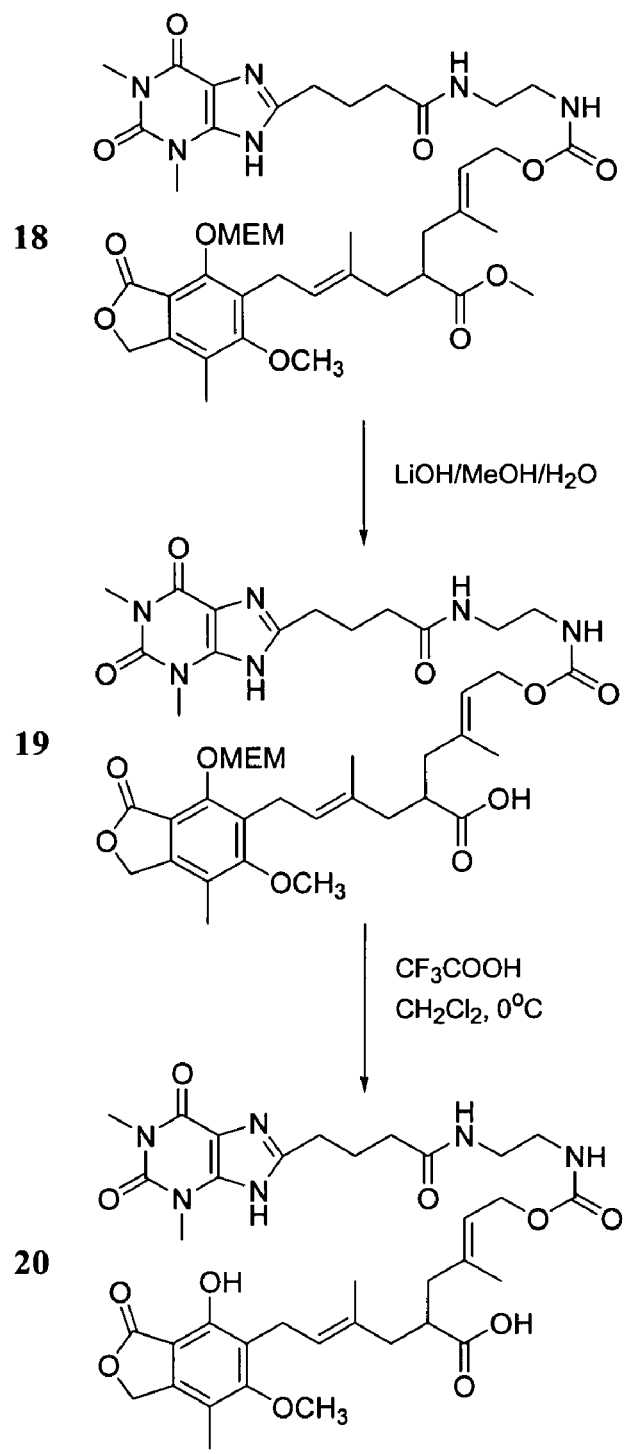
FIG. 16 illustrates the preparation of 5'-[(theophylline-8-butyramidoethylaminocarbonyloxy)-isoprenyl]-MPA as described in Example 35.
Figure 17:
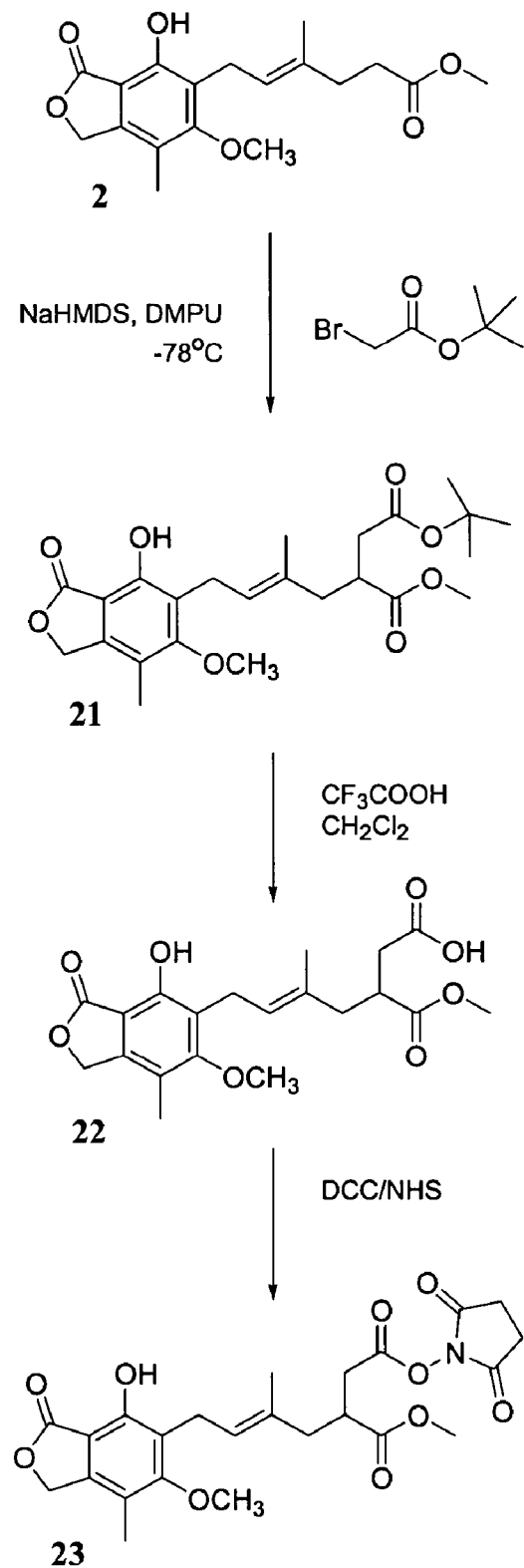
FIG. 17 illustrates the preparation of 5'-(succinimido-N-oxy)carbonylmethyl-MPA methyl ester as described in Examples 36, 37, 38 and 39.
Figure 18:
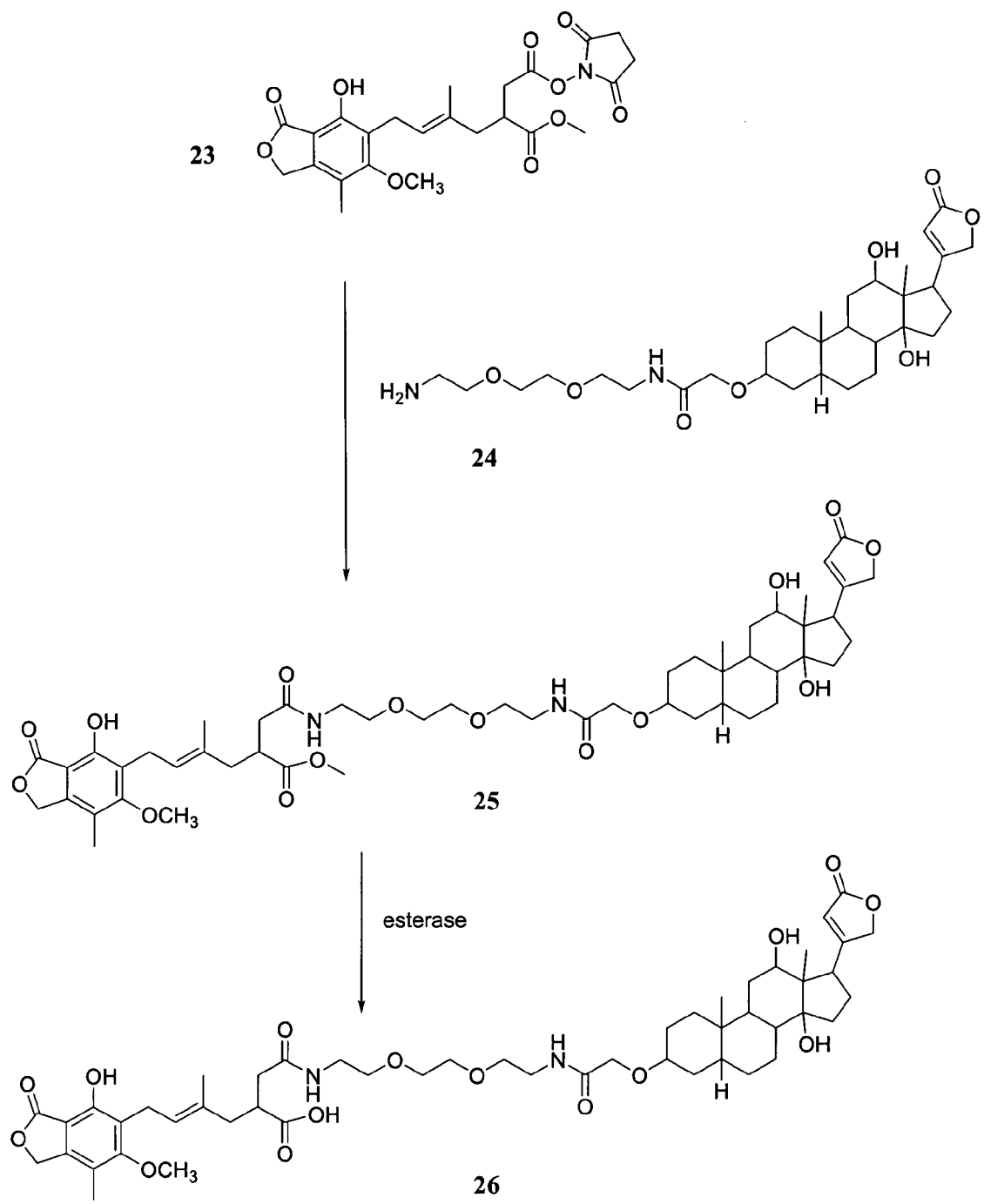
FIG. 18 illustrates the preparation of 5'-[(digoxigenin-3-yl)-oxymethylcarbonyl-DADOO-carbonylmethyl]-MPA as described in Examples 40 and 41.

Saline samples spiked with theophylline were assayed using the method of the present invention. Theophylline (Sigma Chemical) was first dissolved in saline (1 mg/10 ml) and then diluted to achieve concentrations of 0, 5, 10, 20, 40 and 50 µg/ml. An HITACHI 717 analyzer (Roche Diagnostics Corp., Indianapolis) was programmed to dispense 3 µl of sample and 150 µl of first reagent into a 37° C. cuvette, which were then mixed and incubated for 5 minutes, after which time 150 µl of second reagent was added and mixed. The difference in absorbance at 340 nm was calculated from the initial addition of the second reagent to 5 minutes following the second reagent addition. Results obtained are shown in FIG. 5.

In this example, inhibitor and antibody were combined together in the same reagent. The particular theophylline antibody used in this example had a relatively low affinity for the inhibitor compared to that for the drug, so the antibody and inhibitor were combined first before adding sample in order to pre-form the inhibitor-antibody conjugate. Then when the sample containing drug is added, the drug displaces the inhibitor, because of the higher affinity of the antibody for the drug, thereby freeing the inhibitor for inhibiting the enzyme.

EXAMPLE 30

Inhibition Constants of Ligand Inhibitors

The $IC_{50}$, inhibitor constant, is the molar concentration of inhibitor that produces 50% inhibition of enzymatic activity. This example is used to illustrate potency of enzyme inhibition by various MPA derivatives.

This assay measures the formation of NADH during the conversion of IMP to XMP by IMPDH II. The reaction is monitored using a spectrophotometer at 340 run for 10 minutes 40° C. The procedure used in this example is that described by Nelson, P. H. et al., *J. Med. Chem.* 39, 4181–4196 (1996). Inhibitors were diluted in 100% DMSO.

A reaction buffer, 100 ml, was prepared containing 125 mM Tris HCl, pH 8.0, 125 mM KCl, 3.75 mM EDTA, 125 g/ml BSA, 0.0625 mM IMP and 0.125 mM NAD. An enzyme diluent, 100 ml, was prepared containing 100 mM Tris HCl, pH 8.0, 100 mM KCl, 3.0 mM EDTA and 100/ml BSA.

The IMPDH II enzyme was diluted to 0.0065 U/ml in the enzyme diluent. The final concentration of the enzyme in the reaction cuvette was 0.00065 U/ml. Samples (derivatives) were dissolved in DMSO to 1 mg/ml. The samples were further diluted in 100% DMSO. All dilutions were prepared fresh from 1 mM stocks prepared previously.

The assay format was as follows: 800 µl of reaction buffer were added to 6 cuvettes in a spectrophotometer. 100 µl of DMSO only (control) or sample concentrations were added per conjugate/MPA derivative tested. Cuvettes with reaction buffer and sample were mixed by inverting. Cuvettes with reaction buffer and sample were allowed to incubate for 5 minutes at 40° C. Reaction was initiated with the addition of 100 µl of enzyme solution. Cuvettes were mixed again by inverting. The reactions were monitored at 340 nm and data collected for 10 minutes. The results were used to determine the $IC_{50}$s for the samples.

MPA-isoprenyl alcohol (racemic, 3A), was prepared by lithium hydroxide hydrolysis of the ester group and deprotection of the TBDPS group of compound (3) following methods known to those skilled in the art and as described in Example 5A. The chiral MPA-isoprenyl alcohol (3B), R-isomer, was made by alkylation of the [(S)-4-benzyl-2-oxazolidinon-1-yl] imide analog [Rohloff et al., *Tetrahedron Lett.*, 36, 7803–7806 (1995)] of (2), at the 5'-position, with the alkyl bromide (1) in a similar manner to that described for the synthesis of (3); followed by deprotection of the TBDPS group and hydrolysis of the oxazolidinyl group using methods known to practitioners of the art and as described in Example 5B.

TABLE 13

Inhibitor constants

| MPA Derivatives | $IC_{50}$ |
|---|---|
| MPA | $2.6 \times 10^{-8}$ M |
| MPA—MPA | $3.2 \times 10^{-8}$ M |
| MPA-isoprenyl alcohol (chiral, R enantiomer, 3B) | $1.3 \times 10^{-8}$ M |
| MPA-isoprenyl alcohol (racemic, 3A) | $4.8 \times 10^{-8}$ M |
| 5'-(digoxigenin-3-yl-β-amidomethyl)-MPA (isomer B, chiral, possibly R enantiomer, 16B) | $6.8 \times 10^{-8}$ M |
| 5'-(digoxigenin-3-yl-β-amidomethyl)-MPA (isomer A, chiral, possibly S enantiomer, 16A) | $1.7 \times 10^{-7}$ M |
| 5'-[(digoxigenin-3-yl)-oxymethyl-carbonyl-DADOO-carbonylmethyl]-MPA (racemic, 26) | $1.7 \times 10^{-7}$ M |
| 5'-[(isoprenyloxycarbonylamino-ethyleneamido)-thyroxine]-MPA (11) | $8.3 \times 10^{-8}$ M* |
| 5'-[(theophylline-8-butyramidoethyl-aminocarbonyl-oxy)isoprenyl]-MPA (20) | $2.5 \times 10^{-7}$ M* |
| 5'-[(phenytoin-3-butyramido)-isoprenyl]-MPA conjugate (Y) | $8.8 \times 10^{-8}$ M |
| 5'-[(gentamicin[Cla]-N¹-carbonyl-oxy)-isoprenyl]-MPA conjugate (R) | $6.6 \times 10^{-7}$ M |
| 5'-[(gentamicin[Cla]-N¹-terephthaloyl)-amino-isoprenyl]-MPA conjugate (amide linkage, U) | $2.7 \times 10^{-7}$ M |

This table shows the IC50 data obtained for several MPA derivatives. The $IC_{50}$ data is the molar concentration of MPA-inhibitor that reduces the enzyme activity by 50%. The $IC_{50}$ values are determined by using a non-linear curve fit of the plot of fractional activity (enzyme rate with MPA-inhibitor/enzyme rate without any MPA-inhibitor) on the y-axis vs. molar concentration of the MPA-inhibitor in the assay mixture on the x-axis. Sigma-Plot 4.0 software was used for the non-linear curve fit using the regression formula; hyperbolic decay, 2 parameters, y=ab/(b+x), where y=fractional activity, x=molar concentration of inhibitor, a=1, and b=$IC_{50}$.

The $IC_{50}$ results show the importance of chirality at the 5' position of MPA derivative inhibitors of IMPDH, and the spatial geometry of our more potent enantiomers are consistent with Smith, D. B. et.al., *Journal of Organic Chemistry* 61, 2236–2241 (1996).

The MPA-MPA derivative was used as a prototype inhibitor that had a drug (MPA) attached to the MPA parent structure. Since it was demonstrated that MPA-MPA as a prototype drug-inhibitor worked in an immunoassay for MPA, a measure of the $IC_{50}$ value for this inhibitor may be a predictor of success in an immunoassay not only for MPA but also for new drugs. Those drug inhibitors with lower $IC_{50}$ values would be more potent inhibitors of IMPDH activity and thus useful in the described immunoassay. For example, MPA-thyroxine isoprenyl had a lower $IC_{50}$ value and showed greater sensitivity in an immunoassay than MPA-theophylline. Also, chiral derivatives are more potent inhibitors of IMPDH consistent with a previous publication which reports the S enantiomer of an MPA derivative to be more potent. *J. Org. Chem.* 61, 2236–2241, (1996).

The $IC_{50}$ values for these derivatives were determined using a slightly different method. For these derivatives the enzyme rate with and without inhibitor was determined as described in Example 20 for thyroxine and Example 29 for theophylline, except no antibody was added to the second reagent and only saline was used as a sample. Multiple second reagents each containing a different concentration of inhibitor were assayed using an HITACHI 917. The first reagent was as described in Examples 20 and 29 without modification. The fractional rates obtained with these different concentrations of inhibitor were plotted vs. the molar concentration of the inhibitor and the $IC_{50}$ calculated as described.

EXAMPLE 31

Synthesis of (digoxigenin-3-yl)-oxymethylcarbonyl-DADOO (24)

1.35 g (9.2 mmol) diamino-dioxa-octane were dissolved in 1.3 ml triethylamine and 15 ml dioxane and stirred at room temperature. To this mixture a solution of 500 mg (0.92 mmol) digoxigenin-3-cme-NHS in 10 ml dioxane was added by a dropping funnel within 15 min. After 1 hour stirring at room temperature the solvent was evaporated and the crude product was dissolved in 10 ml methanol and purified with prep. RP-HPLC (Waters Delta Pak C-18 50×250 mm, water/acetonitrile/0.1% TFA). The pure fractions are pooled and lyophilized to give 520 mg oily product.

EXAMPLE 32

Synthesis of [(digoxigenin-3-yl)-oxymethylcarbonyl-DADOO-carbonylmethyl]-MPA (28)

To a solution of 41 mg (0.1084 mmol) dicarboxy MPA (27, Example 43) in 820 µl THF 8.77 µl (0.1084 mmol) pyridine and 15.3 µl trifluoroacetic anhydride were added and the mixture was stirred for 3 hours. 69.3 mg (0.1084 mmol, digoxigenin-3-yl)-oxymethylcarbonyl-DADOO dissolved in 820 µl pyridine were added and the mixture was stirred 16 hours at room temperature. The reaction mixture was diluted with 1 ml acetic acid and purified using preparative RP-HPLC (Waters Delta Pak C-18 50×250 mm, water/acetonitrile/0.1% TFA). Product containing fractions were pooled and lyophilized to give 66 mg. The product was characterized by $^1$H-NMR and MS.

EXAMPLE 33

Preparation of 5'-[(theophylline-8-butyramidoethylaminocarbonyloxy)-isoprenyl]-MPA[OMEM] methyl ester conjugate (18)

Theophylline amine (17) was prepared according to the procedure published in PCT patent application WO 87/07955 (1987).

To 23 mg (0.045 mmol) of 5'-isoprenyl[OH]-MPA [OMEM] methyl ester (5) was added 1.5 ml of THF followed by 20 mg (0.078 mmol) of N,N'-disuccinimidyl carbonate and 20 µl of triethylamine. The mixture was allowed to stir at room temperature for 18 hours to give corresponding N-hydroxysuccinimidyl carbonate.

Theophylline amine (17), 14 mg (0.045 mmol), was dissolved in 1 ml of anhydrous DMF and 100 µl of triethylamine was added. To this solution was added dropwise the previously prepared MPA-N-hydroxysuccinimidyl carbonate solution (generated in situ). The reaction mixture was allowed to stir under argon for 3 hours and concentrated under reduced pressure. The residue was purified by preparative RP-HPLC (Rainin C-18 (ODS) 21.4 mm×250 mm) using water/acetonitrile gradient system containing 0.1% trifluoroacetic acid. Product containing fractions were combined, acetonitrile was evaporated and the remaining mixture was lyophilized to give 10 mg (0.011 mmol, 26%) of (18). $^1$H-NMR compatible, LC/MS: M+H 841.3

EXAMPLE 34

Preparation of 5'-[(theophylline-8-butyramidoethylaminocarbonyloxy)-isoprenyl]-MPA[OMEM] conjugate (19)

To a solution of 11.7 mg (0.014 mmol) of 5'-[(theophylline-8-butyramidoethylaminocarbonyloxy)isoprenyl]-MPA [OMEM] methyl ester conjugate (18) in 2.4 ml of methanol stirring under argon was added a solution of 24 mg (0.572 mmol) of lithium hydroxide monohydrate in 1.2 ml of water. The reaction was stirred at room temperature under argon, monitoring by RP-HPLC (Vydac C-18; 300 Å 218TP54; 4.6 mm×250 mm; 0.1% TFA-$H_2O$/0.1% TFA-$CH_3CN$ gradient). After 4 days at room temperature consumption of starting material was almost complete, with increasing appearance of a peak at shorter retention time. The reaction mixture was acidified with dilute phosphoric acid (precipitate), concentrated to dryness, triturated with methanol and the solids filtered off. The filtrate was concentrated to dryness, the residue redissolved in $CH_3CN$—$H_2O$ (1:1) and purified by preparative RP-HPLC (Rainin C-18 (ODS) 21.4 mm×250 mm) using a 0.1% TFA-$H_2O$/0.1% TFA-$CH_3CN$ gradient. Fractions containing product were combined, acetonitrile evaporated off under reduced pressure and the residue lyophilized to give 8 mg (0.0097 mmol, 69%) of (19) as a white solid.

EXAMPLE 35

Preparation of 5'-[(theophylline-8-butyramidoethylaminocarbonyloxy)-isoprenyl]-MPA (20)

To a solution of 1.0 mg (0.0012 mmol) of 5'-[(theophylline-8-butyramidoethylaminocarbonyloxy)isoprenyl]-MPA

[OMEM] conjugate (19) in 200 µl of dry methylene chloride under argon and cooled in an ice-bath was added a chilled solution of 20 µl of trifluoroacetic acid dissolved in 40 µl of methylene chloride in 3 portions over about a minute. After stirring for 20 minutes while maintaining cooling, volatile material was evaporated off by direct aspiration under high vacuum. RP-HPLC (Vydac C-18; 300 Å 218TP54; 4.6 mm×250 mm; 0.1% TFA-H$_2$O/0.1% TFA-CH$_3$CN gradient) and $^1$H-NMR (CD$_3$OD) of the residue indicated partial formation of the desired MEM-deprotected product. The material was re-pooled, concentrated to dryness, redissolved in dry methylene chloride and re-evaporated (3×). The residue was resubjected to the TFA treatment as described above but with stirring for 35 minutes. Solvents were removed as before. RP-HPLC and $^1$H-NMR analysis of the residue indicated further formation of desired product and reduction of starting material. The repooled material was re-concentrated, treated as before and resubjected to the TFA treatment as described above for a third time, with stirring for 30 minutes. RP-HPLC analysis of the resulting reaction mixture indicated essential completeness of the reaction, with increases in by-product peaks. The reaction was concentrated to dryness, redissolved in CH$_3$CN and purified by semi-preparative RP-HPLC (Vydac C-18; 300 Å 218TP510; 0.1% TFA-H$_2$O/0.1% TFA-CH$_3$CN gradient). The fractions containing product were pooled, CH$_3$CN evaporated off under reduced pressure and the residue lyophilized to give about 0.5 mg (~0.00068 mmol, ~56%) of (20) as a white solid. $^1$H-NMR compatible, LC/MS: M+H 739.3, M+Na 761.3

EXAMPLE 36

Preparation of 5'-t-butoxycarbonylmethyl-MPA methyl ester (21)

A solution of 26 ml (26 mmol) of sodium bis(trimethylsilyl)amide (1.0 M solution in THF) was cooled in dry ice/acetone bath to −78° C. under argon atmosphere. To this cooled solution was added 2.6 ml (22 mmol) of DMPU and allowed to stir at −78° C. for 15 minutes. A solution of 2.86 g (8.56 mmol) of MPA methyl ester (2) in 45 ml of freshly distilled THF was added dropwise to the reaction mixture. The reaction mixture was allowed to stir at −78° C. for 1 hour and the color of the reaction mixture was turned from pale yellow to yellow-orange. To the reaction mixture was added 1.9 ml (912.8 mmol) of t-butyl bromoacetate and the reaction mixture was allowed to stir at −78° C. for 3 hours. The reaction was quenched with 20 ml of saturated ammonium chloride solution and the mixture was allowed to warm up to room temperature. An additional 200 ml of saturated ammonium chloride was added and the reaction mixture was extracted with 3×200 ml of ethyl acetate. The combined organic layer was washed with 300 ml of saturated ammonium chloride, dried and concentrated. The crude product was purified by silica gel column chromatography using 30% hexane in ethyl acetate to give 3.87 g of a semi-solid. A portion of this product (1.45 g) was purified by RP-HPLC (Rainin C-18 (ODS) 21.4 mm×250 mm) using a gradient system of acetonitrile/water containing 0.1% of trifluoroacetic acid in several runs. Product containing fractions were combined and acetonitrile was evaporated. The residue was lyophilized to give 669 mg (1.49 mmol, 47%) of 5'-t-butoxycarbonylmethyl-MPA methyl ester (21).

EXAMPLE 37

Preparation of 5'-carboxymethyl-MPA methyl ester (22)

To 300 mg (0.67 mmol) of 5'-t-butoxycarbonylmethyl-MPA methyl ester (21) was added 15 ml of a solution of 50% trifluoroacetic acid in dichloromethane. The mixture was allowed to stir at room temperature and concentrated. The residue was purified by silica gel column chromatography using 20% methanol in ethyl acetate to give 250 mg (0.63 mmol, 95%) of 5'-carboxymethyl-MPA methyl ester (22). $^1$H-NMR compatible, HR-FAB MS: Calc for M+Na 415.1369, Observed 415.1352

EXAMPLE 38 t-Butylester Cleavage (Alternate Method)

To a solution of 360 mg (0.8 mmol) of (21) in 3.6 ml dichloromethane 3.6 ml TFA were added and the reaction mixture was stirred for 10 minutes. 200 ml 0.5 M potassium phosphate buffer pH 7.0 was added and the mixture was extracted three times with 100 ml ethyl acetate. The organic layers were pooled, dried over magnesium sulfate and the solvent was evaporated. The product was characterized with HPLC and $^1$H-NMR.

EXAMPLE 39

Preparation of 5'-(succinimido-N-oxy)carbonylmethyl-MPA methyl ester (23)

To 200 mg crude 5'-carboxymethyl-MPA methyl ester (22), 244 mg (2.12 mmol) N-hydroxysuccinimide and 437 mg (2.12 mmol) dicyclohexylcarbodiimide dissolved in 2 ml THF were stirred for 2 hours at room temperature. The precipitated dicyclohexylurea was filtered off and the filtrate was purified using preparative RP-HPLC (Waters Delta Pak C-18 50×250 mm, water/acetonitrile/0.1% TFA).

Product containing fractions were pooled and immediately lyophilized to give 129 mg of (23). The product was characterized by $^1$H-NMR and MS. $^1$H-NMR compatible, HR-FAB MS: Calc for M+H 490.1713, Observed 490.1702

EXAMPLE 40

Preparation of 5'-[(digoxigenin-3-yl)-oxymethylcarbonyl-DADOO-carbonylmethyl]-MPA methyl ester (25)

To a solution of 166 mg (0.259 mmol, digoxigenin-3-yl)-oxymethylcarbonyl-DADOO in 3.48 ml anhydrous DMF and 179 µl triethylamine, 127 mg (0.259 mmol) of (23) in 1.74 ml anhydrous DMF were pipetted. The reaction mixture was stirred for 2 hours. Then 500 µl acetic acid were added to the solution and the mixture was purified using preparative RP-HPLC (Waters Delta Pak C-18 50×250 mm, water/acetonitrile/0.1% TFA). Product containing fractions were pooled and lyophilized to give 240 mg of (25). The product was characterized by $^1$H-NMR and MS.

EXAMPLE 41

Preparation of 5'-[(digoxigenin-3-yl)-oxymethylcarbonyl-DADOO-carbonylmethyl]-MPA (26)

mg (0.2098 mmol) 5'-[(digoxigenin-3-yl)-oxymethylcarbonyl-DADOO-carbonylmethyl]-MPA methyl ester (25) dissolved in 28.7 ml DMSO were mixed slowly with 56 ml 0.1 M potassium phosphate buffer pH 7.0. The mixture became slightly turbid. 219 µl esterase (Roche Diagnostics, Cat. No. 104698) were added and the mixture was stirred for 13 days. The precipitate was filtered and the filtrate was purified using preparative RP-HPLC (Waters Delta Pak C-18 50×250 mm, water/acetonitrile/0.1% TFA). Product containing fractions were pooled and lyophilized to give 68 mg of (26). The product was characterized by $^1$H-NMR and MS.

EXAMPLE 42

Synthesis of MPA-MPA

A solution of mycophenolic acid methyl ester (2, 1.337 g, 4 mmol) in 6 ml tetrahydrofuran under inert atmosphere was cooled to −78° C. and treated with sodium hexamethyldisilazide (9 ml, 1 M in tetrahydrofuran, 9 mmol) over 25 minutes. After 15 minutes stirring, (E)-4–1,3-dihydro-6-methoxy-4-methoxyethoxymethoxy-7-methyl-3-oxoisobenzofuran-5-yl)-2-methylbut-2-enyl bromide prepared as in U.S. Pat. No. 5,493,030 example ZA-12B (1.36 g, 3.17 mmol) was added as a solution in tetrahydrofuran (4 ml) over 15 minutes. The reaction was allowed to warm slowly to about −40° C. over 1.5 hours, then the reaction was quenched by pouring onto a mixture of ice, water, and concentrated hydrochloric acid (2 ml). Extraction of the product into ethyl acetate (2×100 ml) was followed by drying over magnesium sulfate. The organics were filtered and solvent removed using a rotary evaporator. Chromatography using 40% ethyl acetate in hexanes, then 60% ethyl acetate in hexanes, and finally 80% ethyl acetate in hexanes furnished the alkylation product as an oil (191 mg) which was used in the next reaction.

The alkylation product (190 mg) was dissolved in methanol (30 ml) and treated with 660 mg of p-toluenesulfonic acid and stirred under nitrogen at ambient temperature for 5 hours. The methanol was then removed under reduced pressure and the reaction partitioned between water and ethyl acetate. The aqueous phase was washed with 75 ml of ethyl acetate, and then the combined organic layers were dried over magnesium sulfate. Filtration was followed by solvent removal to afford 150 mg of material, which was carried on to the last step.

The ester from above was dissolved in 1:1 methanol:water and 400 mg of lithium hydroxide was added. The reaction was stirred magnetically under nitrogen for 20 hours at 60° C., then cooled and poured onto 1 M NaHSO$_4$ and extracted three times with ethyl acetate (50 ml×3). The combined organics were washed with saturated brine, then dried over magnesium sulfate. The solvent was removed under reduced pressure, then the crude product (101 mg) was obtained following recrystallization from t-butyl methyl ether/hexanes. Flash chromatography of this material using 1:1 hexanes:ethylacetate with 1% acetic acid followed by another recrystallization using ethyl acetate furnished the final product (80 mg, m.p. 146.4–147.4° C).

EXAMPLE 43

Preparation of 4'-carboxymethyl MPA (27)

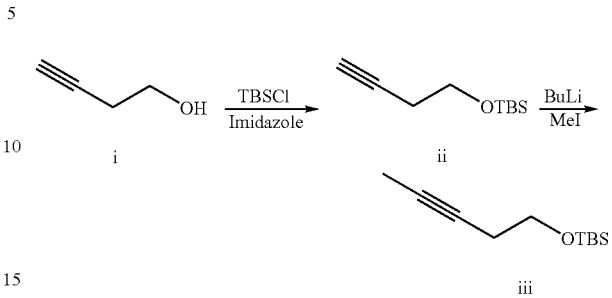

A solution of 3-butyn-1-ol (i, 10.0 g, 143 mmol, Aldrich Chemical Company) was stirred at room temperature in 200 ml dichloromethane. Imidazole (12.6 g, 186 mmol) was added, followed by tert-butyldimethylsilyl chloride (22.6 g, 150 mmol, TBSCl) and the solution stirred for 20 minutes. The reaction was diluted with methylene chloride and washed with water, 1N aqueous HCl solution, brine, and dried over magnesium sulfate. The solvent was removed in vacuo, the residue diluted with hexanes, filtered, and solvent removed in vacuo to give the silyl ether (ii) as an oil, 23.1 g, which was used without further purification.

A solution of the silyl ether (ii) prepared above (8.8 g, 48 mmol) in 200 ml tetrahydrofuran was cooled under an inert atmosphere to −78° C. and a solution of n-BuLi (31.5 ml, 50.5 ml, 1.6 M in hexanes) was added over 15 minutes by syringe. The solution was stirred at −78° C. for 1.5 hours, at which time iodomethane (67.7 g, 480 mmol) was added neat and the solution allowed to warm to room temperature overnight. 20 ml 1 N aqueous ammonium chloride solution was added, the tetrahydrofuran removed in vacuo, and the aqueous extracted twice with diethylether. The ether solution was washed twice with water, then brine, and dried over magnesium sulfate. The solvent was removed in vacuo to give 8.5 g of (iii) as an oil, which was used without further purification.

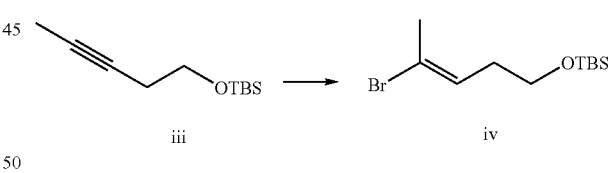

A suspension of bis(cyclopentyldienyl)zirconium dichloride (16.0 g, 55 mmol) was stirred in 100 ml THF at room temperature under an inert atmosphere. A solution of lithium triethylborohydride (55 mmol, 55 ml, 1 M in tetrahydrofuran) was added, and the solution stirred for 1 hour. A solution of the silylether (iii) prepared above (5.0 g, 27 mmol) in 10 ml of tetrahydrofuran was added via a cannula. The reaction was then heated to 50° C. for 1.5 hours, then cooled to 25° C. N-Bromosuccinimide (9.8 g, 55 mmol) was then added, the reaction stirred for 20 min. and then quenched with 50 ml 1 N sodium thiosulfate. The mixture was diluted with diethyl ether, filtered through celite, and washed successively with 1 N sodium thiosulfate and brine, then dried over magnesium sulfate. The residue obtained after removing solvents in vacuo was chromatographed over silica gel using hexanes as eluent to give the product vinyl bromide (iv) as an oil (2.1 g), which was carried on to the next step.

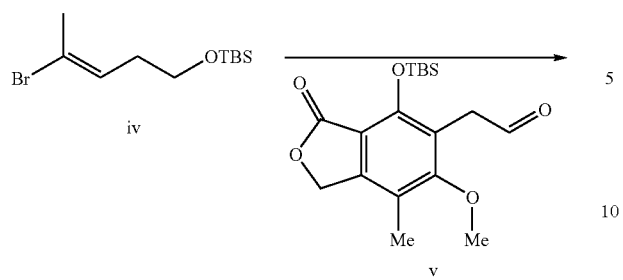

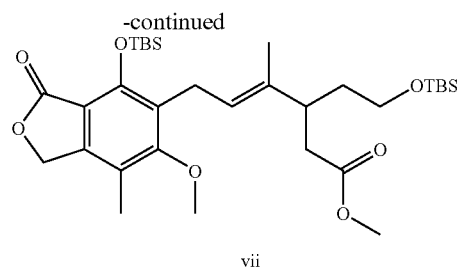

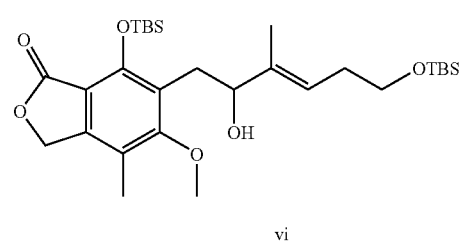

A suspension of magnesium (350 mg, 14 mmol) was stirred in a mixture of 20 ml diethyl ether and 5 ml benzene under an inert atmosphere at room temperature. To the mixture was added ethylene dibromide (2.7 g, 14.4 mmol, 1.24 ml) over 30 minutes via syringe, keeping the reaction at a gentle reflux. In a separate flask a solution of the vinyl bromide (iv, 3.65 g, 13 mmol) was stirred in 100 ml THF at −78° C. To this solution was added tert-butyllithium (27.4 mmol, 16.1 ml of a 1.7 M solution in hexanes) dropwise over 15 minutes. To the resulting vinyl lithium solution was added the solution of magnesium bromide from above via cannula over 10 minutes, and the solution stirred at −78° C. for 30 minutes to form a vinyl Grignard solution. A solution of the aldehyde (v) [Smith et al., *J. Org. Chem.* 61, 2236–2241 (1996)] (5.0 g, 14.4 mmol) in 10 ml THF was added to the vinyl Grignard solution via cannula over 5 minutes. The reaction was allowed to warm to 0° C. and stirred for 25 minutes. The reaction was then quenched with 30 ml of 1 N aqueous ammonium chloride solution, extracted with diethyl ether 3 times, and the ethereal solution washed with 1 N aqueous ammonium chloride solution, brine, and dried over magnesium sulfate. The solvent was removed in vacuo and the residue purified by chromatography over silica gel using a gradient of 10% to 20% ethyl acetate in hexanes to give 2.90 g of the allylic alcohol product (vi) as an oil.

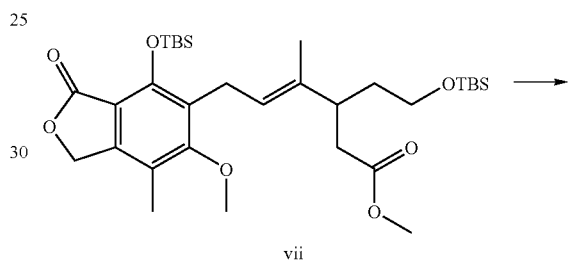

A mixture of the allylic alcohol (vi, 2.6 g, 4.7 mmol) was heated in a mixture of trimethylorthoacetate (11.4 g, 12.0 ml, 95 mmol) and pivalic acid (48 mg, 0.5 mmol) at reflux for 11 hours. The reaction was cooled and stirred at room temperature overnight. The reaction was then diluted with diethyl ether, washed with water, saturated aqueous bicarbonate solution, brine, and dried over magnesium sulfate. Solvents were removed in vacuo and the residue chromatographed over silica gel using 15% ethyl acetate in hexanes as eluent to give 1.5 g of the methyl ester product (vii) as an oil.

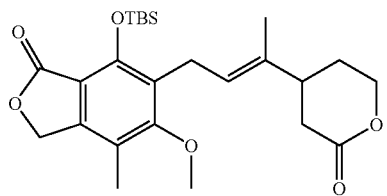

A solution of the methyl ester (vii, 1.5 g, 2.5 mmol) in 50 ml acetonitrile was stirred at room temperature. A solution of 5 ml of 40% HF solution diluted in 50 ml acetonitrile was added and the reaction stirred for 5 minutes. The solvent was removed in vacuo. The residue was dissolved in diethyl ether, washed 3 times with saturated aqueous bicarbonate, then brine, and dried over magnesium sulfate. Solvents were removed to give 1.0 g of the lactone (viii) as an oil which was used without further purification.

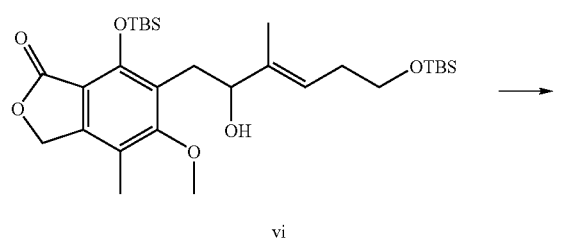

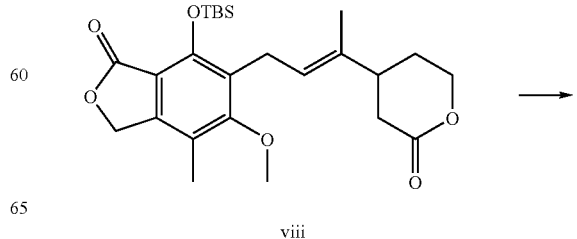

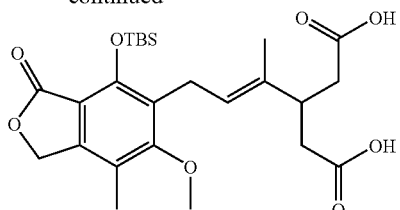

ix

A solution of the lactone (viii, 1.0 g, 2.0 mmol) was dissolved in 10 ml acetone and cooled to 0° C. To the solution was added Jones reagent (1.2 ml, 3.6 mmol, of a 3 M aqueous solution) and the reaction stirred for 45 minutes. The reaction was quenched with 3 ml methanol, diluted with ethyl acetate, washed with 1 N aqueous hydrochloric acid, water 2 times, brine, and dried over magnesium sulfate. Solvents were removed in vacuo and the residue was chromatographed on silica gel using 35% ethyl acetate and 1% acetic acid in hexanes as eluent to give 463 mg of the protected diacid (ix) as an oil.

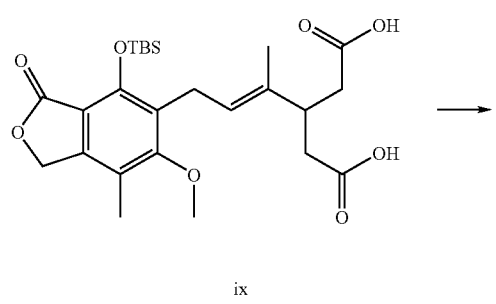

ix

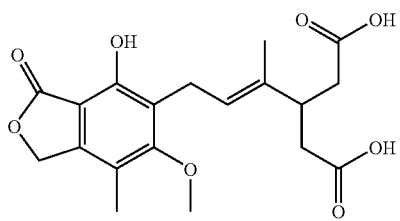

27

The protected diacid (ix, 401 mg, 0.8 mmol) was stirred in 10 ml methanol at room temperature. Lithium hydroxide hydrate was dissolved in a solution of 10 ml methanol and 2 ml water and added to the solution of diacid, and the reaction stirred for 3.5 hours. The reaction was quenched with 10 ml 1 N aqueous hydrochloric acid, extracted with ethyl acetate 3 times, the ethyl acetate layers combined and washed with brine. Solvents were removed and the solid so obtained was triturated with a mixture of diethyl ether and hexanes. The resulting solid was recrystallized from methylene chloride/hexanes to give 201 mg of 4'-carboxymethyl MPA (27), m.p..=178° C.

EXAMPLE 44

Preparation of 5'-isoprenyl[phthalimide]-MPA(OMEM) methyl ester (A)

To 144 mg (0.28 mmol) of 5'-isoprenyl[OH]-MPA [OMEM] methyl ester (i) was added 10 mL of freshly distilled THF followed by 96 mg (0.36 mmol) of triphenylphosphine, 53 mg (0.36 mmol) of phthalimide and 72 µL (0.36 mmol) of diisopropylazodicarboxylate. The reaction mixture was allowed to stir at room temperature for 18 hours and reaction progress was monitored by thin layer chromatography (TLC) using 50% ethyl acetate in hexane. TLC analysis indicated the formation of desired product and the presence of a significant amount of starting MPA alcohol (5) in the reaction mixture. To the reaction mixture was added an additional 96 mg (0.36 mmol) of triphenylphosphine, 53 mg (0.36 mmol) of phthalimide, 72 µL (0.36 mmol) of diisopropylazodicarboxylate and 1 g of 4A molecular sieves. The reaction mixture was allowed to stir at room temperature for 18 hours and concentrated to dryness under reduced pressure. The residue was dissolved in 100 mL of ethyl acetate and was washed with 2×50 mL of water. The organic layer was dried ($Na_2SO_4$) and concentrated. The residue was purified by silica gel flash column chromatography using 50% ethyl acetate in hexane to give 151 mg (0.24 mmol, 84%) of (A) as a thick, colorless gum. $^1$H-NMR: compatible. HR-ES (+) MS: Calcd M+Na 658.2622, Observed 658.2617.

EXAMPLE 45

Preparation of MPA[OMEM]-5'-isoprenylamine methyl ester (B)

To 165 mg (0.25 mmol) of (A), from Example 44, was added 4 mL of 2 M methylamine in methanol. The mixture was allowed to stir at room temperature for 18 hours and then concentrated. The residue was purified by silica gel column chromatography using 80% chloroform in methanol as eluent to give 70 mg (0.14 mmol, 53%) of (B) as a thick, colorless gum. $^1$H-NMR: compatible. HR-ES (+) MS: Calcd M+H 506.2749, Observed 506.2750.

EXAMPLE 46

Deprotection of MPA[OMEM]-5'-isoprenylamine methyl ester (B) to MPA-5'-isoprenylamine (D)

To a solution of MPA[OMEM]-5'-isoprenylamine methyl ester (B, 24 mg) in methanol (MeOH, 1 mL) was added a solution of lithium hydroxide (LiOH) monohydrate (25 mg) in 1 mL of deionized water and the mixture stirred at room temperature (room temperature) under argon for 3 days. The reaction was followed by analytical RP-LC/MS, which showed the gradual disappearance of starting material and the appearance of the corresponding MPA[OMEM]-5'-isoprenylamine (C), together with a faster-running substance (molecular ion=C+18) assigned as the lactone-opened substance (Ca). The mixture was then acidified with 1N HCl to about pH 0–1 and stirred at room temperature. Analytical LC/MS showed the disappearance of the peak assigned as (Ca), presumably due to re-closure of the lactone ring, with gradual deprotection of the methoxyethoxymethyl (MEM) group to give the desired fully deprotected material (D). The deprotection was completed by concentration of the mixture under reduced pressure (rotavap) to remove methanol, followed by further concentration under high vacuum (rotovap with a dry-ice/acetone condenser) to give crude (D) as a slightly sticky solid. The material was redissolved in 1:1 acetonitrile (MeCN) and water and purified by preparative RP-HPLC (gradient of 5% increasing to 100% over 20 min of [0.1% trifluoroacetic acid (TFA)/MeCN] in [0.1% TFA/water]; flow rate=20 mL/min) to give, in two fractions after lyophilization, (D, 10.9 mg) assigned as the trifluoroacetic acid salt as a white solid. $^1$H-NMR: compatible. LC/MS: M+H 404.2.

In another experiment, after the hydrolysis of 25 mg of (B) with 25 mg of lithium hydroxide in 1 mL water +1 mL methanol as described above in (i) but with stirring for 5 days, the reaction was neutralized with 1N phosphoric acid to about pH 7. Analytical LC/MS showed the persistence of the two peaks corresponding to (C) and the assigned (Ca) as described in (i) above. The mixture was diluted with MeCN and a little water (both containing 0.1% TFA) and purified by preparative RP-HPLC, using the same solvents and gradient as described above. The elution profile indicated that (Ca) was now missing or greatly reduced, ascribed to reclosure of the lactone under the stronger acidic conditions. The appropriate fractions were isolated and lyophilized to give purified MPA[OMEM]-5'-isoprenylamine (C, 16.7 mg) as a white solid, assigned as the trifluoroacetic acid salt. $^1$H-NMR: compatible. LC/MS: M+H 492.2.

In another experiment, after treatment of (B, 25 mg) with LiOH (25 mg) in MeOH-water in an identical manner to that described above, the reaction was acidified to about pH 2 with 1N HCl. Evaporation to dryness under high vacuum gave a residue shown by analytical LC/MS to contain a mixture of the fully deprotected (D) [major] and the OMEM protected (C). The residue was dissolved in a mixture of dry $CH_2Cl_2$ (800 μL) and TFA (200 μL) and stirred for 0.5 hours at room temperature. Evaporation, redissolution in dry $CH_2Cl_2$ and re-evaporation gave a reside now shown by analytical LC/MS to contain the desired fully deprotected (D) [major] together with many others and two main impurities, both faster-running, one of which had the same molecular ion in the LC/MS as the desired (D). Preparative RP-HPLC on a portion of the mixture gave, after isolation of the appropriate fractions and lyophilization: (D, $^1$H-NMR: compatible; LC/MS: M+H 404.2) and the faster-running impurity which had LC/MS: M+H 404.2; and a $^1$H-NMR spectrum indicative of closure of the acid group onto one of the isoprenyl double bonds to form a second lactone.

EXAMPLE 47

Preparation of digoxin-MPA conjugate, 5'-[[[[(digoxin(1,4-oxazepin))4-yl]-phenyl-4-carbonyl]amino]isoprenyl]-MPA conjugate (H)

Digoxin dialdehyde (E) was synthesized from digoxin by oxidation with sodium periodate in aqueous ethanol following the analogous procedure used with digitoxin, as described by Satoh & Aoyama (D. Satoh and K. Aoyama Chem. Pharm. Bull. (Jpn), 1970,18, 94–99).

para-Aminobenzoic acid (0.221 g, 1.61 mmol) was dissolved in a total of 3 mL of methanol which was then diluted with 3 mL of 0.3 M acetic acid in water. The resulting solution was added to a stirring solution of digoxin dialdehyde (E, 1.0 g, 1.28 mmol) in methanol (20 mL) under argon. To the resulting yellow mixture was added a solution of sodium cyanoborohydride ($NaCNBH_3$, 0.11 g, 1.75 mmol) in a total of 4 mL of 0.3 M acetic acid in water. After stirring overnight at room temperature, thin layer chromatography (TLC) indicated the reaction was complete. The clear reaction mixture was evaporated to dryness under reduced pressure (at less than 30° C). The off-white solid residue was partitioned between methylene chloride ($CH_2Cl_2$) and 0.1 N aqueous HCl. The layers were separated, the organic phase washed sequentially with 0.1 N HCl (×2), water (×1), sat. aq. NaCl (×1), dried ($Na_2SO_4$), filtered, evaporated under reduced pressure and dried under high vacuum (manifold) to furnish crude product (1.06 g) as a white solid. The material was redissolved in chloroform ($CHCl_3$)-MeOH and purified by column chromatography on silica gel prepacked in 10% MeOH in $CHCl_3$ and eluting with 10% MeOH in $CHCl_3$. Appropriate fractions containing product were combined to give a fore-cut fraction of product (F, 75 mg, 6.6%) containing traces of a front-running impurity; and the main pool of product [(digoxin (1,4-oxazepin))-4-yl]-phenyl-4-carboxylic acid (F, 585 mg, 52%). $^1$H-NMR: compatible. LR (+) SIMS MS: compatible. HR-FAB MS: Calc M+H 883.4718, Observed 883.4702. UV (MeOH): λ221 (ε17,384), 307 (ε22,621) nm. Microanalysis: Calc for $C_{48}H_{69}NO_{14}$·⅝$CHCl_3$:C, 57.25; H, 6.85; N, 1.36%. Found: C, 57.11; H, 6.90; N, 1.25%.

To a stirring solution of (F, 600 mg, 0.679 mmol) in dry $CH_2Cl_2$ (60 mL) under argon was added N-hydroxysuccinimide (NHS, 102 mg, 0.886 mmol) followed by 1-ethyl-3-dimethylaminopropyl-carbodiimide hydrochloride (ED-C.HCl, 170 mg, 0.886 mmol) and the mixture stirred at room temperature under argon for 16 hours. TLC analysis indicated that the reaction was complete. The clear reaction mixture was diluted with $CH_2Cl_2$ and washed sequentially with 0.1 N HCl (×4), water (×1), sat. aq. sodium bicarbonate ($NaHCO_3$, ×4), sat. aq. NaCl (×1), dried ($Na_2SO_4$), filtered, evaporated under reduced pressure, and dried under high vacuum to give crude product (634 mg) as a white foam. The material was redissolved in a minimum volume of approx. 9:1 ethyl acetate (EtOAc)/hexanes and purified by column chromatography on silica gel (80 g) prepacked in 75% EtOAc in hexanes, eluting first with 75% EtOAc in hexanes, then with EtOAc alone. The main cut of fractions containing product were combined and evaporated under reduced pressure. The residue was re-dissolved in dry, distilled, $CH_2Cl_2$ and re-evaporated to dryness, repeating the process 6–7 times, and finally dried under high vacuum (manifold) overnight at room temperature to give the desired NHS ester, [(digoxin(1,4-oxazepin))-4-yl]-phenyl-4-carboxylic acid N-hydroxysuccinimide ester (G, 475 mg, 71%) as a white solid. $^1$H-NMR: compatible. LR (+) SIMS MS: compatible. HR FAB MS: Calc M+Na 1003.4780, Observed 1003.4767. UV (MeOH): λ216 (ε23,907), 324 (ε38,186) nm. Microanalysis: Calc for $C_{52}H_{72}N_2O_{16}$·½$CH_2Cl_2$·¼$H_2O$:C, 61.33; H, 7.21; N, 2.72%. Found: 61.31; H, 7.21; N, 2.63%.

Fully deprotected MPA-5'-isoprenylamine (D), as the trifluoroacetate salt (3.3 mg, 0.0064 mmol) and the NHS ester (G, 7.0 mg, 0.0071 mmol) were dissolved together in dry $CH_2Cl_2$ (200 μL) in a 1 mL capacity reaction vial (Wheaton Reacti-Vial) with a v-shaped cavity, and also containing a small v-shaped stir bar. Triethylamine ($Et_3N$, 5 μL, approx. 0.36 mmol) was added, the vial tightly capped (teflon-lined screw cap) and the reaction stirred for 2.5 d at room temperature. Analytical LC/MS indicated that the reaction was complete. The reaction was diluted with a little $CH_2Cl_2$ and purified directly by thin-layer chromatography (4 plates, 20×20 cm×0.025 cm silica thickness; E.M. Science, Cat.# 5715-7), eluting with 10% MeOH in $CHCl_3$. The product band ($R_f$ approx. 0.27) was cut out, ground up, and washed/eluted (sintered glass funnel) with 25% MeOH in $CHCl_3$. The collected washings were evaporated to dryness, taken up in a little 10% MeOH in $CH_2Cl_2$, filtered (Gelman Laboratory, GHP Acrodisc 25 mm syringe filter, 0.45 μm GHP membrane, part# 4560T), evaporated to dryness, redissolved in dry $CH_2Cl_2$ and re-evaporated (repeated ×2) and dried under high vacuum (manifold) to give the digoxin- MPA conjugate (H, 4.2 mg, 52%) as a white solid. $^1$H-NMR: compatible. LC/MS: M+H 1269.6, M+Na 1291.6.

EXAMPLE 48

Preparation of digitoxin-MPA conjugate, 5'-[[[[(digitoxin(1,4-oxazepin))4-yl]-phenyl-4-carbonyl]amino]isoprenyl]-MPA conjugate (L)

Digitoxin dialdehyde (I) was prepared from digitoxin by oxidation with sodium periodate in aqueous ethanol following the method of Satoh & Aoyama (D. Satoh and K. Aoyama *Chem. Pharm. Bull.* (*Jpn*), 1970, 18, 94–99).

Digitoxin dialdehyde (I, 1.0 g, 1.31 mmol) in MeOH (20 mL) was reacted with para-aminobenzoic acid (220 mg, 1.60 mmol; dissolved in 6 mL 1:1 MeOH-0.3 M HOAc in water) and NaCNBH$_3$ (108 mg, 1.72 mmol; dissolved in 3 mL 0.3 M HOAc in water) in a similar manner to Example 47(ii), for 1.5 hours. Additional NaCNBH$_3$ (52 mg, 0.83 mmol) was added, and after a total of 4.33 hours, TLC analysis indicated the reaction was complete. The reaction was worked up and purified by silica gel chromatography in a similar manner to that described in Example 47(ii) to give, from the main cut of chromatography fractions, [(digitoxin(1,4-oxazepin))-4-yl]-phenyl-4-carboxylic acid (J, 443 mg, 39%). $^1$H-NMR: compatible. LR (+) SIMS MS: compatible. HR FAB MS: Calc M+867.4769, Observed 867.4798. WV (MeOH): λ220 (ε18,094), 308 (ε23,364) nm. Microanalysis: Calc for C$_{48}$H$_{69}$NO$_{13}$·CHCl$_3$·⅓H$_2$O:C, 59.24; H, 7.17; N, 1.41%. Found: C, 59.11; H, 7.09; N, 1.32%. Less pure material (301 mg) was obtained from the later fractions.

Reaction of the acid (J, 535 mg, 0.616 mmol) with NHS (92 mg, 0.80 mmol) and EDC.HCl (154 mg, 0.80 mmol) in dry CH$_2$Cl$_2$ (40 mL) overnight at room temperature under argon in a similar manner to Example 47(iii) followed by work-up and purification by silica gel chromatography in a similar manner to that described in Example 47(iii) gave, from the appropriate fractions after evaporation and drying under high vacuum the desired NHS ester, [(digitoxin(1,4-oxazepin))-4-yl]-phenyl-4-carboxylic acid N-hydroxysuccinimide ester (K, 423 mg, 71%) as a white solid. $^1$H-NMR: compatible. LR (+) SIMS MS: compatible. HR FAB MS: Calc M$^+$964.4933, Observed 964.4945. UV (MeOH): λ216 (ε18,639), 324 (ε37,261) nm. Microanalysis: Calc for C$_{52}$H$_{72}$N$_2$O$_{15}$·⅕EtOAc.⅖CH$_2$Cl$_2$:C, 62.85; H, 7.38; N, 2.76%. Found: C, 62.97; H, 7.27; N, 2.82%.

A suspension of fully deprotected MPA-5'-isoprenylamine (D), as the trifluoroacetate salt (3.4 mg, 0.0066 mmol), and the NHS ester (K, 7.0 mg, 0.0073 mmol) in dry CH$_2$Cl$_2$ (1 mL) containing Et$_3$N (5 µL, approx. 0.036 mmol) was stirred at room temperature under argon for approx. 24 hours. Analytical LC/MS of the slightly cloudy mixture indicated both starting materials were still present, together with the desired product. Dry dimethylformamide (DMF) was added and the reaction stirred for an additional 24 hours, after which LC/MS indicated the reaction was essentially complete. The reaction was evaporated to dryness under reduced pressure, then under high vacuum. The residue was redissolved in a little 10% MeOH in CHCl$_3$ and purified by thin-layer chromatography (4 plates, 20×20 cm×0.025 cm silica thickness; E.M. Science, Cat.# 5715-7), eluting with 10% MeOH in CHCl$_3$. The product band (R$_f$ approx. 0.39) was cut out, ground up, and washed/eluted (sintered glass funnel) with 25% MeOH in CHCl$_3$. The collected washings were evaporated to dryness, taken up in a little 10% MeOH in CH$_2$Cl$_2$, filtered (Gelman Laboratory, GHP Acrodisc 25 mm syringe filter, 0.45 µm GHP membrane, part# 4560T), evaporated to dryness, redissolved in dry CH$_2$Cl$_2$ and re-evaporated (repeated ×3) and dried under high vacuum (manifold) to give the digitoxin-MPA conjugate (L, 5.2 mg, 63%) as a white solid. $^1$H-NMR: compatible. LC/MS: M+H 1253.8, M+Na 1275.6.

EXAMPLE 49

Preparation of fully protected gentamicin-MPA conjugate (carbamate linkage), 5'-[(N2',N3,N6'-tri-tbutoxycarbonyl-N3"-trifluoroacetyl-gentamicin [C1a]-N1-carbonyl-oxy)-isoprenyl]-MPA[OMEM] methyl ester conjugate (N)

To 20 mg (0.039 mmol) of 5'-isoprenyl[OH]-MPA [OMEM] methyl ester (5) was added 1 mL of THF followed by 10.1 mg (0.039 mmol) of N, N'-disuccinimidyl carbonate and 25 µL of triethylamine. The mixture was allowed to stir at room temperature for 18 hours to give the corresponding N-hydroxysuccinimidyl carbonate.

To 550 mg (1.22 mmol) of gentamicin C1A was added 35 mL of anhydrous DMF, followed by 1.04 g (4.74 mmol) of zinc acetate dihydrate. The mixture was stirred at room temperature under an argon atmosphere for 5 days. To the reaction mixture was added 850 mg (3.89 mmol) of di-t-butyl dicarbonate, and the resulting mixture was stirred at room temperature for 3 days. The reaction mixture was then concentrated under reduced pressure and purified by column chromatography. The crude material was dissolved in a minimum amount of the same solvent used as an eluent in the column. The column was eluted with CHCl$_3$—MeOH-28% NH$_4$OH (7:3:0.1). The fractions from the column were analyzed by thin layer chromatography (TLC), using the same solvent system used in the column. The plates were developed by dipping the plate in a phosphomolybdic acid solution, followed by heating on a hot plate. The retardation factor (Rf) of the product in CHCl$_3$—MeOH—28% NH$_4$OH (7:3:0.1) was 0.27. The desired fractions were combined and concentrated. The residue was then suspended in 25 mL of dichloromethane and concentrated. The suspension in dichloromethane and concentration procedure was repeated twice more to give 481 mg (0.62 mmol, 51%) of 3,2',6'-tri-t-butoxycarbonyl gentamicin C1a as a white powder.

To 460 mg (0.602 mmol) of 3,2',6'-tri-t-butoxycarbonyl gentamicin C1a was added 9 mL of anhydrous DMSO, followed by 81 µL (0.70 mmol) of ethyltrifluoroacetate. The mixture was allowed to stir at room temperature for 3 days and then concentrated under reduced pressure. During the concentration, the temperature of the water bath was maintained below 45° C. The residue was purified by silica gel column chromatography using a 9:1 mixture of CHCl$_3$ and methanol as eluent. The fractions coming out of the column were analyzed by TLC using the same solvent system. The plates were developed by dipping the plate in phosphomolybdic acid solution, followed by heating on a hot plate. The Rf of the product in the 9:1 mixture of CHCl$_3$ and methanol was 0.30. The desired fractions were combined and concentrated. The residue was suspended in 20 mL of dichloromethane and was then concentrated. The suspension in dichloromethane and concentration procedure was repeated twice more to give 480 mg (0.55 mmol, 93%) of 3,2',6'-tri-t-butoxycarbonyl-3"-N-(trifluoroacetyl)gentamicin C1a (Z1) as a white powder.

A solution of 16 mg (0.019 mmol) of the gentamicin amine: 2',3,6'-tri-t-butoxycarbonyl-3"-(N-trifluoroacetyl)-gentamicin[C1a] (Z1) was prepared in 1 mL of anhydrous DMF and 100 µL of triethylamine was added. To this solution was added dropwise the previously prepared MPA-N-hydroxysuccinimidyl carbonate solution (generated in situ). The reaction mixture was allowed to stir under argon for 4 hours and concentrated under reduced pressure. The residue was purified by preparative RP-HPLC using a water/ acetonitrile gradient system containing 0.1% trifluoroacetic acid. Fractions containing product were combined and lyophilized to give 15 mg (0.010 mmol, 57%) of protected gentamicin-MPA conjugate (N). $^1$H-NMR: compatible. HR (+) ES MS: Calcd M+Na 1400.6446, Observed 1400.6495.

EXAMPLE 50

Deprotection of the fully protected gentamicin-MPA conjugate, 5'-[(N2',N3,N6'-tri-tbutoxycarbonyl-N3"-trifluoroacetyl-gentamicin[C1a]-N1-carbonyl-oxy)-isoprenyl]-MPA[OMEM] methyl ester conjugate (N); to the gentamicin-MPA conjugate, 5'-[(gentamicin[C1a]-N1-carbonyl-oxy)-isoprenyl]-MPA conjugate (R)

Figure 23A:
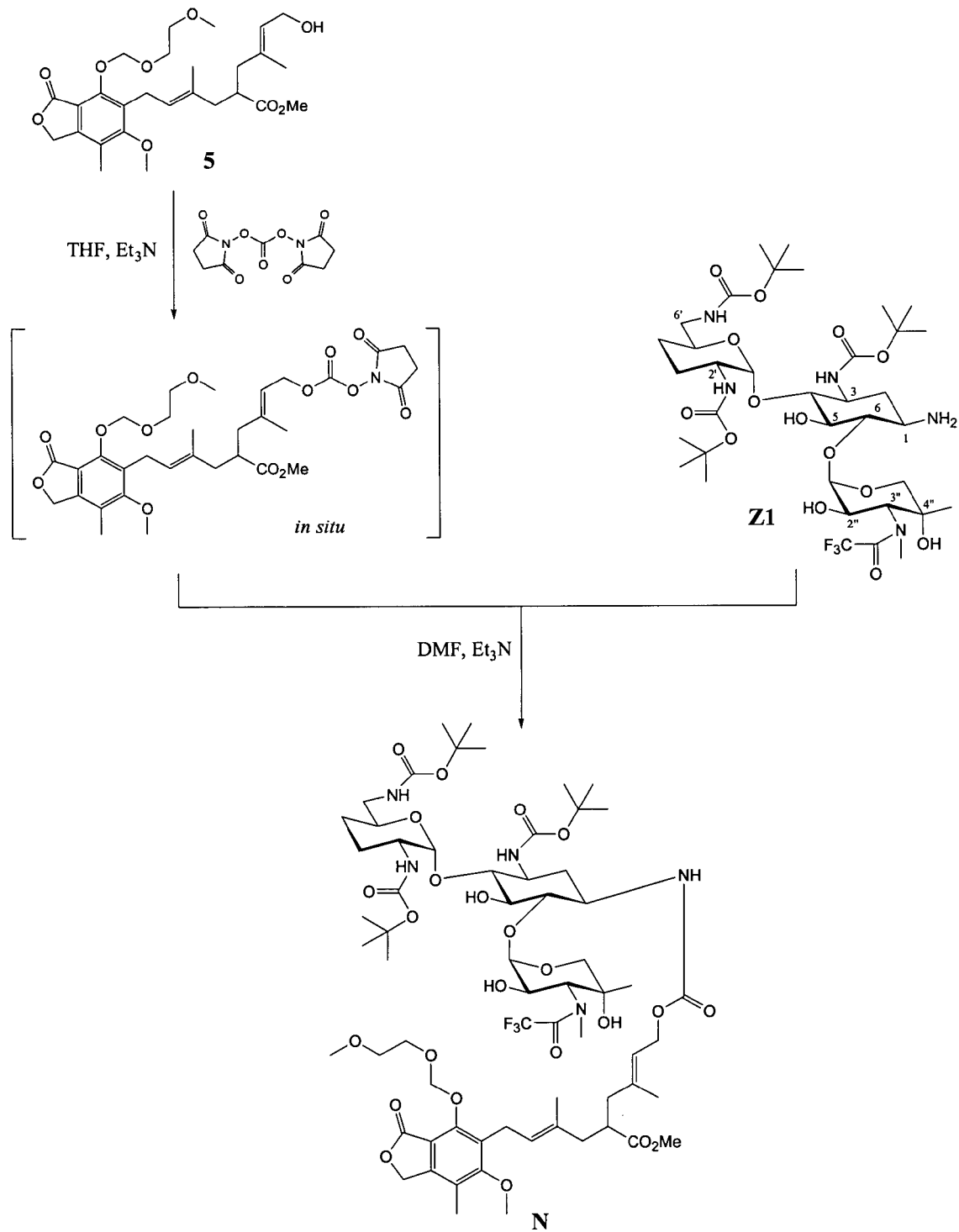
FIGS. 23a and 23b illustrate the preparation of 5'-[(gentamicin[C1a]-N$^1$-carbonyl-oxy)-isoprenyl]-MPA conjugate (R) as described in Examples 49, 50 and 51
Figure 23B:
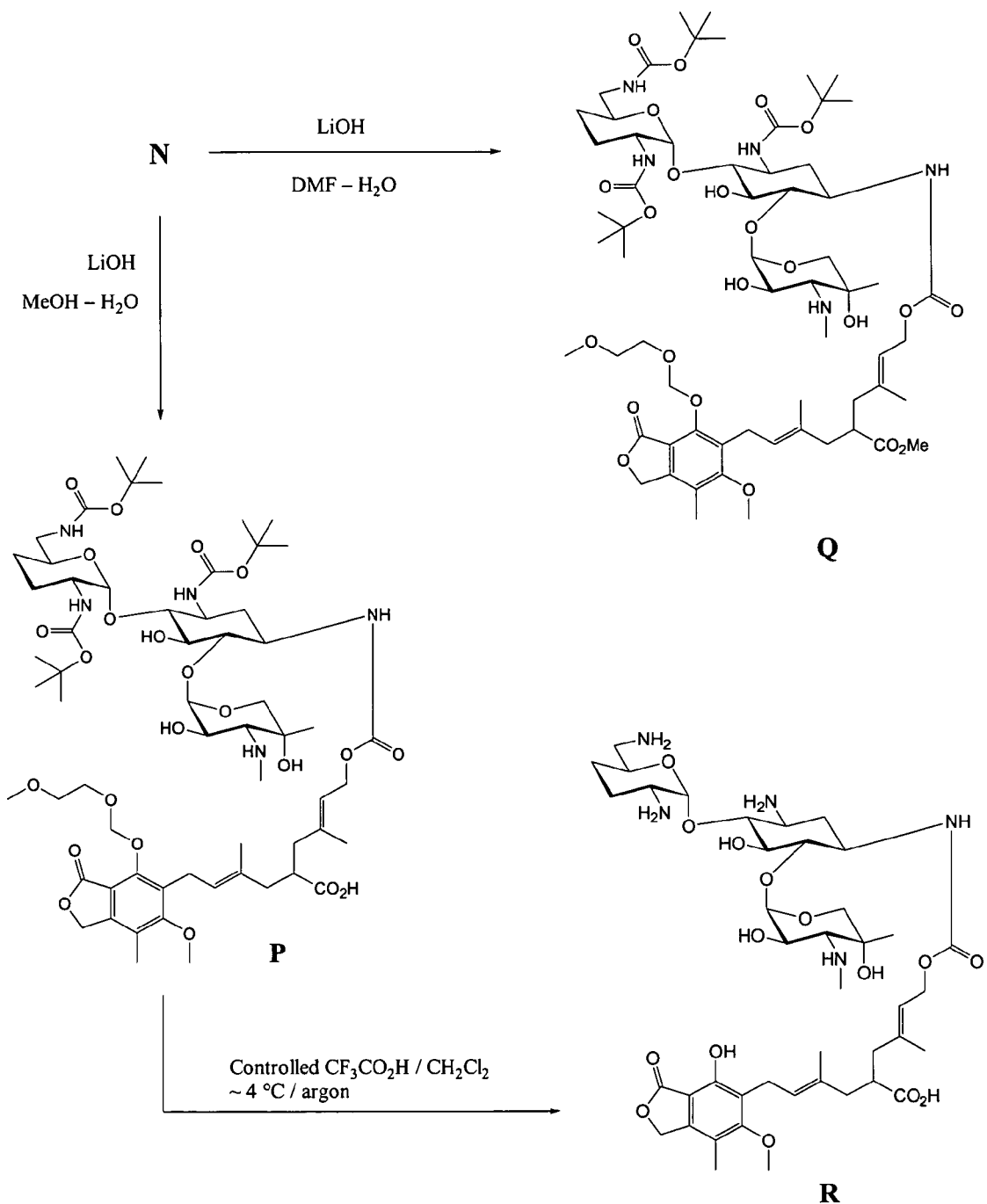

With reference to FIGS. 23a and 23b, fully protected gentamicin-MPA conjugate (N, 1.0 mg, 0.73 μmol) was dissolved in MeOH (200 μL) in a 0.5 mL capacity vial with a V-shaped well (Wheaton Reacti-Vial) additionally containing a v-shaped stir-bar. A solution of lithium hydroxide in water (100 μL of a [20 mg/mL of LiOH monohydrate in water], equivalent to 2 mg of LiOH) was added. The vial was tightly capped and the clear solution stirred at room temperature. Analytical HPLC showed gradual progression of the reaction through a faster running peak assigned as the intermediate (Q), into the yet-faster running peak assigned as the intermediate (P). After 3 d at room temperature, analytical HPLC indicated the reaction to be comprised of very largely compound (P). The reaction was carefully adjusted to pH approx. 6 with dilute phosphoric acid (1 drop of 85% $H_3PO_4$ in 2 mL water), with a small amount of solid (lithium phosphate) being precipitated. The mixture was evaporated to dryness under high vacuum. The residue was triturated with MeOH, filtered, the filtrate evaporated under reduced pressure, the residue redissolved in a little 1:1 MeCN-water and purified by semi-preparative RP-HPLC (Column: Vydac 218TP510; 300 Å, 5μ, C18, 10×250 mm. Guard: Vydac 218GK54. Gradient: 5% [C=MeCN containing 0.1% TFA] at 0 min, rising to 50% C at 10 min, rising to 75% C at 30 min, rising to 100% C at 35 min, then falling to 5% C at 40 min; in [A=water containing 0.1% TFA]; flow rate=3 mL/min). The peaks containing desired product (retention time [tR]~20 min) were collected and lyophilized to give 5'-[(N$^{2'}$,N$^3$,N$^{6'}$-tri-$^t$butoxycarbonyl-gentamicin[C1a]-N$^1$-carbonyl-oxy)-isoprenyl]-MPA[OMEM] (P, 0.5 mg) as a white solid. $^1$H-NMR: compatible. LC/MS: M+H 1268.6.

In another experiment, 3.0 mg of (N) in 500 μL of MeOH was treated with 5 mg of LiOH in 250 μL of water in a similar manner as described above for 3 d at room temperature. Work-up as described above gave a residue that was purified by analytical TLC (20×20 cm; 0.025 cm silica thickness; 2 plates), eluting with 15% MeOH in CHCl$_3$. The product band (Rf~0.4) was cut out, the silica washed/eluted with 30% MeOH in CHCl$_3$, the washings evaporated to dryness and the residue repurified by semi-preparative HPLC as described above. The product peaks were collected and lyophilized to give the intermediate gentamicin[(BOC)$_3$] [NHMe]-MPA[OMEM][COOH] (P, 1.1 mg) as a white solid. $^1$H-NMR: compatible.

5'-[(N$^{2'}$,N$^3$,N$^{6'}$-tri-$^t$butoxycarbonyl-gentamicin[C1a]-N1-carbonyl-oxy)-isoprenyl]-MPA[OMEM] conjugate (P, 1.1 mg) was dissolved in dry CH$_2$Cl$_2$ (200 μL) under argon and with cooling in an ice-water bath (~4° C.). To the stirring solution (micro magnetic stir-bar) was added a solution of trifluoroacetic acid (TFA, 20 μL) in dry CH$_2$Cl$_2$ (60 μL) in three portions over ~1 min. and the reaction stirred for 10 min. with cooling. The reaction was evaporated to dryness by direct aspiration under high vacuum while maintaining cooling. The residue was washed down with a little dry CH$_2$Cl$_2$ and re-aspirated under high vacuum. The residue was dissolved in 0.5 mL MeCN, an aliquot withdrawn, and the remainder aspirated under high vacuum to dryness. The withdrawn aliquot was analyzed by analytical HPLC (gradient: as given above, but at 1 mL/min), which indicated the presence of largely starting material (P) [tR~18.1 min] together with new product peaks at shorter retention times. Careful inspection of the peak corresponding to starting material indicated (UV) that the MEM protecting group was also partially being removed, with the des-MEM material almost co-running with actual starting material. The reaction residue was redissolved in dry CH$_2$Cl$_2$ (200 μL) and re-treated with TFA in CH$_2$Cl$_2$ exactly as above (second treatment), but with stirring for 20 min. Aspiration and handling as described above and HPLC analysis of the aliquot of the reaction showed progressive decrease of (P) and appearance of a cascade of faster-running peaks. A third treatment with TFA/CH$_2$Cl$_2$ as described above (30 min/~4° C.) and HPLC analysis; followed by a fourth treatment with TFA (30 μL)/CH$_2$Cl$_2$ (90 μL, 30 min/~4° C.) and HPLC analysis; and a final fifth treatment with TFA (30 μL)/CH$_2$Cl$_2$ (90 μL, 2 hours/~4° C.) and HPLC analysis; progressively showed the disappearance of all starting material (P) [tR~18.1] and a cascade of intermediate faster-running peaks changing over time and tending to accumulate in one major front-running peak [tR~10.4 min]. No significant amount of the parent 5'-isoprenyl[OH]-MPA (3A, formed from undesired concomitant rupture of the allylic carbamate of the linker) was observed, by comparison with known material. Adjustments of the gradients in the final analytical HPLC analyses both confirmed negligible (3A), if any, being present, and also allowed for the better spread of peaks. The reaction was aspirated to dryness under high vacuum, redissolved in 3:1 MeCN-water, and purified by semi-preparative RP-HPLC (Column: Vydac 218TP510; 300 Å, 5μ, C18, 10×250 mm. Guard: Vydac 218GK54. Gradient: 0% [C=MeCN containing 0.1% TFA] at 0 min, rising to 75% C at 30 min, rising to 100% C at 35 min, then falling to 0% C at 40 min; in [A=water containing 0.1% TFA]; flow rate=3 mL/min, 3 runs). The product peaks [tR~17.8 min] were collected and evaporated to dryness under high vacuum (at <25° C.) to give the gentamicin-MPA conjugate (carbamate linkage, R, <0.5 mg) as a white solid. $^1$H-NMR: compatible. LR(+)FAB MS: M+H 880.4. HR(+)FAB MS: Calc M+H 880.4555, Observed 880.4553.

In an alternate method for deprotection of (N) to (R), fully protected gentamicin-MPA (N, 21.0 mg) was dissolved in MeOH (4.2 mL) and treated with a solution of LiOH (42 mg in 2.1 mL water). The clear reaction was stirred at room temperature under argon for 4 d after which analytical HPLC showed the reaction to be largely complete. The mixture was acidified with dilute phosphoric acid (2 drops 85% H$_3$PO$_4$ in 2 mL water) to approx. pH 5. The mixture, now containing some precipitated lithium phosphate, was stirred and agitated, diluted with water and MeOH, the pH readjusted to approx. pH 4–5 with more dilute phosphoric acid and the mixture stirred and agitated for a toal of about 2 hours. The mixture was evaporated to dryness under reduced pressure, then under high vacuum. The solid residue was triturated with MeOH, the solids filtered off, and the filtrates evaporated to dryness to afford oily solids. Analytical HPLC indicated that the product mixture contained fully deprotected MPA-gentamicin (R) together with lesser amounts of the cascade of the various intermediate partially deprotected species, by comparison with the previous experiment. The material was dissolved in 1:1 MeCN-water and purified by preparative RP-HPLC (gradient of 0% increasing to 75% over 40 min, then isocratic at 75% until 60 min, then increasing to 100% over 20 min of [0.1% trifluoroacetic acid (TFA)/MeCN] in [0.1% TFA/water]; flow rate=10 mL/min)

to give, from the front-running (major) peak after lyophilization the desired gentamicin-MPA (R, 4.8 mg) as a white solid. $^1$H-NMR: compatible. LR(+)FAB MS: compatible. HR(+)FAB MS: Calc M+H 880.4555, Observed 880.4561.

EXAMPLE 51

Partial Base Hydrolysis of (N): Isolation of Intermediate 5'-[(N2',N3,N6'-tri-tbutoxycarbonyl-gentamicin[C1a]-N1-carbonyl-oxy)-isoprenyl]-MPA [OMEM] methyl ester conjugate (Q)

In yet another experiment, 1.0 mg of (N) in 200 µL of DMF was treated with 2 mg of LiOH in 100 µL water in a similar manner to that as described above, diluting with an additional 20 µL of water to obtain a clear solution. Analytical HPLC indicated that the intermediate (Q) was formed fairly quickly, but that further reaction to (P) was very slow. After stirring overnight at room temperature the reaction was quenched and worked up as described above and purified by semi-preparative HPLC in a manner as described above. The peaks containing product [tR~22½ min] were collected and lyophilized to give the partially deprotected intermediate (Q, <0.5 mg). $^1$H-NMR: compatible.

EXAMPLE 52

Preparation of protected gentamicin-MPA conjugate (amide linkage), 5'-[(N2',N3,N6'-tri-tbutoxycarbonyl-N3"-trifluoroacetyl-gentamicin[C1a]-N1-terephthaloyl)-amino-isoprenyl]-MPA[OMEM] methyl ester conjugate (S)

To 15 g (73.8 mmol) of terephthaloyl chloride was added 300 mL of dichloromethane. The mixture was allowed to stir at 0° C. for 10 minutes under an argon atmosphere. To the reaction mixture was added 30 g (0.26 mol) of N-hydroxysuccinimide, followed by the dropwise addition of 30 mL (0.22 mol) of triethylamine at 0° C. The mixture was allowed to warm at room temperature and then stirred at room temperature for 2 days. The solid was filtered off and the residue washed with 200 mL of dichloromethane. The residue was suspended in 300 mL of dichloromethane and allowed to stir for 10 minutes. The solid was filtered and dried to give 24.12 g (66.9 mmol, 91%) the product 1,4-di-N-hydroxysuccinimide ester of terephthalic acid as a white powder.

To 64.5 mg of 1,4-di-N-hydroxysuccinimide ester of terephthalic acid was added 6 mL of anhydrous DMF to produce a di-N-hydroxysuccinimide (di-NHS) ester solution. In another flask was added 64.5 mg (0.17 mmol) of (Z1), 6 mL of anhydrous DMF, and 128 µL (0.89 mmol) of triethylamine. This gentamnicin amine solution was added to the di-NHS ester solution dropwise under an argon atmosphere. The mixture was allowed to stir at room temperature for 48 h and was then concentrated. The residue was purified by silica gel column chromatography using 9:1 mixture of ethyl acetate and hexane as eluent. The fractions coming out of the column were analyzed by TLC, detecting the desired product under short wave WV. The Rf of the product in the same solvent system used for column was 0.36. The fractions containing the product were combined and concentrated, and then purified by preparative reverse-phase high performance liquid chromatography (RP-HPLC) using a gradient run at 10 mL/min. The desired fractions were combined, concentrated in the rotary evaporator at room temperature and then lyophilized to give 49 mg (0.044 mmol, 26%) of 3,2',6'-tri-t-butoxycarbonyl-3"-N-(trifluoro-acetyl) gentamicin C1a-N1 position-aromatic-substituted NHS ester (Z) as a white powder.

To 24 mg (0.047 mmol) of MPA amine (B) was added 1.7 µL of anhydrous DMF followed by 100 µL of triethylamine. To the reaction mixture was added a solution of 26.2 mg (0.023 mmol) of the gentamicin NHS ester:2',3,6'-tri-t-butoxycarbonyl-3"(N-trifluoroacetyl)-gentamicin[C1a]-N$^1$-terephthaloyl-NHS ester (Z) in 1.8 mL of anhydrous DMF. The mixture was allowed to stir at room temperature for 18 hours under argon. The reaction mixture was concentrated under reduced pressure and the residue was purified by preparative thin layer chromatography (20×20 cm×0.025 cm silica thickness plates) using 5% methanol in ethyl acetate to give 19 mg (0.012 mmol, 54%) of protected MPA-gentamicin conjugate (S) as a white solid. $^1$H-NMR: compatible. LC/MS: M+H 1504.6.

EXAMPLE 53

Preparation of partially protected gentamicin-MPA conjugate (amide linkage), 5'-[(N2',N3,N6'-tri-tbutoxycarbonyl-gentamicin[C1a]-N1-terephthaloyl)-amino-isoprenyl]-MPA[OMEM] conjugate (T)

To 12 mg (0.008 mmol) of MPA-gentamicin (protected) conjugate (S) was added 1.5 mL of methanol and 24 mg of lithium hydroxide monohydrate and 750 µL of water. The mixture was allowed to stir at room temperature for 3 days. An additional 24 mg of lithium hydroxide monohydrate in 750 µL of water was added. The reaction mixture was allowed to stir at room temperature for 2 more days and then concentrated to dryness under reduced pressure. To the residue 2 µL of water was added and the pH was adjusted to 6–7. The resulting solution was concentrated and the residue was mixed with 3×50 mL of methanol and filtered. The filtrate was concentrated to dryness and the residue purified by preparative thin layer chromatography (20 ×20 cm×0.025 cm silica thickness plates) using 50% ethyl acetate in methanol to give 7 mg (0.005 mmol, 70%) of protected gentamicin-C1a-MPA conjugate (T) as a white powder. $^1$H-NMR: compatible. LC/MS: M+H 1372.6

EXAMPLE 54

Preparation of gentamicin-MPA conjugate (amide linkage), 5'-[(gentamicin[C1a]-N1-terephthaloyl)-amino-isoprenyl]-MPA conjugate (amide linkage, U)

To 7 mg (0.005 mmol) of protected gentamicin-C1a-MPA conjugate (T) was added 1 mL of dry dichloromethane and the solution cooled to 0° C. To the reaction mixture 500 µL of trifluoroacetic acid was added and the reaction mixture was stirred for 15 minutes while warming up to room temperature. The resulting mixture was concentrated to dryness under reduced pressure. The residue was purified by semi-preparative RP-HPLC (C-18, Vydac 218TP510, 10 mm×250 mm; Vydac 218GK54 guard module) using a gradient system of water/acetonitrile containing 0.1% trifluoroacetic acid (flow rate=3 mL/min). Fractions containing product were combined and lyophilized to give 3 mg (0.003 mmol, 60%) of U as a white powder. $^1$H-NMR: compatible. LR (+) FAB MS: M+H 982. HR-ES MS: Calcd (M+2H)$^{2+}$ 492.2523, Observed 492.2528.

EXAMPLE 55

Preparation of phenytoin-3-butyric acid NHS ester (W)

5,5-Diphenylhydantoin-3-butyric acid (V, phenytoin-3-butyric acid) was prepared according to the procedure described in ES 389999.

To a solution of 1.5 g (4.43 mmol) of 5,5-diphenylhydantoin-3-butyric acid (V) in 10 mL of dry pyridine and 5 mL of dry DMF under argon was added 2.52 g (8.87 mmol) of disuccinimidyl oxalate in one lot as a solid. After stirring at room temperature for 18 h solvent was removed, 50 mM potassium phosphate (pH 10) was added, and the mixture extracted with ethyl acetate (2×150 mL) and $CH_2Cl_2$ (2×150 mL). The organic extracts were evaporated to give 1.29 g (from the ethyl acetate layers) and 0.61 g (from the $CH_2Cl_2$ layers) of white solids. The combined solids were dissolved in 500 mL of ethyl acetate containing 2% DMF with gentle warming (~30° C. and stirred over sat. aq. $NaHCO_3$ for 30 minutes. The organic layer was isolated and stirred again with sat. aq. $NaHCO_3$ for 30 minutes. The organic layer was then dried ($Na_2SO_4$), filtered, evaporated and dried under vacuum to give 1.61 g of the desired NHS ester (W). $^1$H-NMR: compatible. LR (+) APCI MS: 436 (M+H). Microanalysis: Calcd for $C_{23}H_{21}N_3O_6 \cdot \frac{1}{10}CH_3COOC_2H_5$:C, 63.27; H, 4.95; N, 9.46%. Observed:C, 63.25; H, 4.98; N, 9.46%.

EXAMPLE 56

Preparation of 5'-[(phenytoin-3-butyramido)-isoprenyl]-MPA[OMEM] methyl ester conjugate (X)

To a solution of 37 mg (0.073 mmol) of MPA-5'-isoprenylamine (B), from Example 45, in 5 mL of anhydrous DMF was added 200 μL of triethylamine. To the reaction mixture a solution of 52 mg (0.12 mmol) of phenytoin-3-butyric acid NHS ester (W) from Example 55 in 1 mL of anhydrous DMF was added dropwise. The resulting solution was allowed to stir at room temperature for 18 h and then concentrated to dryness under reduced pressure. The residue was purified by silica gel column chromatography using 50% ethyl acetate in hexane to give 48 mg of the desired product containing some impurities. The mixture was repurified by preparative layer chromatography (20×20 cm×0.2 cm silica thickness plates) using 5%hexane in ethyl acetate to give 26 mg (0.031 mmol, 61%) of protected conjugate (X). $^1$H-NMR: compatible. LC/MS: M+H 826.3.

EXAMPLE 57

Preparation of phenytoin-MPA conjugate, 5'-[(phenytoin-3-butyramido)-isoprenyl]-MPA conjugate (Y)

To 22 mg (0.026 mmol) of protected conjugate (X), from Example 56, was added 4.5 mL of methanol and 2 mL of water followed by 100 mg of lithium hydroxide monohydrate. The mixture was allowed to stir at room temperature for 72 hours and then concentrated under reduced pressure. To the residue 1 mL of water was added and the pH of the reaction mixture was adjusted to 6 using dilute phosphoric acid (1 mL 85% $H_3PO_4$ in 9 mL water). The resulting reaction mixture was concentrated to dryness under reduced pressure. The residue was triturated with 15 mL of methanol and the inorganic solids were filtered off. The filtrate was concentrated and purified by preparative thin layer chromatography (20×20 cm×0.025 silica thickness) using 50% ethyl acetate in hexane to give 12 mg (0.016 mmol, 63%) of phenytoin-MPA conjugate (Y). $^1$H-NMR: compatible. HR-ES (+) MS: Calcd for M+Na 746.3048, Observed 746.3044.

EXAMPLE 58

Assays for Phenytoin and Gentamicin

Assays for phenytoin and gentamicin were performed with a HITACHI 917 as follows: 3 μL sample was added to a cuvette and 150 μL enzyme reagent was added, mixed and incubated @ 37° C. for 5 minutes, then 150 μL antibody reagent was added and mixed. The absorbance rate at 340 nm was monitored 9–10 minutes following the addition of the antibody reagent. A calibration curve was constructed using standards containing known amounts of phenytoin or gentamicin. Values for phenytoin or gentamicin were calculated by the HITACHI 917 analyzer. Roche INTEGRA phenytoin or gentamicin calibrators and a Roche INTEGRA FP phenytoin or gentamicin reagent cassettes were used with a Roche INTEGRA 700 analyzer for the method comparison studies. Passing/Bablock regression statistics were used. Patient samples were plasma. Composition of enzyme reagent and antibody reagents are described below:

| Enzyme reagent formulation: | |
| --- | --- |
| Tris | 100 mM |
| KCL | 100 mM |
| IMP | 80 mM |
| TCEP | 4 mM |
| EDTA | 6 mM |
| Phenytoin-isoprenyl-MPA (racemic) or gentamicin-isoprenyl-MPA (racemic) derivatives | 1.47 μM |
| SUTTOCIDE A | 4 mM |
| MAB | 0.1 mg/mL |
| IMPDH-II | Adjust to rate |
| pH 8.0 | |
| Antibody reagent formulation: | |
| NAD | 1 mM |
| SUTTOCIDE A | 4 mM |
| NP-40 | 0.175% |
| pH 6.0 | |

What is claimed is:

1. A ligand-inhibitor conjugate with the structure

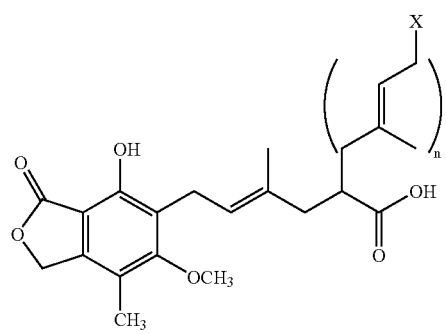

wherein n=1 and X is selected from the group consisting of —O—CONH—$(CH_2)_2$-NH-thyroxine, —O—CONH—$(CH_2)_2$—NHC(=C)—$(CH_2)_4$-theophylline, —NH—CO—$(CH_2)_3$-phenytoin, —O—CO[NH-gentamicin], —NH—

CO-Ph-CO[NH-gentamicin] wherein Ph is phenyl, 5'-[[[(digoxin(1,4-oxazepin))-4-yl]-phenyl-4-carbonyl]amino]-, 5'-[[[(digitoxin(1,4-oxazepin))-4-yl]-phenyl-4-carbonyl]amino]-, and 2. The conjugate of claim 1 wherein X is —O—CONH—(CH$_2$)$_2$—NH-thyroxine.

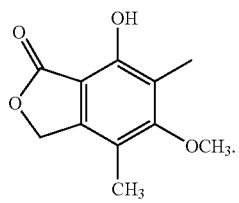

3. The conjugate of claim 1 wherein X is —O—CONH—(CH$_2$)$_2$—NHC(=C)—(CH$_2$)$_4$-theophylline.

4. The conjugate of claim 1 wherein X is

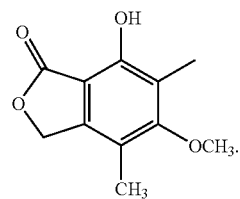

5. The conjugate of claim 1 wherein X is —NH—CO—(CH$_2$)$_3$-phenytoin.

6. The conjugate of claim 1 wherein X is —O—CO[NH-gentamicin].

7. The conjugate of claim 1 wherein X is —NH—CO-Ph-CO[NH-gentamicin] and Ph is phenyl.

8. The conjugate of claim 1 wherein X is 5'-[[[(digoxin(1,4-oxazepin))-4-yl]-phenyl-4-carbonyl]amino]-.

9. The conjugate of claim 1 wherein X is 5'-[[[(digitoxin(1,4-oxazepin))-4-yl]-phenyl-4-carbonyl]amino]-.

10. The compound of claim 1 that is 5'-[(theophylline-8-butyramidoethylaminocarbonyloxy)isoprenyl]-MPA.

* * * * *